US008401799B2

(12) United States Patent
Sabbadini et al.

(10) Patent No.: US 8,401,799 B2
(45) Date of Patent: Mar. 19, 2013

(54) ANTIBODY DESIGN USING ANTI-LIPID ANTIBODY CRYSTAL STRUCTURES

(75) Inventors: Roger A. Sabbadini, Lakeside, CA (US); Tom Huxford, San Diego, CA (US); Jonathan Michael Wojciak, Encinitas, CA (US)

(73) Assignee: Lpath, Inc., San Diego, CA (US)

( * ) Notice: Subject to any disclaimer, the term of this patent is extended or adjusted under 35 U.S.C. 154(b) by 0 days.

(21) Appl. No.: 12/794,668

(22) Filed: Jun. 4, 2010

(65) Prior Publication Data
US 2011/0118443 A1   May 19, 2011

Related U.S. Application Data

(63) Continuation-in-part of application No. 12/631,784, filed on Dec. 4, 2009.

(60) Provisional application No. 61/120,318, filed on Dec. 5, 2008, provisional application No. 61/155,895, filed on Feb. 26, 2009, provisional application No. 61/231,258, filed on Aug. 4, 2009.

(51) Int. Cl.
A61K 39/395 (2006.01)
C07K 16/44 (2006.01)
G06G 7/60 (2006.01)

(52) U.S. Cl. ............ 702/19; 424/141.1; 424/130.1; 530/387.3; 530/388.1; 703/11

(58) Field of Classification Search ............ None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,225,539 A | 7/1993 | Winter | |
| 5,229,275 A | 7/1993 | Goroff | |
| 5,530,101 A | 6/1996 | Queen et al. | |
| 5,534,615 A | 7/1996 | Baker et al. | |
| 5,545,807 A | 8/1996 | Surani et al. | |
| 5,565,332 A | 10/1996 | Hoogenboom et al. | |
| 5,567,610 A | 10/1996 | Borrebaeck et al. | |
| 5,573,905 A | 11/1996 | Lerner et al. | |
| 5,585,089 A | 12/1996 | Queen et al. | |
| 5,589,369 A | 12/1996 | Seidman et al. | |
| 5,591,669 A | 1/1997 | Krimpenfort et al. | |
| 5,624,821 A | 4/1997 | Winter et al. | |
| 5,639,641 A * | 6/1997 | Pedersen et al. ............ 435/69.6 |
| 5,693,761 A * | 12/1997 | Queen et al. ............ 536/23.53 |
| 5,693,762 A | 12/1997 | Queen et al. | |
| 5,714,350 A | 2/1998 | Co et al. | |
| 5,731,168 A | 3/1998 | Carter et al. | |
| 5,777,085 A | 7/1998 | Co et al. | |
| 5,834,597 A | 11/1998 | Tso et al. | |
| 5,861,155 A | 1/1999 | Lin | |
| 5,882,644 A | 3/1999 | Chang et al. | |
| 5,932,448 A | 8/1999 | Tso et al. | |
| 6,013,256 A | 1/2000 | Light et al. | |
| 6,096,871 A | 8/2000 | Presta et al. | |
| 6,129,914 A | 10/2000 | Weiner et al. | |
| 6,180,370 B1 | 1/2001 | Queen et al. | |
| 6,210,671 B1 | 4/2001 | Co | |
| 6,329,511 B1 | 12/2001 | Vasquez et al. | |
| 6,350,861 B1 | 2/2002 | Co et al. | |
| 6,407,213 B1 | 6/2002 | Carter et al. | |
| 6,479,284 B1 | 11/2002 | Marasco et al. | |
| 6,500,931 B1 | 12/2002 | Tempest et al. | |
| 6,548,640 B1 | 4/2003 | Winter | |
| 6,639,055 B1 | 10/2003 | Carter et al. | |
| 6,858,383 B2 | 2/2005 | Sabbadini | |
| 6,881,546 B2 | 4/2005 | Sabbadini | |
| 7,060,808 B1 | 6/2006 | Goldstein et al. | |
| 7,829,674 B2 | 11/2010 | Sabbadini et al. | |
| 2003/0096022 A1 | 5/2003 | Sabbadini | |
| 2003/0166871 A1 | 9/2003 | Barbas, III et al. | |
| 2003/0229208 A1 | 12/2003 | Queen et al. | |
| 2004/0110226 A1 * | 6/2004 | Lazar et al. ............ 435/7.1 |
| 2004/0265367 A1 | 12/2004 | Thorpe et al. | |
| 2007/0148168 A1 | 6/2007 | Sabbadini et al. | |
| 2007/0281320 A1 | 12/2007 | Sabbadini et al. | |
| 2008/0090303 A1 | 4/2008 | Sabbadini et al. | |
| 2008/0138334 A1 | 6/2008 | Sabbadini et al. | |
| 2008/0145360 A1 | 6/2008 | Sabbadini et al. | |
| 2008/0213274 A1 * | 9/2008 | Sabbadini et al. ......... 424/141.1 |
| 2009/0010922 A1 | 1/2009 | Sabbadini et al. | |

FOREIGN PATENT DOCUMENTS

| | | |
|---|---|---|
| EP | 0125023 B1 | 6/1991 |
| EP | 0519596 A1 | 12/1992 |
| EP | 0120694 B1 | 7/1993 |
| EP | 0194276 B1 | 8/1993 |
| EP | 0239400 B1 | 8/1994 |
| WO | 86/01533 A1 | 3/1986 |
| WO | 2007/038392 A2 | 4/2007 |
| WO | 2007/053447 A2 | 5/2007 |
| WO | 2008/055072 A2 | 5/2008 |
| WO | 2008/070344 A2 | 6/2008 |

OTHER PUBLICATIONS

Ahamed et al., Biochem. J., 2007, 610-619, 93(2).
Benvenuti et al., Nat. Protoc., 2007, 1633-1651, 2(7).
Chothia et al., J. Mol. Biol., 1985, 651-663, 186(3).
Chothia et al., J. Mol. Biol., 1987, 901-917, 196(4).
Clackson et al., Nature, 1991, 624-628, 352(6336).
Collaborative Computational Project No. 4, Acta Crystallogr. D Biol. Crystallogr., 1994, 760-763, 50(5).
Cudney, The Rigaku J., 1999, 1-7, 16(2).

(Continued)

Primary Examiner — Michael Borin
(74) Attorney, Agent, or Firm — Acuity Law Group, P.C.; Daniel M. Chambers

(57) ABSTRACT

Methods for designing optimized antibodies, including optimized humainized or human antibodies, to target bioactive lipids are provided. These methods may be performed in silico and may be intended to enhance binding affinity of an antibody to its original target lipid, and/or to alter binding specificity. Antibodies produced by these methods are also provided, as are methods for using them.

7 Claims, 4 Drawing Sheets

OTHER PUBLICATIONS

Drenth, Principle of Protein X-Ray Crystallography, 2nd Ed., 1-21, Ch. 1, Springer-Verlag, New York Inc.
Foote et al., J. Mol. Biol., 1992, 487-499, 224(2).
Fujiwara et al., J. Biol. Chem., 2005, 35038-35050, 280(41).
Hoogenboom et al., J. Mol. Biol., 1991, 381-388, 227(2).
Jones et al., Nature, 1986, 522-525, 321(6069).
Kabat, Pharmacol. Rev., 1982, 23-38, 34(1).
Kabat et al., Sequences of Proteins of Immunological Interest, 5th Ed., 1992, 647-669, NIH Pub. : 91-3242 , U.S. Department of Health and Human Services, Public Health Service, National Institutes of Health, Bethesda, MD, USA.
Kleywegt et al., Acta Crystallogr. D Biol. Crystallogr., 1998, 1119-1131, 54(Pt 6, No. 1).
Kundrot, Cel. Mol. Life Sci., 2004, 525-536, 61(5).
Marks et al., J. Mol. Biol., 1991, 581-597, 222(3).
McCoy et al., J. Appl. Crystallogr., 2007, 658-674, 40(4).
McPherson, Eur. J. Biochem., 1990, 1-23, 189(1).
McRee, J. Struct. Biol., 1999, 156-165, 125(2-3).
Moon et al., Protein Sci., 2010, 901-913, 19(5).
Morea et al., Methods, 2000, 267-279, 20(3).
Munson et al., Anal. Biochem., 1980, 220-239, 107(1).
Murshudov et al., Acta Crystallogr. D53 Biol. Crystallogr., 1997, 240-255, 53(3).
Ofek et al., J. Virol., 2004, 10724-10737, 78(19).
Otwinowski et al., Meth. Enzymol., 1997, 307-326, 276, Macromol. Crystallogr. Pt A.
Presta, Antibody Engineering, Curr. Opin. Struct. Biol., 1992, 593-596, 2(6).
Wang et al., J. Biol. Chem., 2001, 49213-49220, 276(52).
Wojciak et al., Proc. Nat. Acad. Sci. USA, 2009, 17717-17722, 106(42).
Zhou et al., Proc. Natl. Acad. Sci. USA, 2005, 14575-14580, 102(41).

* cited by examiner

ANTIBODY DESIGN USING ANTI-LIPID ANTIBODY CRYSTAL STRUCTURES

RELATED APPLICATIONS

This patent application claims the benefit of and priority to U.S. provisional patent application Ser. Nos. 61/120,318, filed 5 Dec. 2008, 61/155,895,filed 26 Feb. 2009, and 61/231,258, filed 4 Aug. 2009 and to U.S. non-provisional patent application serial no. 12/631,784, filed 4 Dec. 2009, of which this application is a continuation-in-part. This application also claims priority to and the benefit of PCT patent application serial no. PCT/US09/66862, filed 4 Dec. 2009. Each of the foregoing patent applications is hereby incorporated by reference in its entirety for any and all purposes.

SEQUENCE LISTING

The instant application contains a Sequence Listing which has been submitted via EFS-Web and is hereby incorporated by reference in its entirety. Said ASCII copy, created on Jun. 4, 2010, is named LPT4000 CP.txt, and is 38,857 bytes in size.

GRANT SUPPORT

The subject matter of this application was supported at least in part by Small Business Innovation Research (SBIR) grant no. 1 R43 GM 088956-01. The U.S. Government may have certain rights herein.

BACKGROUND OF THE INVENTION

1. Field of the Invention

The present invention relates to crystalline forms of anti-lipid antibodies, methods of making them, and methods of using data derived therefrom in antibody design and optimization. Methods for designing antibodies or antibody fragments are provided, wherein the antibody target is a lipid, such as a bioactive lipid.

The following description includes information that may be useful in understanding the present invention. It is not an admission that any of the information provided herein, or any publication specifically or implicitly referenced herein, is prior art, or even particularly relevant, to the presently claimed invention.

2. Background

Bioactive Signaling Lipids

Lipids and their derivatives are now recognized as important targets for medical research, not as just simple structural elements in cell membranes or as a source of energy for β-oxidation, glycolysis or other metabolic processes. In particular, certain bioactive lipids function as signaling mediators important in animal and human disease. Although most of the lipids of the plasma membrane play an exclusively structural role, a small proportion of them are involved in relaying extracellular stimuli into cells. "Lipid signaling" refers to any of a number of cellular signal transduction pathways that use cell membrane lipids as second messengers, as well as referring to direct interaction of a lipid signaling molecule with its own specific receptor. Lipid signaling pathways are activated by a variety of extracellular stimuli, ranging from growth factors to inflammatory cytokines, and regulate cell fate decisions such as apoptosis, differentiation and proliferation. Research into bioactive lipid signaling is an area of intense scientific investigation as more and more bioactive lipids are identified and their actions characterized.

Examples of bioactive lipids include the eicosanoids (including the cannabinoids, leukotrienes, prostaglandins, lipoxins, epoxyeicosatrienoic acids, and isoeicosanoids) such as the hydroxyeicosatetraenoic acids (HETEs, including 5-HETE, 12-HETE, 15-HETE and 20-HETE), non-eicosanoid cannabinoid mediators, phospholipids and their derivatives such as phosphatidic acid (PA) and phosphatidylglycerol (PG), platelet activating factor (PAF) and cardiolipins as well as lysophospholipids such as lysophosphatidyl choline (LPC) and various lysophosphatidic acids (LPA). Bioactive signaling lipid mediators also include the sphingolipids such as sphingomyelin, ceramide, ceramide-1-phosphate, sphingosine, sphingosylphosphoryl choline, sphinganine, sphinganine-1-phosphate (Dihydro-S1P) and sphingosine-1-phosphate. Sphingolipids and their derivatives represent a group of extracellular and intracellular signaling molecules with pleiotropic effects on important cellular processes. Other examples of bioactive signaling lipids include phosphatidylserine (PS), phosphatidylinositol (PI), phosphatidylethanolamine (PEA), diacylglyceride (DG), sulfatides, gangliosides, and cerebrosides.

Sphingolipids are a unique class of lipids that were named, due to their initially mysterious nature, after the Sphinx. Sphingolipids were initially characterized as primary structural components of cell membranes, but recent studies indicate that sphingolipids also serve as cellular signaling and regulatory molecules (Hannun, et al., Adv. Lipid Res. 25:27-41, 1993; Speigel, et al., FASEB J. 10:1388-1397, 1996; Igarashi, J. Biochem 122:1080-1087, 1997; Hla, T. (2004). *Semin Cell Dev Biol*, 15, 513-2; Gardell, S. E., Dubin, A. E. & Chun, J. (2006). *Trends Mol Med*, 12, 65-75). Sphingolipids are primary structural components of cell membranes that also serve as cellular signaling and regulatory molecules (Hannun and Bell, Adv. Lipid Res. 25: 27-41, 1993; Igarashi, J. Biochem 122: 1080-1087, 1997). The sphingolipid signaling mediators, ceramide (CER), sphingosine (SPH) and sphingosine-1-phosphate (S1P), have been most widely studied and have recently been appreciated for their roles in the cardiovascular system, angiogenesis and tumor biology (Claus, et al., Curr Drug Targets 1: 185-205, 2000; Levade, et al., Circ. Res. 89: 957-968, 2001; Wang, et al., J. Biol. Chem. 274: 35343-50, 1999; Wascholowski and Giannis, Drug News Perspect. 14: 581-90, 2001; Spiegel, S. & Milstien, S. (2003). Sphingosine-1-phosphate: an enigmatic signaling lipid. *Nat Rev Mol Cell Biol*, 4, 397-407).

For a review of sphingolipid metabolism, see Liu, et al., Crit. Rev. Clin. Lab. Sci. 36:511-573, 1999. For reviews of the sphingomyelin signaling pathway, see Hannun, et al., Adv. Lipid Res. 25:27-41, 1993; Liu, et al., Crit. Rev. Clin. Lab. Sci. 36:511-573, 1999; Igarashi, J. Biochem. 122:1080-1087, 1997; Oral, et al., J. Biol. Chem. 272:4836-4842, 1997; and Spiegel et al., Biochemistry (Moscow) 63:69-83, 1998.

Sphingosine-1-Phosphate (S1P)

S1P is a mediator of cell proliferation and protects from apoptosis through the activation of survival pathways (Maceyka, et al. (2002), BBA, vol. 1585): 192-201, and Spiegel, et al. (2003), Nature Reviews Molecular Cell Biology, vol. 4: 397-407). It has been proposed that the balance between CER/SPH levels and S1P provides a rheostat mechanism that decides whether a cell is directed into the death pathway or is protected from apoptosis. The key regulatory enzyme of the rheostat mechanism is sphingosine kinase (SPHK) whose role is to convert the death-promoting bioactive signaling lipids (CER/SPH) into the growth-promoting S1P. S1P has two fates: S1P can be degraded by S1P lyase, an enzyme that cleaves S1P to phosphoethanolamine and hexadecanal, or, less common, hydrolyzed by S1P phosphatase to SPH.

The pleiotropic biological activities of S1P are mediated via a family of G protein-coupled receptors (GPCRs) originally known as Endothelial Differentiation Genes (EDG). Five GPCRs have been identified as high-affinity S1P receptors (S1PRs): $S1P_1$/EDG-1, $S1P_2$/EDG-5, $S1P_3$/EDG-3, $S1P_4$/EDG-6, and $S1P_5$/EDG-8 only identified as late as 1998 (Lee, et al., 1998). Many responses evoked by S1P are coupled to different heterotrimeric G proteins ($G_q$, $G_1$, $G_{12-13}$) and the small GTPases of the Rho family (Gardell, et al., 2006).

In the adult, S1P is released from platelets (Murata et al., 2000) and mast cells to create a local pulse of free S1P (sufficient enough to exceed the $K_d$ of the S1PRs) for promoting wound healing and participating in the inflammatory response. Under normal conditions, the total S1P in the plasma is quite high (300-500 nM); however, it has been hypothesized that most of the S1P may be 'buffered' by serum proteins, particularly lipoproteins (e.g., HDL>LDL>VLDL) and albumin, so that the bio-available S1P (or the free fraction of S1P) is not sufficient to appreciably activate S1PRs (Murata et al., 2000). If this were not the case, inappropriate angiogenesis and inflammation would result. Intracellular actions of S1P have also been suggested (see, e.g., Spiegel S, Kolesnick R (2002), Leukemia, vol. 16: 1596-602; Suomalainen, et al (2005), Am J Pathol, vol. 166: 773-81).

Widespread expression of the cell surface S1P receptors allows S1P to influence a diverse spectrum of cellular responses, including proliferation, adhesion, contraction, motility, morphogenesis, differentiation, and survival. This spectrum of response appears to depend upon the overlapping or distinct expression patterns of the S1P receptors within the cell and tissue systems. In addition, crosstalk between S1P and growth factor signaling pathways, including platelet-derived growth factor (PDGF), vascular endothelial growth factor (VEGF), and basic fibroblastic growth factor (bFGF), have recently been demonstrated (see, e.g., Baudhuin, et al. (2004), FASEB J, vol. 18: 341-3). The regulation of various cellular processes involving S1P has particular impact on neuronal signaling, vascular tone, wound healing, immune cell trafficking, reproduction, and cardiovascular function, among others. Alterations of endogenous levels of S1P within these systems can have detrimental effects, eliciting several pathophysiological conditions, including cancer, inflammation, angiogenesis, heart disease, asthma, and autoimmune diseases.

A recent novel approach to the treatment of various diseases and disorders, including cardiovascular diseases, cerebrovascular diseases, and various cancers, involves reducing levels of biologically available S1P, either alone or in combination with other treatments. While sphingolipid-based treatment strategies that target key enzymes of the sphingolipid metabolic pathway, such as SPHK, have been proposed, interference with the lipid mediator S1P itself has not until recently been emphasized, largely because of difficulties in directly mitigating this lipid target, in particular because of the difficulty first in raising and then in detecting antibodies against the S1P target.

Recently, the generation of antibodies specific for S1P has been described. See, e.g., commonly owned, U.S. patent application Serial No. 20070148168; WO2007/053447. Such antibodies, which can, for example, selectively adsorb S1P from serum, act as molecular sponges to neutralize extracellular S1P. See also commonly owned U.S. Pat. Nos. 6,881, 546 and 6,858,383 and U.S. patent application Ser. No. 10/029,372. SPHINGOMAB™, the murine monoclonal antibody (mAb) developed by Lpath, Inc. and described in certain patents or patent applications listed above, has been shown to be effective in models of human disease. In some situations, a humanized antibody may be preferable to a murine antibody, particularly for therapeutic uses in humans, where human-anti-mouse antibody (HAMA) response may occur. Such a response may reduce the effectiveness of the antibody by neutralizing the binding activity and/or by rapidly clearing the antibody from circulation in the body. The HAMA response can also cause toxicities with subsequent administrations of mouse antibodies.

A first-in-class humanized anti-S1P antibody (Sonepcizumab, LT1009) has now been developed and is described herein. This antibody is expected to have all the advantages of the murine mAb in terms of efficacy in binding S1P, neutralizing S1P and modulating disease states related to S1P, but with none of the potential disadvantages of the murine mAb when used in a human context. As described in the examples hereinbelow, this humanized antibody has in fact shown activity greater than that of the parent (murine) antibody in animal models of disease. Sonepcizumab is currently in clinical trials for cancer and age-related macular degeneration.

Lysolipids

Lysolipids are low molecular weight lipids that contain a polar head group and a single hydrocarbon backbone, due to the absence of an acyl group at one or both possible positions of acylation. Relative to the polar head group at sn-3, the hydrocarbon chain can be at the sn-2 and/or sn-1 position(s) (the term "lyso," which originally related to hemolysis, has been redefined by IUPAC to refer to deacylation). See "Nomenclature of Lipids, www.chem.qmul.ac.uk/iupac/lipid/lip 1n2.html. These lipids are representative of signaling, bioactive lipids, and their biologic and medical importance highlight what can be achieved by targeting lipid signaling molecules for therapeutic, diagnostic/prognostic, or research purposes (Gardell, et al. (2006), Trends in Molecular Medicine, vol 12: 65-75). Two particular examples of medically important lysolipids are LPA (glycerol backbone) and S1P (sphingoid backbone). Other lysolipids include sphingosine, lysophosphatidylcholine (LPC), sphingosylphosphorylcholine (lysosphingomyelin), ceramide, ceramide-1-phosphate, sphinganine (dihydrosphingosine), dihydrosphingosine-1-phosphate and N-acetyl-ceramide-1-phosphate. In contrast, the plasmalogens, which contain an O-alkyl (—O—$CH_2$—) or O-alkenyl ether at the C-1 (sn1) and an acyl at C-2, are excluded from the lysolipid genus.

The structures of selected LPAs, S1P, and dihydro S1P are presented below.

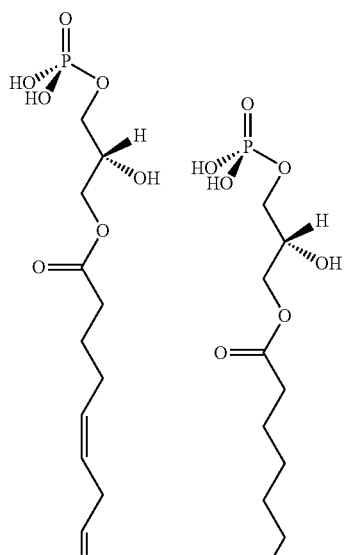
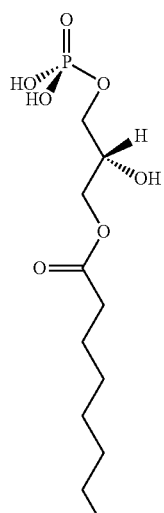
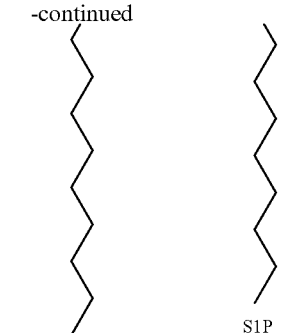
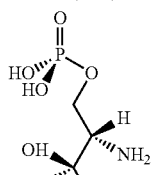

LPA (20:4)   LPA (16:0)   LPA (18:2)   LPA (18:1)   LPA (18:0)   S1P

Dihydo-S1P

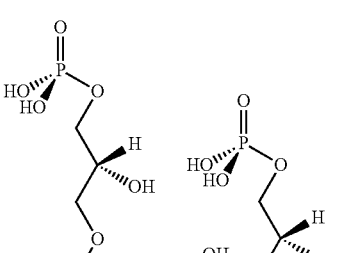
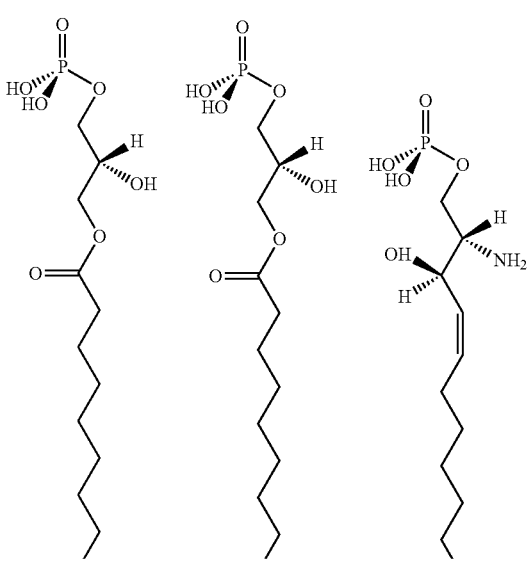
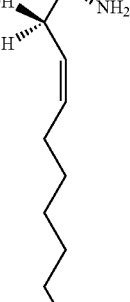

LPA is not a single molecular entity but a collection of endogenous structural variants with fatty acids of varied lengths and degrees of saturation (Fujiwara, et al. (2005), J Biol Chem, vol. 280: 35038-35050). The structural backbone of the LPAs is derived from glycerol-based phospholipids such as phosphatidylcholine (PC) or phosphatidic acid (PA). In the case of lysosphingolipids such as S1P, the fatty acid of the ceramide backbone at sn-2 is missing. The structural backbone of S1P, dihydro S1P (DHS1P) and sphingosylphosphorylcholine (SPC) is based on sphingosine, which is derived from sphingomyelin.

LPA and S1P regulate various cellular signaling pathways by binding to the same class of multiple transmembrane domain G protein-coupled (GPCR) receptors (Chun J, Rosen H (2006), Current Pharm Des, vol. 12: 161-171, and Moolenaar, W H (1999), Experimental Cell Research, vol. 253: 230-238). The S1P receptors are designated as $S1P_1$, $S1P_2$, $S1P_3$, $S1P_4$ and $S1P_5$ (formerly EDG-1, EDG-5/AGR16, EDG-3, EDG-6 and EDG-8) and the LPA receptors designated as $LPA_1$, $LPA_2$, $LPA_3$ (formerly, EDG-2, EDG-4, and EDG-7). A fourth LPA receptor of this family has been identified for LPA ($LPA_4$), and other putative receptors for these lysophospholipids have also been reported.

Lysophosphatic Acids (LPA)

LPAs have long been known as precursors of phospholipid biosynthesis in both eukaryotic and prokaryotic cells, but LPAs have emerged only recently as signaling molecules that are rapidly produced and released by activated cells, notably platelets, to influence target cells by acting on specific cell-surface receptor (see, e.g., Moolenaar, et al. (2004), BioEssays, vol. 26: 870-881, and van Leewen et al. (2003), Biochem Soc Trans, vol 31: 1209-1212). Besides being synthesized and processed to more complex phospholipids in the endoplasmic reticulum, LPA can be generated through the hydrolysis of pre-existing phospholipids following cell activation; for example, the sn-2 position is commonly missing a fatty acid residue due to deacylation, leaving only the sn-1 hydroxyl esterified to a fatty acid. Moreover, a key enzyme in the production of LPA, autotoxin (lysoPLD/NPP2), may be the product of an oncogene, as many tumor types up-regulate autotoxin (Brindley, D. (2004), J Cell Biochem, vol. 92: 900-12). The concentrations of LPA in human plasma and serum have been reported, including determinations made using a sensitive and specific LC/MS procedure (Baker, et al. (2001), Anal Biochem, vol 292: 287-295). For example, in freshly prepared human serum allowed to sit at 25° C. for one hour, LPA concentrations have been estimated to be approximately 1.2 µM, with the LPA analogs 16:0, 18:1, 18:2, and 20:4 being the predominant species. Similarly, in freshly prepared human plasma allowed to sit at 25° C. for one hour, LPA concentrations have been estimated to be approximately 0.7 µM, with 18:1 and 18:2 LPA being the predominant species.

LPA influences a wide range of biological responses, ranging from induction of cell proliferation, stimulation of cell migration and neurite retraction, gap junction closure, and even slime mold chemotaxis (Goetzl, et al. (2002), Scientific World Journal, vol. 2: 324-338). The body of knowledge about the biology of LPA continues to grow as more and more cellular systems are tested for LPA responsiveness. For instance, it is now known that, in addition to stimulating cell growth and proliferation, LPA promote cellular tension and cell-surface fibronectin binding, which are important events in wound repair and regeneration (Moolenaar, et al. (2004), BioEssays, vol. 26: 870-881). Recently, anti-apoptotic activity has also been ascribed to LPA, and it has recently been reported that peroxisome proliferation receptor gamma is a receptor/target for LPA (Simon, et al. (2005), J Biol Chem, vol. 280: 14656-14662). LPA is now recognized as a key signaling molecule involved in the etiology of cancer. Murph, M and Mills, G B (2007) Expert Rev. Mol. Med. 9:1-18.

LPA has proven to be a difficult target for antibody production, although there has been a report in the scientific literature of the production of polyclonal murine antibodies against LPA (Chen et al. (2000) Med Chem Lett, vol 10: 1691-3).

Lpath has recently humanized a monoclonal antibody against LPA, disclosed in US Patent application US20080145360. The humanized anti-LPA antibody, LT3015, exhibits picomolar binding affinity as demonstrated using surface plasmon resonance and is highly specific for LPA.

Structure and Design of Monoclonal Antibodies

Soluble antibodies of the Immunoglobin G (IgG) class consist of a pair of heavy and light chains that are held together by intra- and interchain disulfide bonds to generate the characteristic Y-shaped structure (FIG. 1). In terms of protein tertiary structure, antibodies consist entirely of the immunoglobin domain—a fold that is common to many effector molecules of the immune system. Heavy chains begin with one variable domain (Vh) followed by three constant domains (Ch1-3) while kappa light chains consist of one variable domain (Vk) followed by one constant domain (Ck).

Epitope binding specificity results from variability within the amino-terminal Vh and Vk domains, particularly within six loops (CDR H1, H2, H3, L1, L2 and L3) also known as hypervariable regions.

Treatment of purified whole IgG preparations with the protease papain separates a Fab fragment consisting of both variable domains and the Ck and constant domains from the Fc domain, which contains a pair of Ch2 and Ch3 domains. The Fab fragment retains one entire variable region and, therefore, serves as a useful tool for biochemical characterization of a 1:1 interaction between the antibody and epitope. Furthermore, because it lacks the flexibility and, generally, the glycosylation inherent in native purified whole IgG, the Fab fragment is generally an excellent platform for structural studies via single crystal x-ray diffraction.

Currently, there are over 20 therapeutic antibodies on the market. It is the fastest growing segment of therapeutics largely because humanized mAbs have a high safety profile. The huge success of antibody molecular sponges like Avastin, Lucentis, Humira and Remicade have demonstrated that the use of antibody therapeutics in this mode can also be effective in the treatment of cancer, AMD, inflammatory and autoimmune disorders by neutralizing the target (in the cited cases, protein growth factors) in the extracellular space and depriving receptors of their ligand.

Lpath's ImmuneY2™ technology allows generation of monoclonal antibodies (mAb) against extracellular lipid signaling mediators. Lpath has developed a first-in-class therapeutic agent, a humanized monoclonal antibody Sonepcizumab™ (LT1009; the names Sonepcizumab and LT1009 are herein used interchangeably), which was derived from the murine form of the antibody, Sphingomab™. Sonepcizumab neutralizes the bioactive lipid signaling mediator, sphingosine-1-phosphate (S1P). S1P contributes to disease in cancer, multiple sclerosis, inflammatory disease and ocular diseases that involve dysregulated angiogenesis. A systemic formulation of Sonepcizumab, ASONEP™, is currently in Phase 1 trials for cancer while an ocular formulation of the same mAb, iSONEP™, is in Phase 1 clinical trials for Age-related Macular Degeneration (AMD). Lpath has also recently developed the humanized mAb Lpathomab™ (LT3015; the names Lpathomab and LT3015 are herein used interchangeably), a mAb against the bioactive lipid mediator, lysophosphatidic acid (LPA). In addition to regulating physiological responses such as cell adhesion, motility, cytoskeletal changes, proliferation, angiogenesis, neurite retraction, and cell survival, LPA has been implicated in the pathogenesis and progression of severe diseases including cancer, fibrosis, neuropathic pain, and inflammatory diseases.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

The term "antibody" ("Ab") or "immunoglobulin" (Ig) refers to any form of a peptide, polypeptide derived from, modeled after or encoded by, an immunoglobulin gene, or fragment thereof, that is capable of binding an antigen or epitope. See, e.g., IMMUNOBIOLOGY, Fifth Edition, C. A. Janeway, P. Travers, M., Walport, M. J. Shlomchiked., ed. Garland Publishing (2001). The term "antibody" is used herein in the broadest sense, and encompasses monoclonal, polyclonal or multispecific antibodies, minibodies, heteroconjugates, diabodies, triabodies, chimeric, antibodies, synthetic antibodies, antibody fragments, and binding agents that employ the complementarity determining regions (CDRs) of the parent antibody, or variants thereof that retain antigen binding activity. Antibodies are defined herein as retaining at least one desired activity of the parent antibody. Desired activities can include the ability to bind the antigen specifically, the ability to inhibit proleration in vitro, the ability to inhibit angiogenesis in vivo, and the ability to alter cytokine profile(s) in vitro.

Native antibodies (native immunoglobulins) are usually heterotetrameric glycoproteins of about 150,000 Daltons, typically composed of two identical light (L) chains and two identical heavy (H) chains. The heavy chain is approximately 50 kD in size, and the light chain is approximately 25 kDa. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The light chains of antibodies (immunoglobulins) from any vertebrate species can be assigned to one of two clearly distinct types, called kappa (κ) and lambda (λ), based on the amino acid sequences of their constant domains. The ratio of the two types of light chain varies from species to species. As a way of example, the average κ to λ ratio is 20:1 in mice, whereas in humans it is 2:1 and in cattle it is 1:20.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An "antibody derivative" is an immune-derived moiety, i.e., a molecule that is derived from an antibody. This includes any antibody (Ab) or immunoglobulin (Ig), and refers to any form of a peptide, polypeptide derived from, modeled after or encoded by, an immunoglobulin gene, or a fragment of such peptide or polypeptide that is capable of binding an antigen or epitope. This comprehends, for example, antibody variants, antibody fragments, chimeric antibodies, humanized antibodies, multivalent antibodies, antibody conjugates and the like, which retain a desired level of binding activity for antigen.

As used herein, "antibody fragment" refers to a portion of an intact antibody that includes the antigen binding site or variable regions of an intact antibody, wherein the portion can be free of the constant heavy chain domains (e.g., CH2, CH3, and CH4) of the Fc region of the intact antibody. Alternatively, portions of the constant heavy chain domains (e.g., CH2, CH3, and CH4) can be included in the "antibody fragment". Antibody fragments retain antigen-binding and include Fab, Fab', F(ab')$_2$, Fd, and Fv fragments; diabodies; triabodies; single-chain antibody molecules (sc-Fv); minibodies, nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. By way of example, a Fab fragment also contains the constant domain of a light chain and the first constant domain (CH1) of a heavy chain. "Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

An "antibody variant" refers herein to a molecule which differs in amino acid sequence from the amino acid sequence of a native or parent antibody that is directed to the same antigen by virtue of addition, deletion and/or substitution of one or more amino acid residue(s) in the antibody sequence and which retains at least one desired activity of the parent anti-binding antibody. Desired activities can include the ability to bind the antigen specifically, the ability to inhibit proliferation in vitro, the ability to inhibit angiogenesis in vivo, and the ability to alter cytokine profile in vitro. The amino acid change(s) in an antibody variant may be within a variable region or a constant region of a light chain and/or a heavy chain, including in the Fc region, the Fab region, the $CH_1$ domain, the $CH_2$ domain, the $CH_3$ domain, and the hinge region. In one embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 50% amino acid sequence identity with the parent antibody heavy or light chain variable domain sequences, more preferably at least 65%, more preferably at 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind LPA and preferably has desired activities which are superior to those of the parent antibody. For example, the variant may have a stronger binding affinity, enhanced ability to reduce angiogenesis and/or halt tumor progression. To analyze such desired properties (for example les immunogenic, longer half-life, enhanced stability, enhanced potency), one should compare a Fab form of the variant to a Fab form of the parent antibody or a full length form of the variant to a full length form of the parent antibody, for example, since it has been found that the format of the anti-sphingolipid antibody impacts its activity in the biological activity assays disclosed herein. The variant antibody of particular interest herein can be one which displays at least about 10 fold, preferably at least about % 5, 25, 59, or more of at least one desired activity. The preferred variant is one that has superior biophysical properties as measured in vitro or superior activities biological as measured in vitro or in vivo when compared to the parent antibody.

An "anti-LPA agent" refers to any therapeutic agent that binds LPA, and includes antibodies, antibody variants, antibody-derived molecules or non-antibody-derived moieties that bind LPA and its variants.

An "anti-LPA antibody" or an "immune-derived moiety reactive against LPA" refers to any antibody or antibody-derived molecule that binds LPA. As will be understood from these definitions, antibodies or immune-derived moieties may be polyclonal or monoclonal and may be generated through a variety of means, and/or may be isolated from an animal, including a human subject.

An "anti-S1P agent" refers to any therapeutic agent that binds S1P, and includes antibodies, antibody variants, antibody-derived molecules or non-antibody-derived moieties that bind LPA and its variants.

An "anti-S1P antibody" or an "immune-derived moiety reactive against S1P" refers to any antibody or antibody-derived molecule that binds S1P. As will be understood from these definitions, antibodies or immune-derived moieties may be polyclonal or monoclonal and may be generated through a variety of means, and/or may be isolated from an animal, including a human subject.

A "bioactive lipid" refers to a lipid signaling molecule. Bioactive lipids are distinguished from structural lipids (e.g., membrane-bound phospholipids) in that they mediate extracellular and/or intracellular signaling and thus are involved in controlling the function of many types of cells by modulating differentiation, migration, proliferation, secretion, survival, and other processes. In vivo, bioactive lipids can be found in extracellular fluids, where they can be complexed with other molecules, for example serum proteins such as albumin and lipoproteins, or in "free" form, i.e., not complexed with another molecule species. As extracellular mediators, some bioactive lipids alter cell signaling by activating membrane-bound ion channels or GPCRs or enzymes or factors that, in turn, activate complex signaling systems that result in changes in cell function or survival. As intracellular mediators, bioactive lipids can exert their actions by directly interacting with intracellular components such as enzymes, ion channels or structural elements such as actin.

Examples of bioactive lipids include sphingolipids such as ceramide, ceramide-1-phosphate (C1P), sphingosine, sphinganine, sphingosylphosphorylcholine (SPC) and sphingosine-1-phosphate (S1P). Sphingolipids and their derivatives and metabolites are characterized by a sphingoid backbone (derived from sphingomyelin). Sphingolipids and their derivatives and metabolites represent a group of extracellular and intracellular signaling molecules with pleiotropic effects on important cellular processes. They include sulfatides, gangliosides and cerebrosides. Other bioactive lipids are characterized by a glycerol-based backbone; for example, lysophospholipids such as lysophosphatidyl choline (LPC) and various lysophosphatidic acids (LPA), as well as phosphatidylinositol (PI), phosphatidylethanolamine (PEA), phosphatidic acid, platelet activating factor (PAF), cardiolipin, phosphatidylglycerol (PG) and diacylglyceride (DG). Yet other bioactive lipids are derived from arachidonic acid; these include the eicosanoids (including the eicosanoid metabolites such as the HETEs, cannabinoids, leukotrienes, prostaglandins, lipoxins, epoxyeicosatrienoic acids, and isoeicosanoids), non-eicosanoid cannabinoid mediators. Other bioactive lipids, including other phospholipids and their derivatives, may also be used according to the instant invention.

In some embodiments of the invention it may be preferable to target glycerol-based bioactive lipids (those having a glycerol-derived backbone, such as the LPAs) for antibody production, as opposed to sphingosine-based bioactive lipids (those having a sphingoid backbone, such as sphingosine and S1P). In other embodiments it may be desired to target arachidonic acid-derived bioactive lipids for antibody generation, and in other embodiments arachidonic acid-derived and glycerol-derived bioactive lipids but not sphingoid-derived bioactive lipids are preferred. Together the arachidonic acid-derived and glycerol-derived bioactive lipids may be referred to in the context of this invention as "non-sphingoid bioactive lipids."

Specifically excluded from the class of bioactive lipids according to the invention are phosphatidylcholine and phosphatidylserine, as well as their metabolites and derivatives that function primarily as structural members of the inner and/or outer leaflet of cellular membranes.

The term "biologically active," in the context of an antibody or antibody fragment or variant, refers to an antibody or antibody fragment or antibody variant that is capable of binding the desired epitope and in some ways exerting a biologic effect. Biological effects include, but are not limited to, the modulation of a growth signal, the modulation of an anti-apoptotic signal, the modulation of an apoptotic signal, the modulation of the effector function cascade, and modulation of other ligand interactions.

A "biomarker" is a specific biochemical in the body which has a particular molecular feature that makes it useful for measuring the progress of disease or the effects of treatment. For example, S1P is a biomarker for certain hyperproliferative and/or cardiovascular conditions.

The term "cardiotherapeutic agent" refers to an agent that is therapeutic to diseases and diseases caused by or associated with cardiac and myocardial diseases and disorders.

"Cardiovascular therapy" encompasses cardiac therapy (treatment of myocardial ischemia and/or heart failure) as well as the prevention and/or treatment of other diseases associated with the cardiovascular system, such as heart disease. The term "heart disease" encompasses any type of disease, disorder, trauma or surgical treatment that involves the heart or myocardial tissue. Of particular interest are conditions associated with tissue remodeling. The term "cardiotherapeutic agent" refers to an agent that is therapeutic to diseases and diseases caused by or associated with cardiac and myocardial diseases and disorders.

A "carrier" refers to a moiety adapted for conjugation to a hapten, thereby rendering the hapten immunogenic. A representative, non-limiting class of carriers is proteins, examples of which include albumin, keyhole limpet hemocyanin, hemaglutanin, tetanus, and diptheria toxoid. Other classes and examples of carriers suitable for use in accordance with the invention are known in the art. These, as well as later discovered or invented naturally occurring or synthetic carriers, can be adapted for application in accordance with the invention.

As used herein, the expressions "cell," "cell line," and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Cerebrovascular therapy" refers to therapy directed to the prevention and/or treatment of diseases and disorders associated with cerebral ischemia and/or hypoxia. Of particular interest is cerebral ischemia and/or hypoxia resulting from global ischemia resulting from a heart disease, including without limitation heart failure.

The term "chemotherapeutic agent" means anti-cancer and other anti-hyperproliferative agents. Thus chemotherapeutic agents are a subset of therapeutic agents in general. Chemotherapeutic agents include, but are not limited to: DNA damaging agents and agents that inhibit DNA synthesis: anthracyclines (doxorubicin, donorubicin, epirubicin), alkylating agents (bendamustine, busulfan, carboplatin, carmustine, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diammine-dichloroplatinum), and topoisomerase inhibitors (Camptosar); antimetabolites such as capecitabine, chlorodeoxyadenosine, cytarabine (and its activated form, ara-CMP), cytosine arabinoside, dacabazine, floxuridine, fludarabine, 5-fluorouracil, 5-DFUR, gemcitabine, hydroxyurea, 6-mercaptopurine, methotrexate, pentostatin, trimetrexate, 6-thioguanine); anti-angiogenics (bevacizumab, thalidomide, sunitinib, lenalidomide, TNP-470, 2-methoxyestradiol, ranibizumab, sorafenib, erlotinib, bortezomib, pegaptanib, endostatin); vascular disrupting agents (flavonoids/flavones, DMXAA, combretastatin derivatives such as CA4DP, ZD6126, AVE8062A, etc.); biologics such as antibodies (Herceptin, Avastin, Panorex, Rituxin, Zevalin, Mylotarg, Campath, Bexxar, Erbitux); endocrine therapy: aromatase inhibitors (4-hydroandrostendione, exemestane, aminoglutehimide, anastrazole, letozole), anti-estrogens (Tamoxifen, Toremifine, Raoxifene, Faslodex), steroids such as dexamethasone; immuno-modulators: cytokines such as IFN-beta and IL2), inhibitors to integrins, other adhesion proteins and matrix metalloproteinases); histone deacetylase inhibitors like suberoylanilide hydroxamic acid; inhibitors of signal transduction such as inhibitors of tyrosine kinases like imatinib (Gleevec); inhibitors of heat shock proteins like 17-N-allylamino-17-demethoxygeldanamycin; retinoids such as all trans retinoic acid; inhibitors of growth factor receptors or the growth factors themselves; anti-mitotic compounds and/or tubulin-depolymerizing agents such as the taxoids (paclitaxel, docetaxel, taxotere, BAY 59-8862), navelbine, vinblastine, vincristine, vindesine and vinorelbine; anti-inflammatories such as COX inhibitors and cell cycle regulators, e.g., check point regulators and telomerase inhibitors.

The term "chimeric" antibody (or immunoglobulin) refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., infra; Morrison et al., Proc. Natl. Acad. Sci. U.S.A., vol. 81:6851 (1984)).

The term "combination therapy" refers to a therapeutic regimen that involves the provision of at least two distinct therapies to achieve an indicated therapeutic effect. For example, a combination therapy may involve the administration of two or more chemically distinct active ingredients, for example, a fast-acting chemotherapeutic agent and an anti-lipid antibody, or two different antibodies. Alternatively, a combination therapy may involve the administration of an anti-lipid antibody together with the delivery of another treatment, such as radiation therapy and/or surgery. Further, a combination therapy may involve administration of an anti-lipid antibody together with one or more other biological agents (e.g., anti-VEGF, TGFβ, PDGF, or bFGF agent), chemotherapeutic agents and another treatment such as radiation and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-LPA antibody, alone or in conjunction with one or more chemotherapeutic agents are combined with, for example, radiation and/or surgery, the drug(s) may be delivered before or after surgery or radiation treatment.

The term "constant domain" refers to the C-terminal region of an antibody heavy or light chain. Generally, the constant domains are not directly involved in the binding properties of an antibody molecule to an antigen, but exhibit various effector functions, such as participation of the antibody in anti-body-dependent cellular toxicity. Here, "effector functions" refer to the different physiological effects of antibodies (e.g., opsonization, cell lysis, mast cell, basophil and eosinophil degranulation, and other processes) mediated by the recruitment of immune cells by the molecular interaction between the Fc domain and proteins of the immune system. The isotype of the heavy chain determines the functional properties of the antibody. Their distinctive functional properties are conferred by the carboxy-terminal portions of the heavy chains, where they are not associated with light chains.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A "derivatized bioactive lipid" is a bioactive lipid, e.g., LPA, which has a polar head group and at least one hydrocarbon chain, wherein a carbon atom within the hydrocarbon chain is derivatized with a pendant reactive group [e.g., a sulfhydryl (thiol) group, a carboxylic acid group, a cyano group, an ester, a hydroxy group, an alkene, an alkyne, an acid chloride group or a halogen atom] that may or may not be protected. This derivatization serves to activate the bioactive lipid for reaction with a molecule, e.g., for conjugation to a carrier.

A "derivatized bioactive lipid conjugate" refers to a derivatized bioactive lipid that is covalently conjugated to a carrier. The carrier may be a protein molecule or may be a moiety such as polyethylene glycol, colloidal gold, adjuvants or silicone beads. A derivatized bioactive lipid conjugate may be used as an immunogen for generating an antibody response according to the instant invention, and the same or a different bioactive lipid conjugate may be used as a detection reagent for detecting the antibody thus produced. In some embodiments the derivatized bioactive lipid conjugate is attached to a solid support when used for detection.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

"Effective concentration" refers to the absolute, relative, and/or available concentration and/or activity, for example of certain undesired bioactive lipids. In other words, the effective concentration of a bioactive lipid is the amount of lipid available, and able, to perform its biological function. In the present invention, an immune-derived moiety such as, for example, a monoclonal antibody directed to a bioactive lipid (such as, for example, C1P) is able to reduce the effective concentration of the lipid by binding to the lipid and rendering it unable to perform its biological function. In this example, the lipid itself is still present (it is not degraded by the antibody, in other words) but can no longer bind its receptor or other targets to cause a downstream effect, so "effective concentration" rather than absolute concentration is the appropriate measurement. Methods and assays exist for directly and/or indirectly measuring the effective concentration of bioactive lipids.

An "epitope" or "antigenic determinant" refers to that portion of an antigen that reacts with an antibody antigen-binding portion derived from an antibody.

The term "expression cassette" refers to a nucleotide molecule capable of affecting expression of a structural gene (i.e., a protein coding sequence, such as an antibody of the invention) in a host compatible with such sequences. Expression cassettes include at least a promoter operably linked with the polypeptide-coding sequence, and, optionally, with other sequences, e.g., transcription termination signals. Additional regulatory elements necessary or helpful in effecting expression may also be used, e.g., enhancers. Thus, expression cassettes include plasmids, expression vectors, recombinant viruses, any form of recombinant "naked DNA" vector, and the like.

A "fully human antibody" can refer to an antibody produced in a genetically engineered (i.e., transgenic) mouse (e.g. from Medarex) that, when presented with an immunogen, can produce a human antibody that does not necessarily require CDR grafting. These antibodies are fully human (100% human protein sequences) from animals such as mice in which the non-human antibody genes are suppressed and replaced with human antibody gene expression. The applicants believe that antibodies could be generated against bioactive lipids when presented to these genetically engineered mice or other animals who might be able to produce human frameworks for the relevant CDRs.

A "hapten" is a substance that is non-immunogenic but can react with an antibody or antigen-binding portion derived from an antibody. In other words, haptens have the property of antigenicity but not immunogenicity. A hapten is generally a small molecule that can, under most circumstances, elicit an immune response (i.e., act as an antigen) only when attached to a carrier, for example, a protein, polyethylene glycol (PEG), colloidal gold, silicone beads, or the like. The carrier may be one that also does not elicit an immune response by itself. A representative, non-limiting class of hapten molecules is proteins, examples of which include albumin, keyhole limpet hemocyanin, hemaglutanin, tetanus, and diphtheria toxoid. Other classes and examples of hapten molecules are known in the art. These, as well as later discovered or invented naturally occurring or synthetic haptens, can be adapted for application in accordance with the invention.

The term "heteroconjugate antibody" can refer to two covalently joined antibodies. Such antibodies can be prepared using known methods in synthetic protein chemistry, including using crosslinking agents. As used herein, the term "conjugate" refers to molecules formed by the covalent attachment of one or more antibody fragment(s) or binding moieties to one or more polymer molecule(s).

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g., murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. In some instances, framework region (FR) residues of the human immunoglobulin are replaced by corresponding non-human residues.

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin. See, e.g., Cabilly, et al., U.S. Pat. No. 4,816,567; Cabilly, et al., European Patent No. 0,125,023 B1; Boss, et al., U.S. Pat. No. 4,816,397; Boss, et al., European Patent No. 0,120,694 B1; Neuberger, et al., WO 86/01533; Neuberger, et al., European Patent No. 0,194, 276 B1; Winter, U.S. Pat. No. 5,225,539; Winter, European Patent No. 0,239,400 B1; Padlan, et al., European Patent Application No. 0,519,596 A1; Queen, et al. (1989), Proc. Nat'l Acad. Sci. USA, vol. 86:10029-10033). For further details, see Jones et al., Nature 321:522-525 (1986); Reichmann et al., Nature 332:323-329 (1988); and Presta, Curr. Op. Struct. Biol. 2:593-596 (1992) and Hansen, WO2006105062.

The term "hyperproliferative disorder" refers to diseases and disorders associated with, the uncontrolled proliferation of cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, age-related macular degeneration and various retinopathies, as well as the proliferation of endothelial cells and smooth muscle cells that cause restenosis as a consequence of stenting in the treatment of atherosclerosis. Hyperproliferative disorders involving fibroblasts (i.e., fibrogenesis) include but are not limited to disorders of excessive scarring (i.e., fibrosis) such as age-related macular degeneration, cardiac remodeling and failure associated with myocardial infarction, excessive wound healing such as commonly occurs as a consequence of surgery or injury, keloids, and fibroid tumors and stenting.

An "immune-derived moiety" includes any antibody (Ab) or immunoglobulin (Ig), and refers to any form of a peptide, polypeptide derived from, modeled after or encoded by, an immunoglobulin gene, or a fragment of such peptide or polypeptide that is capable of binding an antigen or epitope (see, e.g., Immunobiology, 5th Edition, Janeway, Travers, Walport, Shlomchiked. (editors), Garland Publishing (2001)). In the present invention, the antigen is a lipid molecule, such as a bioactive lipid molecule.

An "immunogen" is a molecule capable of inducing a specific immune response, particularly an antibody response in an animal to whom the immunogen has been administered. In the instant invention, the immunogen is a derivatized bioactive lipid conjugated to a carrier, i.e., a "derivatized bioactive lipid conjugate". The derivatized bioactive lipid conjugate used as the immunogen may be used as capture material for detection of the antibody generated in response to the immunogen. Thus the immunogen may also be used as a detection reagent. Alternatively, the derivatized bioactive lipid conjugate used as capture material may have a different linker and/or carrier moiety from that in the immunogen.

The phrase "in silico" refers to computer simulations that model natural or laboratory processes To "inhibit," particularly in the context of a biological phenomenon, means to decrease, suppress or delay. For example, a treatment yielding "inhibition of tumorigenesis" may mean that tumors do not form at all, or that they form more slowly, or are fewer in number than in the untreated control.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition, such as one that is conjugated directly or indirectly to the antibody. The label may itself be detectable by itself (e.g., radioisotope labels or fluorescent labels) or, in the case of an enzymatic label, may catalyze chemical alteration of a substrate compound or composition that is detectable.

A "ligand" is a substance that is able to bind to and form a complex with a biomolecule to serve a biological purpose. Thus an antigen may be described as a ligand of the antibody to which it binds.

A "liposome" is a small vesicle composed of various types of lipids, phospholipids and/or surfactant that is useful for delivery of a drug (such as the anti-sphingolipid antibodies disclosed herein and, optionally, a chemotherapeutic agent) to a mammal. The components of the liposome are commonly arranged in a bilayer formation, similar to the lipid arrangement of biological membranes. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

In the context of this invention, a "liquid composition" refers to one that, in its filled and finished form as provided from a manufacturer to an end user (e.g., a doctor or nurse), is a liquid or solution, as opposed to a solid. Here, "solid" refers to compositions that are not liquids or solutions. For example, solids include dried compositions prepared by lyophilization, freeze-drying, precipitation, and similar procedures.

The expression "linear antibodies" when used throughout this application refers to the antibodies described in Zapata et al. Protein Eng. 8(10):1057-1062 (1995). Briefly, these antibodies comprise a pair of tandem Fd segments ($V_H$-$C_H$1-$V_H$-$C_H$1) that form a pair of antigen binding regions. Linear antibodies can be bispecific or monospecific.

The term "metabolites" refers to compounds from which LPAs are made, as well as those that result from the degradation of LPAs; that is, compounds that are involved in the lysophospholipid metabolic pathways. The term "metabolic precursors" may be used to refer to compounds from which sphingolipids are made.

The term "monoclonal antibody" (mAb) as used herein refers to an antibody obtained from a population of substantially homogeneous antibodies, or to said population of antibodies. The individual antibodies comprising the population are essentially identical, except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example, or by other methods known in the art. The monoclonal antibodies herein specifically include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Monotherapy" refers to a treatment regimen based on the delivery of one therapeutically effective compound, whether administered as a single dose or several doses over time.

The term "multispecific antibody" can refer to an antibody, or a monoclonal antibody, having binding properties for at least two different epitopes. In one embodiment, the epitopes are from the same antigen. In another embodiment, the epitopes are from two or more different antigens. Methods for making multispecific antibodies are known in the art. Multispecific antibodies include bispecific antibodies (having binding properties for two epitopes), trispecific antibodies (three epitopes) and so on. For example, multispecific antibodies can be produced recombinantly using the co-expression of two or more immunoglobulin heavy chain/light chain pairs. Alternatively, multispecific antibodies can be prepared using chemical linkage. One of skill can produce multispecific antibodies using these or other methods as may be known in the art. Multispecific antibodies include multispecific antibody fragments. One example of a multispecific (in this case, bispecific) antibody comprehended by this invention is an antibody having binding properties for an S1P epitope and a C1P epitope, which thus is able to recognize and bind to both S1P and C1P. Another example of a bispecific antibody comprehended by this invention is an antibody having binding properties for an epitope from a bioactive lipid and an epitope from a cell surface antigen. Thus the antibody is able to recognize and bind the bioactive lipid and is able to recognize and bind to cells, e.g., for targeting purposes.

"Neoplasia" or "cancer" refers to abnormal and uncontrolled cell growth. A "neoplasm", or tumor or cancer, is an abnormal, unregulated, and disorganized proliferation of cell growth, and is generally referred to as cancer. A neoplasm may be benign or malignant. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The "parent" antibody herein is one that is encoded by an amino acid sequence used for the preparation of the variant. The parent antibody may be a native antibody or may already be a variant, e.g., a chimeric antibody. For example, the parent antibody may be a humanized or human antibody.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the non-patentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

The term "pharmaceutically acceptable salt" refers to a salt, such as used in formulation, which retains the biological effectiveness and properties of the agents and compounds of this invention and which are is biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts (see Berge, et al. (1977) J. Pharm. Sci., vol. 66, 1-19).

A "plurality" means more than one.

The term "promoter" includes all sequences capable of driving transcription of a coding sequence in a cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. Transcriptional regulatory regions suitable for use in the present invention include but are not limited to the human cytomegalovirus (CMV) immediate-early enhancer/promoter, the SV40 early enhancer/promoter, the *E. coli* lac or trp promoters, and other promoters known to control expression of genes in prokaryotic or eukaryotic cells or their viruses.

The term "recombinant DNA" refers to nucleic acids and gene products expressed therefrom that have been engineered, created, or modified by man. "Recombinant" polypeptides or proteins are polypeptides or proteins produced by recombinant DNA techniques, for example, from cells transformed by an exogenous DNA construct encoding the desired polypeptide or protein. "Synthetic" polypeptides or proteins are those prepared by chemical synthesis.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, non-reacted chemicals, proteins, carbohydrates, lipids, and unbound molecules.

By "solid phase" is meant a non-aqueous matrix such as one to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

The term "species" is used herein in various contexts, e.g., a particular species of chemotherapeutic agent. In each context, the term refers to a population of chemically indistinct molecules of the sort referred in the particular context.

The term "specific" or "specificity" in the context of antibody-antigen interactions refers to the selective, non-random interaction between an antibody and its target epitope. Here, the term "antigen" refers to a molecule that is recognized and bound by an antibody molecule or other immune-derived moiety. The specific portion of an antigen that is bound by an antibody is termed the "epitope". This interaction depends on the presence of structural, hydrophobic/hydrophilic, and/or electrostatic features that allow appropriate chemical or molecular interactions between the molecules. Thus an antibody is commonly said to "bind" (or "specifically bind") or be "reactive with" (or "specifically reactive with), or, equivalently, "reactive against" (or "specifically reactive against") the epitope of its target antigen. Antibodies are commonly described in the art as being "against" or "to" their antigens as shorthand for antibody binding to the antigen. Thus an "antibody that binds C1P," an "antibody reactive against C1P," an "antibody reactive with C1P," an "antibody to C1P" and an "anti-C1P antibody" all have the same meaning in the art. Antibody molecules can be tested for specificity of binding by comparing binding to the desired antigen to binding to unrelated antigen or analogue antigen or antigen mixture under a given set of conditions. Preferably, an antibody according to the invention will lack significant binding to unrelated antigens, or even analogs of the target antigen. "Specifically associate" and "specific association" and the like refer to a specific, non-random interaction between two molecules, which interaction depends on the presence of structural, hydrophobic/hydrophilic, and/or electrostatic features that allow appropriate chemical or molecular interactions between the molecules.

The term "sphingolipid" as used herein refers to the class of compounds in the art known as sphingolipids, including, but not limited to the following compounds (see http//www.lipidmaps.org for chemical formulas, structural information, etc. for the corresponding compounds):

Sphingoid bases [SP01]
Sphing-4-enines (Sphingosines) [SP0101]
Sphinganines [SP0102]
4-Hydroxysphinganines (Phytosphingosines) [SP0103]
Sphingoid base homologs and variants [SP0104]
Sphingoid base 1-phosphates [SP0105]
Lysosphingomyelins and lysoglycosphingolipids [SP0106]
N-methylated sphingoid bases [SP0107]
Sphingoid base analogs [SP0108]
Ceramides [SP02]
N-acylsphingosines (ceramides) [SP0201]
N-acylsphinganines (dihydroceramides) [SP0202]
N-acyl-4-hydroxysphinganines (phytoceramides) [SP0203]
Acylceramides [SP0204]
Ceramide 1-phosphates [SP0205]
Phosphosphingolipids [SP03]
Ceramide phosphocholines (sphingomyelins) [SP0301]
Ceramide phosphoethanolamines [SP0302]
Ceramide phosphoinositols [SP0303]
Phosphonosphingolipids [SP04]
Neutral glycosphingolipids [SP05]
Simple Glc series (GlcCer, LacCer, etc) [SP0501]
GalNAcb1-3Gala1-4Galb1-4Glc- (Globo series) [SP0502]
GalNAcb1-4Galb1-4Glc- (Ganglio series) [SP0503]
Galb1-3GlcNAcb1-3Galb1-4Glc- (Lacto series) [SP0504]
Galb1-4GlcNAcb1-3Galb1-4Glc- (Neolacto series) [SP0505]
GalNAcb1-3Gala1-3Galb1-4Glc- (Isoglobo series) [SP0506]
GlcNAcb1-2Mana1-3Manb1-4Glc- (Mollu series) [SP0507]
GalNAcb1-4GlcNAcb1-3Manb1-4Glc- (Arthro series) [SP0508]
Gal- (Gala series) [SP0509]
Other [SP0510]
Acidic glycosphingolipids [SP06]
Gangliosides [SP0601]
Sulfoglycosphingolipids (sulfatides) [SP0602]
Glucuronosphingolipids [SP0603]
Phosphoglycosphingolipids [SP0604]
Other [SP0600]
Basic glycosphingolipids [SP07]
Amphoteric glycosphingolipids [SP08]
Arsenosphingolipids [SP09]

The present invention relates to anti-lipid agents, including anti-sphingolipid antibodies, that are useful for treating or preventing hyperproliferative disorders such as cancer and cardiovascular or cerebrovascular diseases and disorders and various ocular disorders, as described in greater detail below. The invention relates, among others, to antibodies to S1P and its variants including but are not limited to sphingosine-1-phosphate [sphingene-1-phosphate; D-erythro-sphingosine-1-phosphate; sphing-4-enine-1-phosphate; (E,2S,3R)-2-amino-3-hydroxy-octadec-4-enoxy]phosphonic acid (AS 26993-30-6), DHS1P is defined as dihydrosphingosine-1-phosphate [sphinganine-1-phosphate; [(2S,3R)-2-amino-3- hydroxy-octadecoxy]phosphonic acid; D-Erythro-dihydro-D-sphingosine-1-phosphate (CAS19794-97-9]; SPC is sphingosylphosphoryl choline, lysosphingomyelin, sphingosylphosphocholine, sphingosine phosphorylcholine, ethanaminium; 2-((((2-amino-3-hydroxy-4-octadecenyl)oxy)hydroxyphosphinyl)oxy)-N,N,N-trimethyl-, chloride, (R—(R*,S*-(E))), 2-[[(E,2R,3S)-2-amino-3-hydroxy-octadec-4-enoxy]-hydroxy-phosphoryl]oxyethyl1-trimethyl-azanium chloride (CAS 10216-23-6).

The term "sphingolipid metabolite" refers to a compound from which a sphingolipid is made, as well as a that results from the degradation of a particular sphingolipid. In other words, a "sphingolipid metabolite" is a compound that is involved in the sphingolipid metabolic pathways. Metabolites include metabolic precursors and metabolic products. The term "metabolic precursors" refers to compounds from which sphingolipids are made. Metabolic precursors of particular interest include but are not limited to SPC, sphingomyelin, dihydrosphingosine, dihydroceramide, and 3-ketosphinganine. The term "metabolic products" refers to compounds that result from the degradation of sphingolipids, such as phosphorylcholine (e.g., phosphocholine, choline phosphate), fatty acids, including free fatty acids, and hexadecanal (e.g., palmitaldehyde).

Herein, "stable" refers to an interaction between two molecules (e.g., a peptide and a TLR molecule) that is sufficiently stable such that the molecules can be maintained for the desired purpose or manipulation. For example, a "stable" interaction between a peptide and a TLR molecule refers to one wherein the peptide becomes and remains associated with a TLR molecule for a period sufficient to achieve the desired effect.

A "subject" or "patient" refers to an animal in need of treatment that can be effected by molecules of the invention Animals that can be treated in accordance with the invention include vertebrates, with mammals such as bovine, canine, equine, feline, ovine, porcine, and primate (including humans and non-human primates) animals being particularly preferred examples.

A "surrogate marker" refers to laboratory measurement of biological activity within the body that indirectly indicates the effect of treatment on disease state. Examples of surrogate markers for hyperproliferative and/or cardiovascular conditions include SPHK and/or S1PRs.

A "therapeutic agent" refers to a drug or compound that is intended to provide a therapeutic effect including, but not limited to: anti-inflammatory drugs including COX inhibitors and other NSAIDS, anti-angiogenic drugs, chemotherapeutic drugs as defined above, cardiovascular agents, immunomodulatory agents, agents that are used to treat neurodegenerative disorders, opthalmic drugs, anti-fibrotics, etc.

A "therapeutically effective amount" (or "effective amount") refers to an amount of an active ingredient, e.g., an agent according to the invention, sufficient to effect treatment when administered to a subject in need of such treatment. Accordingly, what constitutes a therapeutically effective amount of a composition according to the invention may be readily determined by one of ordinary skill in the art. In the context of cancer therapy, a "therapeutically effective amount" is one that produces an objectively measured change in one or more parameters associated with cancer cell survival or metabolism, including an increase or decrease in the expression of one or more genes correlated with the particular cancer, reduction in tumor burden, cancer cell lysis, the detection of one or more cancer cell death markers in a biological sample (e.g., a biopsy and an aliquot of a bodily fluid such as whole blood, plasma, serum, urine, etc.), induction of induction apoptosis or other cell death pathways, etc. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (i.e., a therapeutic regimen that employs only one chemical entity as the active ingredient).

The compositions of the invention are used in methods of bioactive lipid-based therapy. As used herein, the terms "therapy" and "therapeutic" encompasses the full spectrum of prevention and/or treatments for a disease, disorder or physical trauma. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of at least one symptom of a disease or disorder being treated; or may act to minimize the time required, the occurrence or extent of any discomfort or pain, or physical limitations associated with recuperation from a disease, disorder or physical trauma; or may be used as an adjuvant to other therapies and treatments.

The term "treatment" or "treating" means any treatment of a disease or disorder, including preventing or protecting against the disease or disorder (that is, causing the clinical symptoms not to develop); inhibiting the disease or disorder (i.e., arresting, delaying or suppressing the development of clinical symptoms; and/or relieving the disease or disorder (i.e., causing the regression of clinical symptoms). As will be appreciated, it is not always possible to distinguish between "preventing" and "suppressing" a disease or disorder because the ultimate inductive event or events may be unknown or latent. Those "in need of treatment" include those already with the disorder as well as those in which the disorder is to be prevented. Accordingly, the term "prophylaxis" will be understood to constitute a type of "treatment" that encompasses both "preventing" and "suppressing". The term "protection" thus includes "prophylaxis".

The term "therapeutic regimen" means any treatment of a disease or disorder using chemotherapeutic and cytotoxic agents, radiation therapy, surgery, gene therapy, DNA vaccines and therapy, siRNA therapy, anti-angiogenic therapy, immunotherapy, bone marrow transplants, aptamers and other biologics such as antibodies and antibody variants, receptor decoys and other protein-based therapeutics.

The "variable" region of an antibody comprises framework and complementarity determining regions (CDRs, otherwise known as hypervariable regions). The variability is not evenly distributed throughout the variable domains of antibodies. It is concentrated in six CDR segments, three in each of the light chain and the heavy chain variable domains. The more highly conserved portions of variable domains are called the framework region (FR). The variable domains of native heavy and light chains each comprise four FRs (FR1, FR2, FR3 and FR4, respectively), largely adopting β-sheet configuration, connected by three hypervariable regions, which form loops connecting, and in some cases forming part of, the beta-sheet structure. The term "hypervariable region" when used herein refers to the amino acid residues of an antibody which are responsible for antigen binding. The hypervariable region comprises amino acid residues from a "complementarity determining region" or "CDR" (for example residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (for example residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

It should be noted that, in the art, more than one system for numbering of amino acid residues is commonly used. The CDRs above are described and numbered according to the Kabat numbering scheme (Kabat et al., Sequences of Proteins of Immunological Interest, 5th Ed. Public Health Service, National Institutes of Health, Bethesda, Md. (1991)) but sequential numbering may also be used. Sequential and Kabat numbering are identical for the entire LT1009 light chain, and up to position 52 in the LT1009 heavy chain. In the heavy chain (VH), according to Kabat numbering there is a single residue insertion after position 52, a three-residue insertion after position 82 and a four residue insertion after position 100. Thus residues may at times be seen to be numbered 52A, 100A, 100C etc. to reflect these insertions according to the Kabat system.

The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

A "vector" or "plasmid" or "expression vector" refers to a nucleic acid that can be maintained transiently or stably in a cell to effect expression of one or more recombinant genes. A vector can comprise nucleic acid, alone or complexed with other compounds. A vector optionally comprises viral or bacterial nucleic acids and/or proteins, and/or membranes. Vectors include, but are not limited to, replicons (e.g., RNA replicons, bacteriophages) to which fragments of DNA may be attached and become replicated. Thus, vectors include, but are not limited to, RNA, autonomous self-replicating circular or linear DNA or RNA and include both the expression and non-expression plasmids. Plasmids can be commercially available, publicly available on an unrestricted basis, or can be constructed from available plasmids as reported with published protocols. In addition, the expression vectors may also contain a gene to provide a phenotypic trait for selection of transformed host cells such as dihydrofolate reductase or neomycin resistance for eukaryotic cell culture, or such as tetracycline or ampicillin resistance in *E. coli*.

SUMMARY OF THE INVENTION

The present invention provides patentable crystalline forms of an anti-lipid antibody or fragment thereof, which may further comprise a lipid ligand of said antibody and/or salts, metals, and/or co-factors. Methods for making such crystals are provided. The lipid may be a bioactive lipid, such as a sphingolipid including S1P. X-ray coordinates of one such crystal are provided, as are methods of using this information in antibody design or optimization.

Methods for designing a humanized antibody to a lipid are provided, which may be performed in silico. These methods may result in enhanced binding affinity of an antibody to its original target lipid, or may be intended to alter binding specificity.

These and other aspects and embodiments of the invention are discussed in greater detail in the sections that follow. The foregoing and other aspects of the invention will become more apparent from the following detailed description, accompanying drawings, and the claims. Although methods and materials similar or equivalent to those described herein can be used in the practice or testing of the present invention, suitable methods and materials are described below. In addition, the materials, methods, and examples below are illustrative only and not intended to be limiting.

BRIEF DESCRIPTION OF THE DRAWINGS

FIG. 1a shows the result of an SDS-PAGE analysis showing purity of the antibody Fab fragment and its separation from the Fc fragment contaminant. FIG. 1b is a photograph of a hanging drop containing Fab/S1P complex co-crystals viewed through the eyepiece of a stereomicroscope. FIG. 1c is a one-degree oscillation image of x-rays diffracted by the Fab/S1P crystals. Data were collected at 100K on an R-AxisIV++ image plate detector at the SDSU MXCF. FIG. 1d is a ribbon diagram structure depicting the antibody Fab/S1P complex crystal structure. The heavy chain is depicted in dark orange while the light chain is represented in light orange. S1P is in a stick representation with cpk atom coloring. The two grey spheres are $Ca^{2+}$ ions.

FIG. 2a is a bar graph showing the calculated concentrations of LT1009 variants and WT that produce half-maximal S1P binding using the direct-binding ELISA. FIG. 2b is a colored structure diagram showing the structure of the LT1009Fab/S1P complex. Atoms in the light (green) and heavy (blue) chains are drawn as spheres. The atoms in the amino acid side chains substituted in the LT1009 variants are colored magenta. The carbon, oxygen and phosphorus atoms of the bound S1P are colored grey, red, and yellow, respectively.

FIG. 3: Effect of metal chelators and mutations on S1P binding by LT1009. FIG. 3*a* is a ribbon model showing the interaction of S1P (gray) with key amino acid residues in the anti-S1P antibody. The calcium atoms are shown in purple. FIG. 3*b* is a line graph showing the negative effect of chelators EGTA and EDTA on LT1009-S1P binding. FIG. 3*c* is a line graph showing the effect of mutation of certain amino acid residues on LT1009-S1P binding. Numbering of amino acid residues is sequential.

FIG. 4: Conversion of antibody specificity. A single amino acid at position 50 of the light chain of LT1009 was mutated (GluL50 to GlnL50). The figure is a line graph showing that the resulting antibody variant has significantly higher affinity for LPA conjugate than for S1P conjugate, as shown by direct ELISA.

DETAILED DESCRIPTION OF THE INVENTION

1. Antibody Compounds

Antibody molecules or immunoglobulins are large glycoprotein molecules with a molecular weight of approximately 150 kDa, usually composed of two different kinds of polypeptide chain. The heavy chain (H) is approximately 50 kDa. The light chain (L), is approximately 25 kDa. Each immunoglobulin molecule usually consists of two heavy chains and two light chains. The two heavy chains are linked to each other by disulfide bonds, the number of which varies between the heavy chains of different immunoglobulin isotypes. Each light chain is linked to a heavy chain by one covalent disulfide bond. In any given naturally occurring antibody molecule, the two heavy chains and the two light chains are identical, harboring two identical antigen-binding sites, and are thus said to be divalent, i.e., having the capacity to bind simultaneously to two identical molecules.

Figure 1:
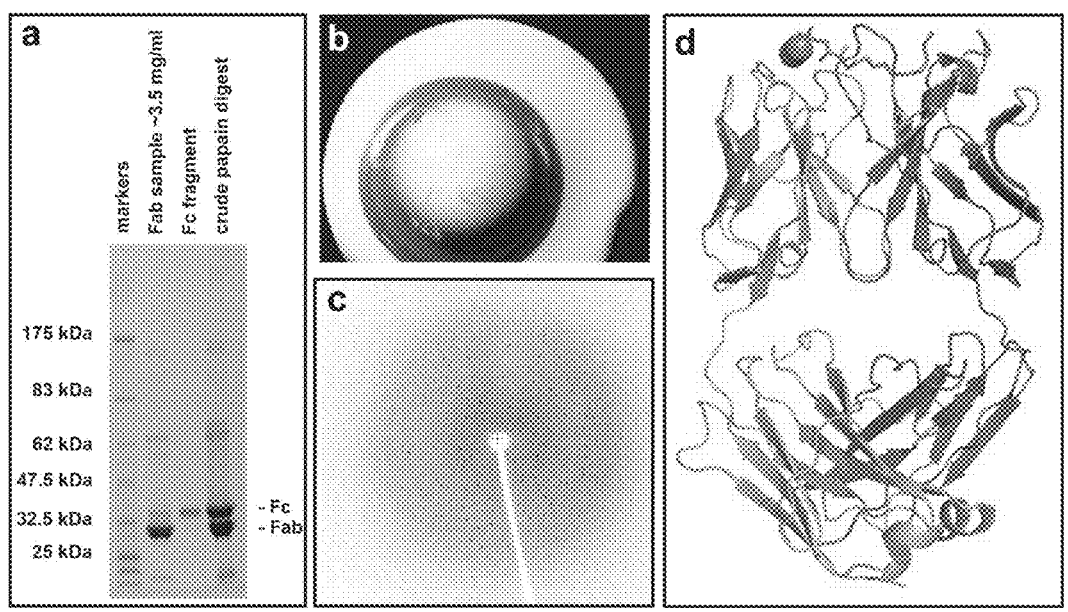
FIG. 1: Purification, crystallization, x-ray diffraction, and structure of the anti-S1P Fab/S1P complex.

The light chains of antibody molecules from any vertebrate species can be assigned to one of two clearly distinct types, kappa (k) and lambda (l), based on the amino acid sequences of their constant domains. The ratio of the two types of light chain varies from species to species. As a way of example, the average k to l ratio is 20:1 in mice, whereas in humans it is 2:1 and in cattle it is 1:20.

The heavy chains of antibody molecules from any vertebrate species can be assigned to one of five clearly distinct types, called isotypes, based on the amino acid sequences of their constant domains. Some isotypes have several subtypes. The five major classes of immunoglobulin are immunoglobulin M (IgM), immunoglobulin D (IgD), immunoglobulin G (IgG), immunoglobulin A (IgA), and immunoglobulin E (IgE). IgG is the most abundant isotype and has several subclasses (IgG1, 2, 3, and 4 in humans). The Fc fragment and hinge regions differ in antibodies of different isotypes, thus determining their functional properties. However, the overall organization of the domains is similar in all isotypes.

Sources of antibody are not limited to those exemplified herein (e.g., murine and humanized murine antibody). Antibodies may be raised in many species including mammalian species (for example, mouse, rat, camel, bovine, goat, horse, guinea pig, hamster, sheep and rabbit) and birds (duck, chicken). Antibodies raised may derive from a different species from the animal in which they are raised. For example, the XenoMouse™ (Abgenix, Inc., Fremont Calif.) produces fully human monoclonal antibodies. For certain purposes, native human antibodies, such as autoantibodies to S1P isolated from individuals who may show a titer of such S1P autoantibody may be used. Alternatively, a human antibody sequence library may be used to generate antibodies comprising a human sequence.

2. Antibody Applications

Therapeutic agents that alter the activity or concentration of one or more undesired bioactive lipids, or precursors or metabolites thereof, are therapeutically useful. These agents, including antibodies, act by changing the effective concentration, i.e., the absolute, relative, effective and/or available concentration and/or activities, of certain undesired bioactive lipids. Lowering the effective concentration of the bioactive lipid may be said to "neutralize" the target lipid or its undesired effects, including downstream effects. Here, "undesired" refers to a bioactive lipid that is unwanted due to its involvement in a disease process, for example, as a signaling molecule, or to an unwanted amount of a bioactive lipid which contributes to disease when present in excess.

Without wishing to be bound by any particular theory, it is believed that inappropriate concentrations of bioactive lipids, such as S1P and/or its metabolites or downstream effectors, may cause or contribute to the development of various diseases and disorders. As such, the compositions and methods can be used to treat these diseases and disorders, particularly by decreasing the effective in vivo concentration of a particular target lipid, for example, S1P or its variants. In particular, it is believed that the compositions and methods of the invention are useful in treating diseases characterized, at least in part, by aberrant neovascularization, angiogenesis, fibrogenesis, fibrosis, scarring, inflammation, and immune response.

Examples of diseases that may be treated with antibodies targeted to bioactive lipid are described below in applicant's pending patent applications and issued patents. See, for example. WO 2008/070344 (Attorney docket no. LPT-3010-PC) and WO 2008/055072 (Attorney docket no. LPT-3020-PC), which are hereby incorporated by reference in their entirety and for all purposes.

One way to control the amount of undesirable sphingolipids or other bioactive lipids in a patient is by providing a composition that comprises one or more humanized anti-sphingolipid antibodies to bind one or more sphingolipids, thereby acting as therapeutic "sponges" that reduce the level of free undesirable sphingolipids. When a compound is referred to as "free", the compound is not in any way restricted from reaching the site or sites where it exerts its undesirable effects. Typically, a free compound is present in blood and tissue, which either is or contains the site(s) of action of the free compound, or from which a compound can freely migrate to its site(s) of action. A free compound may also be available to be acted upon by any enzyme that converts the compound into an undesirable compound.

Without wishing to be bound by any particular theory, it is believed that the level of undesirable sphingolipids such as SPH or S1P, and/or one or more of their metabolites, cause or contribute to the development of cardiac and myocardial diseases and disorders.

Because sphingolipids are also involved in fibrogenesis and wound healing of liver tissue (Davaille, et al., J. Biol. Chem. 275:34268-34633, 2000; Ikeda, et al., Am J. Physiol. Gastrointest. Liver Physiol 279:G304-G310, 2000), healing of wounded vasculatures (Lee, et al., Am. J. Physiol. Cell Physiol. 278:C612-C618, 2000), and other disease states or disorders, or events associated with such diseases or disorders, such as cancer, angiogenesis, various ocular diseases associate with excessive fibrosis and inflammation (Pyne et al., Biochem. J. 349:385-402, 2000), the compositions and methods of the present disclosure may be applied to treat these diseases and disorders as well as cardiac and myocardial diseases and disorders.

One form of sphingolipid-based therapy involves manipulating the metabolic pathways of sphingolipids in order to decrease the actual, relative and/or available in vivo concentrations of undesirable, toxic sphingolipids. The invention provides compositions and methods for treating or preventing diseases, disorders or physical trauma, in which humanized anti-sphingolipid antibodies are administered to a patient to bind undesirable, toxic sphingolipids, or metabolites thereof.

Such humanized anti-sphingolipid antibodies may be formulated in a pharmaceutical composition and are useful for a variety of purposes, including the treatment of diseases, disorders or physical trauma. Pharmaceutical compositions comprising one or more humanized anti-sphingolipid antibodies of the invention may be incorporated into kits and medical devices for such treatment. Medical devices may be used to administer the pharmaceutical compositions of the invention to a patient in need thereof, and according to one embodiment of the invention, kits are provided that include such devices. Such devices and kits may be designed for routine administration, including self-administration, of the pharmaceutical compositions of the invention. Such devices and kits may also be designed for emergency use, for example, in ambulances or emergency rooms, or during surgery, or in activities where injury is possible but where full medical attention may not be immediately forthcoming (for example, hiking and camping, or combat situations).

3. Methods of Administration

The treatment for diseases and conditions discussed herein can be achieved by administering agents and compositions of the invention by various routes employing different formulations and devices. Suitable pharmaceutically acceptable diluents, carriers, and excipients are well known in the art. One skilled in the art will appreciate that the amounts to be administered for any particular treatment protocol can readily be determined Suitable amounts might be expected to fall within the range of 10 µg/dose to 10 g/dose, preferably within 10 mg/dose to 1 g/dose.

Drug substances may be administered by techniques known in the art, including but not limited to systemic, subcutaneous, intradermal, mucosal, including by inhalation, and topical administration. The mucosa refers to the epithelial tissue that lines the internal cavities of the body. For example, the mucosa comprises the alimentary canal, including the mouth, esophagus, stomach, intestines, and anus; the respiratory tract, including the nasal passages, trachea, bronchi, and lungs; and the genitalia. For the purpose of this specification, the mucosa also includes the external surface of the eye, i.e., the cornea and conjunctiva. Local administration (as opposed to systemic administration) may be advantageous because this approach can limit potential systemic side effects, but still allow therapeutic effect.

Pharmaceutical compositions used in the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations used in the present invention may be prepared according to conventional techniques well known in the pharmaceutical industry. Such techniques include the step of bringing into association the active ingredients with the pharmaceutical carrier(s) or excipient(s). Preferred carriers include those that are pharmaceutically acceptable, particularly when the composition is intended for therapeutic use in humans. For non-human therapeutic applications (e.g., in the treatment of companion animals, livestock, fish, or poultry), veterinarily acceptable carriers may be employed. In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment the pharmaceutical compositions may be formulated and used as foams. Pharmaceutical foams include formulations such as, but not limited to, emulsions, microemulsions, creams, jellies, and liposomes.

While basically similar in nature these formulations vary in the components and the consistency of the final product. The know-how on the preparation of such compositions and formulations is generally known to those skilled in the pharmaceutical and formulation arts and may be applied to the formulation of the compositions of the present invention.

In one embodiment, an immune-derived moiety can be delivered to the eye via, for example, topical drops or ointment, periocular injection, intracamerally into the anterior chamber or vitreous, via an implanted depot, or systemically by injection or oral administration. The quantity of antibody used can be readily determined by one skilled in the art.

The traditional approaches to delivering therapeutics to the eye include topical application, redistribution into the eye following systemic administration or direct intraocular/periocular injections [Sultana, et al. (2006), Current Drug Delivery, vol 3: 207-217; Ghate and Edelhauser (2006), Expert Opinion, vol 3: 275-287; and Kaur and Kanwar (2002), Drug Develop Industrial Pharmacy, vol 28: 473-493]. Anti-S1P or other anti-bioactive lipid antibody therapeutics would likely be used with any of these approaches although all have certain perceived advantages and disadvantages. Topical drops are convenient, but wash away primarily because of nasolacrimal drainage often delivering less than 5% of the applied drug into the anterior section of the eye and an even smaller fraction of that dose to the posterior segment of the globe. Besides drops, sprays afford another mode for topical administration. A third mode is ophthalmic ointments or emulsions can be used to prolong the contact time of the formulation with the ocular surface although blurring of vision and matting of the eyelids can be troublesome. Such topical approaches are still preferable, since systemic administration of therapeutics to treat ocular disorders exposes the whole body to the potential toxicity of the drug.

Treatment of the posterior segment of the eye is medically important because age-related macular degeneration, diabetic retinopathy, posterior uveitis, and glaucoma are the leading causes of vision loss in the United States and other developed countries. Myles, et al. (2005), Adv Drug Deliv Rev; 57: 2063-79. The most efficient mode of drug delivery to the posterior segment is intravitreal injection through the pars plana. However, direct injections require a skilled medical practitioner to effect the delivery and can cause treatment-limiting anxiety in many patients. Periocular injections, an approach that includes subconjunctival, retrobulbar, peribulbar and posterior subtenon injections, are somewhat less invasive than intravitreal injections. Repeated and long-term intravitreal injections may cause complications, such as vitreous hemorrhage, retinal detachment, or endophthalmitis.

The anti-bioactive lipid antibody treatment might also be administered using one of the newer ocular delivery systems [Sultana, et al. (2006), Current Drug Delivery, vol 3: 207-217; and Ghate and Edelhauser (2006), Expert Opinion, vol 3: 275-287], including sustained or controlled release systems, such as (a) ocular inserts (soluble, erodible, non-erodible or hydrogel-based), corneal shields, eg, collagen-based bandage and contact lenses that provide controlled delivery of drug to the eye, (b) in situ gelling systems that provide ease of administration as drops that get converted to gel form in the eye, thereby providing some sustained effect of drug in the eye, (c) vesicular systems such as liposomes, niosomes/discomes, etc., that offers advantages of targeted delivery, bio-compatibility and freedom from blurring of vision, (d) mucoadhesive systems that provide better retention in the eye, (e) prodrugs (f) penetration enhancers, (g) lyophilized carrier systems, (h) particulates, (i) submicron emulsions, (j) iontophoresis, (k) dendrimers, (l) microspheres including bioadhesive microspheres, (m) nanospheres and other nanoparticles, (n) collasomes, and (o) drug delivery systems that combine one or more of the above stated systems to provide an additive, or even synergistic, beneficial effect. Most of these approaches target the anterior segment of the eye and may be beneficial for treating anterior segment disease. However, one or more of these approaches still may be useful affecting bioactive lipid concentrations in the posterior region of the eye because the relatively low molecular weights of the lipids will likely permit considerable movement of the lipid within the eye. In addition, the antibody introduced in the anterior region of the eye may be able to migrate throughout the eye especially if it is manufactured in a lower weight antibody variant such as a Fab fragment. Sustained drug delivery systems for the posterior segment such as those approved or under development (see references, supra) could also be employed.

As previously mentioned, the treatment of disease of the posterior retina, choroids, and macula is medically very important. In this regard, transscleral iontophoresis [Eljarrat-Binstock and Domb (2006), Control Release, 110: 479-89] is an important advance and may offer an effective way to deliver antibodies to the posterior segment of the eye.

Various excipients might also be added to the formulated antibody to improve performance of the therapy, make the therapy more convenient or to clearly ensure that the formulated antibody is used only for its intended, approved purpose. Examples of excipients include chemicals to control pH, anti-microbial agents, preservatives to prevent loss of antibody potency, dyes to identify the formulation for ocular use only, solubilizing agents to increase the concentration of antibody in the formulation, penetration enhancers and the use of agents to adjust isotonicity and/or viscosity. Inhibitors of, e.g., proteases, could be added to prolong the half life of the antibody. In one embodiment, the antibody is delivered to the eye by intravitreal injection in a solution comprising phosphate-buffered saline at a suitable pH for the eye.

The anti-S1P agent (e.g., a humanized antibody) can also be chemically modified to yield a pro-drug that is administered in one of the formulations or devices previously described above. The active form of the antibody is then released by action of an endogenous enzyme. Possible ocular enzymes to be considered in this application are the various cytochrome p450s, aldehyde reductases, ketone reductases, esterases or N-acetyl-β-glucosamidases. Other chemical modifications to the antibody could increase its molecular weight, and as a result, increase the residence time of the antibody in the eye. An example of such a chemical modification is pegylation [Harris and Chess (2003), Nat Rev Drug Discov; 2: 214-21], a process that can be general or specific for a functional group such as disulfide [Shaunak, et al. (2006), Nat Chem Biol; 2:312-3] or a thiol [Doherty, et al. (2005), Bioconjug Chem; 16: 1291-8].

4. Conventional Antibody Generation and Characterization

Antibody affinities may be determined as described in the examples herein below. Preferred humanized or variant antibodies are those which bind a sphingolipid with a $K_d$ value of no more than about $1\times10^{-7}$ M, preferably no more than about $1\times10^{-8}$ M, and most preferably no more than about $5\times10^{-9}$ M.

Aside from antibodies with strong binding affinity for sphingolipids, it is also desirable to select humanized or variant antibodies that have other beneficial properties from a therapeutic perspective. For example, the antibody may be one that reduce angiogenesis and alter tumor progression. Preferably, the antibody has an effective concentration 50 (EC50) value of no more than about 10 ug/ml, preferably no more than about 1 ug/ml, and most preferably no more than about 0.1 ug/ml, as measured in a direct binding ELISA assay. Preferably, the antibody has an effective concentration value of no more than about 10 ug/ml, preferably no more than about 1 ug/ml, and most preferably no more than about 0.1 ug/ml, as measured in cell assays in presence of 1 uM of S1P, for example, at these concentrations the antibody is able to inhibit sphingolipid-induced IL-8 release in vitro by at least 10%. Preferably, the antibody has an effective concentration value of no more than about 10 ug/ml, preferably no more than about 1 ug/ml, and most preferably no more than about 0.1 ug/ml, as measured in the CNV animal model after laser burn, for example, at these concentrations the antibody is able to inhibit sphingolipid-induced neovascularization in vivo by at least 50%.

Assays for determining the activity of the anti-sphingolipid antibodies of the invention include ELISA assays as shown in the examples hereinbelow.

Preferably the humanized or variant antibody fails to elicit an immunogenic response upon administration of a therapeutically effective amount of the antibody to a human patient. If an immunogenic response is elicited, preferably the response will be such that the antibody still provides a therapeutic benefit to the patient treated therewith.

According to one embodiment of the invention, humanized anti-sphingolipid antibodies bind the "epitope" as herein defined. To screen for antibodies that bind to the epitope on a sphingolipid bound by an antibody of interest (e.g., those that block binding of the antibody to sphingolipid), a routine cross-blocking assay such as that described in Antibodies, A Laboratory Manual, Cold Spring Harbor Laboratory, Ed Harlow and David Lane (1988), can be performed. Alternatively, epitope mapping, e.g., as described in Champe, et al. [J. Biol. Chem. 270:1388-1394 (1995)], can be performed to determine whether the antibody binds an epitope of interest.

The antibodies of the invention have a heavy chain variable domain comprising an amino acid sequence represented by the formula: FR1-CDRH1-FR2-CDRH2-FR3-CDRH3-FR4, wherein "FR1-4" represents the four framework regions and "CDRH1-3" represents the three hypervariable regions of an anti-sphingolipid antibody variable heavy domain. FR1-4 may be derived from a "consensus sequence" (for example the most common amino acids of a class, subclass or subgroup of heavy or light chains of human immunoglobulins) as in the examples below or may be derived from an individual human antibody framework region or from a combination of different framework region sequences. Many human antibody framework region sequences are compiled in Kabat, et al., supra, for example. In one embodiment, the variable heavy FR is provided by a consensus sequence of a human immunoglobulin subgroup as compiled by Kabat, et al., above.

The human variable heavy FR sequence preferably has one or more substitutions therein, e.g., wherein the human FR residue is replaced by a corresponding nonhuman residue (by "corresponding nonhuman residue" is meant the nonhuman residue with the same Kabat positional numbering as the human residue of interest when the human and nonhuman sequences are aligned), but replacement with the nonhuman residue is not necessary. For example, a replacement FR residue other than the corresponding nonhuman residue can be selected by phage display. Exemplary variable heavy FR residues which may be substituted include any one or more of FR residue numbers: 37H, 49H, 67H, 69H, 71H, 73H, 75H, 76H, 78H, and 94H (Kabat residue numbering employed here). Preferably at least two, or at least three, or at least four of these residues are substituted. A particularly preferred combination of FR substitutions is: 49H, 69H, 71H, 73H, 76H, 78H, and 94H. With respect to the heavy chain hypervariable regions, these preferably have amino acid sequences listed in Table 2, below.

The antibodies of the preferred embodiment herein have a light chain variable domain comprising an amino acid sequence represented by the formula: FR1-CDRL1-FR2-CDRL2-FR3-CDRL3-FR4, wherein "FR1-4" represents the four framework regions and "CDRL1-3" represents the three hypervariable regions of an anti-sphingolipid antibody variable heavy domain. FR1-4 may be derived from a "consensus sequence" (for example, the most common amino acids of a class, subclass or subgroup of heavy or light chains of human immunoglobulins) as in the examples below or may be derived from an individual human antibody framework region or from a combination of different framework region sequences. In one preferred embodiment, the variable light FR is provided by a consensus sequence of a human immunoglobulin subgroup as compiled by Kabat, et al., above.

The human variable light FR sequence preferably has substitutions therein, e.g., wherein a human FR residue is replaced by a corresponding mouse residue, but replacement with the nonhuman residue is not necessary. For example, a replacement residue other than the corresponding nonhuman residue may be selected by phage display. Exemplary variable light FR residues that may be substituted include any one or more of FR residue numbers, including, but not limited to, F4, Y36, Y49, G64, S67.

Methods for generating humanized anti-sphingolipid antibodies of interest herein are elaborated in more detail below.

A. Antibody Preparation

Methods for humanizing nonhuman anti-sphingolipid antibodies and generating variants of anti-sphingolipid antibodies are described in the Examples below. In order to humanize an anti-sphingolipid antibody, the nonhuman antibody starting material is prepared. Where a variant is to be generated, the parent antibody is prepared. Exemplary techniques for generating such nonhuman antibody starting material and parent antibodies will be described in the following sections.

(i) Antigen Preparation.

The sphingolipid antigen to be used for production of antibodies may be, e.g., intact sphingolipid or a portion of a sphingolipid (e.g., a sphingolipid fragment comprising an "epitope"). Other forms of antigens useful for generating antibodies will be apparent to those skilled in the art. The sphingolipid antigen used to generate the antibody, is described in the examples below. In one embodiment, the antigen is a derivatized form of the sphingolipid, and may be associated with a carrier protein.

(ii) Polyclonal Antibodies.

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 ug or 5 ug of the protein or conjugate (for rabbits or mice, respectively) with three volumes of Freund's complete adjuvant and injecting the solution intradermally at multiple sites. One month later the animals are boosted with 0.1 to 0.2 times the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum may be suitably used to enhance the immune response.

(iii) Monoclonal Antibodies.

Monoclonal antibodies may be made using the hybridoma method first described by Kohler, et al., Nature, 256:495 (1975), or by other suitable methods, including by recombinant DNA methods (see, e.g., U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur, et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbant assay (ELISA).

The binding affinity of a monoclonal antibody can, for example, be determined by the Scatchard analysis of Munson, et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

(iv) Humanization and Amino Acid Sequence Variants.

General methods for antibody humanization are described in, for example, U.S. Pat. No. 5,861,155, US19960652558, U.S. Pat. No. 6,479,284, US20000660169, U.S. Pat. No. 6,407,213, US19930146206, U.S. Pat. No. 6,639,055, US20000705686, U.S. Pat. No. 6,500,931, US19950435516, U.S. Pat. No. 5,530,101, U.S. Pat. No. 5,585,089, US19950477728, U.S. Pat. No. 5,693,761, US19950474040, U.S. Pat. No. 5,693,762, US19950487200, U.S. Pat. No. 6,180,370, US19950484537, US2003229208, US20030389155, U.S. Pat. No. 5,714,350, US19950372262, U.S. Pat. No. 6,350,861, US19970862871, U.S. Pat. No. 5,777,085, US19950458516, U.S. Pat. No. 5,834,597, US19960656586, U.S. Pat. No. 5,882,644, US19960621751, U.S. Pat. No. 5,932,448, US19910801798, US6013256, US19970934841, U.S. Pat. No. 6,129,914, US19950397411, U.S. Pat. No. 6,210,671, U.S. Pat. No. 6,329,511, US19990450520, US2003166871, US20020078757, U.S. Pat. No. 5,225,539, US19910782717, U.S. Pat. No. 6,548,640, US19950452462, U.S. Pat. No. 5,624,821, and US19950479752. In certain embodiments, it may be desirable to generate amino acid sequence variants of these humanized antibodies, particularly where these improve the binding affinity or other biological properties of the humanized antibody. Examples hereinbelow describe methodologies for generating amino acid sequence variants of an anti-sphingolipid antibody with enhanced affinity relative to the parent antibody.

Amino acid sequence variants of the anti-sphingolipid antibody are prepared by introducing appropriate nucleotide changes into the anti-sphingolipid antibody DNA, or by peptide synthesis. Such variants include, for example, deletions from, and/or insertions into and/or substitutions of, residues within the amino acid sequences of the anti-sphingolipid antibodies of the examples herein. Any combination of deletion, insertion, and substitution is made to arrive at the final construct, provided that the final construct possesses the desired characteristics. The amino acid changes also may alter post-translational processes of the humanized or variant anti-sphingolipid antibody, such as changing the number or position of glycosylation sites.

A useful method for identification of certain residues or regions of the anti-sphingolipid antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with sphingolipid antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-sphingolipid antibody variants are screened for the desired activity. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-sphingolipid antibody with an N-terminal methionyl residue or the antibody fused to an epitope tag. Other insertional variants of the anti-sphingolipid antibody molecule include the fusion to the N- or C-terminus of the anti-sphingolipid antibody of an enzyme or a polypeptide which increases the serum half-life of the antibody.

Another type of variant is an amino acid substitution variant. These variants have at least one amino acid residue in the anti-sphingolipid antibody molecule removed and a different residue inserted in its place. The sites of greatest interest for substitutional mutagenesis include the hypervariable regions, but FR alterations are also contemplated. Conservative substitutions are preferred substitutions. If such substitutions result in a change in biological activity, then more substantial changes, denominated "exemplary" substitutions listed below, or as further described below in reference to amino acid classes, may be introduced and the products screened.

TABLE 1

Exemplary Amino Acid Residue Substitutions

| Amino acid residue (symbol) | Exemplary substitutions |
|---|---|
| Ala (A) | val; leu; ile val |
| Arg (R) | lys; gln; asn lys |
| Asn (N) | gln; his; asp, lys; gln arg |
| Asp (D) | glu; asn glu |
| Cys (C) | ser; ala ser |
| Gln (Q) | asn; glu asn |
| Glu (E) | asp; gln asp |
| Gly (G) | ala ala |
| His (H) | asn; gln; lys; arg arg |
| Ile (I) | leu; val; met; ala; leu phe; norleucine |
| Leu (L) | norleucine; ile; val; ile met; ala; phe |
| Lys (K) | arg; gln; asn arg |
| Met (M) | leu; phe; ile leu |
| Phe (F) | leu; val; ile; ala; tyr tyr |
| Pro (P) | ala ala |
| Ser (S) | thr thr |
| Thr (T) | ser ser |
| Trp (W) | tyr; phe tyr |
| Tyr (Y) | trp; phe; thr; ser phe |
| Val (V) | ile; leu; met; phe; leu ala; norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant anti-sphingolipid antibody also may be substituted, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene IIII product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and sphingolipid. Such contact residues and neighboring residues are candidates for substitution according to the techniques elaborated herein. Crystals (co-crystals) of the antigen-antibody complex include co-crystals of the antigen and the Fab or other fragment of the antibody, along with any salts, metals (including divalent metals), cofactors and the like. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked and/or or O-linked. N-linked refers to the attachment of the carbohydrate moiety to the side chain of an asparagine residue. The tripeptide sequences asparagine-X-serine and asparagine-X-threonine, where X is any amino acid except proline, are the most common recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-sphingolipid antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-sphingolipid antibody.

(v) Human Antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits, et al., Proc. Natl. Acad. Sci. USA, 90:2551 (1993); Jakobovits, et al., Nature, 362:255-258 (1993); Bruggermann, et al., Year in Immuno, 7:33 (1993); and U.S. Pat. Nos. 5,591,669, 5,589,369 and 5,545,807. Human antibodies can also be derived from phage-display libraries (Hoogenboom, et al., J. Mol. Biol., 227:381 (1991); Marks, et al., J. Mol. Biol., 222:581-597 (1991); and U.S. Pat. Nos. 5,565,332 and 5,573,905). As discussed above, human antibodies may also be generated by in vitro activated B cells (see, e.g., U.S. Pat. Nos. 5,567,610 and 5,229,275) or by other suitable methods.

(vi) Antibody Fragments.

In certain embodiments, the humanized or variant anti-sphingolipid antibody is an antibody fragment. Various techniques have been developed for the production of antibody fragments. Traditionally, these fragments were derived via proteolytic digestion of intact antibodies (see, e.g., Morimoto, et al., Journal of Biochemical and Biophysical Methods 24:107-117 (1992); and Brennan, et al., Science 229:81 (1985)). However, these fragments can now be produced directly by recombinant host cells. For example, Fab'-SH fragments can be directly recovered from E. coli and chemically coupled to form F(ab')$_2$ fragments (Carter, et al., Bio/Technology 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

(vii) Multispecific Antibodies.

In some embodiments, it may be desirable to generate multispecific (e.g., bispecific) humanized or variant anti-sphingolipid antibodies having binding specificities for at least two different epitopes. Exemplary bispecific antibodies may bind to two different epitopes of the sphingolipid. Alternatively, an anti-sphingolipid arm may be combined with an arm which binds to a different molecule. Bispecific antibodies can be prepared as full length antibodies or antibody fragments (e.g., F(ab')$_2$ bispecific antibodies).

According to another approach for making bispecific antibodies, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See, e.g., U.S. Pat. No. 5,731,168.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in, for example, U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan, et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. Shalaby, et al., J. Exp. Med. 175:217-225 (1992).

Various techniques for making and isolating bispecific antibody fragments directly from recombinant cell culture have also been described. For example, bispecific antibodies have been produced using leucine zippers. Kostelny, et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger, et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, e.g., Gruber, et al., J. Immunol. 152:5368 (1994). Alternatively, the bispecific antibody may be a "linear antibody" produced as described in, fror example, Zapata, et al. Protein Eng. 8(10):1057-1062 (1995).

Antibodies with more than two valencies are also contemplated. For example, trispecific antibodies can be prepared. Tutt et al., J. Immunol. 147:60 (1991).

An antibody (or polymer or polypeptide) of the invention comprising one or more binding sites per arm or fragment thereof will be referred to herein as "multivalent" antibody. For example a "bivalent" antibody of the invention comprises two binding sites per Fab or fragment thereof whereas a "trivalent" polypeptide of the invention comprises three binding sites per Fab or fragment thereof. In a multivalent polymer of the invention, the two or more binding sites per Fab may be binding to the same or different antigens. For example, the two or more binding sites in a multivalent polypeptide of the invention may be directed against the same antigen, for example against the same parts or epitopes of said antigen or against two or more same or different parts or epitopes of said antigen; and/or may be directed against different antigens; or a combination thereof. Thus, a bivalent polypeptide of the invention for example may comprise two identical binding sites, may comprise a first binding sites directed against a first part or epitope of an antigen and a second binding site directed against the same part or epitope of said antigen or against another part or epitope of said antigen; or may comprise a first binding sites directed against a first part or epitope of an antigen and a second binding site directed against the a different antigen. However, as will be clear from the description hereinabove, the invention is not limited thereto, in the sense that a multivalent polypeptide of the invention may comprise any number of binding sites directed against the same or different antigens.

An antibody (or polymer or polypeptide) of the invention that contains at least two binding sites per Fab or fragment thereof, in which at least one binding site is directed against a first antigen and a second binding site directed against a second antigen different from the first antigen, will also be referred to as "multispecific". Thus, a "bispecific" polymer comprises at least one site directed against a first antigen and at least one a second site directed against a second antigen, whereas a "trispecific" is a polymer that comprises at least one binding site directed against a first antigen, at least one further binding site directed against a second antigen, and at least one further binding site directed against a third antigen, etc. Accordingly, in their simplest form, a bispecific polypeptide of the invention is a bivalent polypeptide (per Fab) of the invention. However, as will be clear from the description hereinabove, the invention is not limited thereto, in the sense that a multispecific polypeptide of the invention may comprise any number of binding sites directed against two or more different antigens.

(viii) Other Modifications.

Other modifications of the humanized or variant anti-sphingolipid antibody are contemplated. For example, the invention also pertains to immunoconjugates comprising the antibody described herein conjugated to a cytotoxic agent such as a toxin (e.g., an enzymatically active toxin of bacterial, fungal, plant or animal origin, or fragments thereof), or a radioactive isotope (for example, a radioconjugate). Conjugates are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

The anti-sphingolipid antibodies disclosed herein may also be formulated as immunoliposomes. Liposomes containing the antibody are prepared by methods known in the art, such as described in Epstein et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. For example, liposomes can be generated by the reverse phase evaporation method with a lipid composition comprising phosphatidyl choline, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin, et al., J. Biol. Chem. 257: 286-288 (1982) via a disulfide interchange reaction. Another active ingredient is optionally contained within the liposome.

Enzymes or other polypeptides can be covalently bound to the anti-sphingolipid antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger, et al., Nature 312:604-608 (1984)).

It may be desirable to use an antibody fragment, rather than an intact antibody, to increase penetration of target tissues and cells, for example. In this case, it may be desirable to modify the antibody fragment in order to increase its serum half life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See, e.g., U.S. Pat. No. 6,096,871.

Covalent modifications of the humanized or variant anti-sphingolipid antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

B. Vectors, Host Cells and Recombinant Methods

The invention also provides isolated nucleic acid encoding the humanized or variant anti-sphingolipid antibody, vectors and host cells comprising the nucleic acid, and recombinant techniques for the production of the antibody.

For recombinant production of the antibody, the nucleic acid encoding it may be isolated and inserted into a replicable vector for further cloning (amplification of the DNA) or for expression. In another embodiment, the antibody may be produced by homologous recombination, e.g., as described in U.S. Pat. No. 5,204,244. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, as described, for example, in U.S. Pat. No. 5,534,615.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. lichenifonnis* (e.g., *B. licheniformis* 41P), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-sphingolipid antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244, 234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-sphingolipid antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham, et al., J. Gen Virol. 36:59 (1977)); baby hamster kidney cells (BHK, ATCC CCL 10); Chinese hamster ovary cells/−DHFR (CHO, Urlaub, et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather, et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-sphingolipid antibody production and cultured in conventional nutrient media modified as appropriate for inducing promoters, selecting transformants, or amplifying the genes encoding the desired sequences.

The host cells used to produce the anti-sphingolipid antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham, et al., Meth. Enz. 58:44 (1979), Barnes, et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter, et al., Bio/Technology 10:163-167 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human heavy chains (Lindmark, et al., J. Immunol. Meth. 62:1-13 (1983)). Protein G is recommended for all mouse isotypes and for human γ3 (Guss, et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification, such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

C. Pharmaceutical Formulations

Therapeutic formulations of an antibody or immune-derived moiety of the invention are prepared for storage by mixing the antibody having the desired degree of purity with optional physiologically acceptable carriers, excipients, or stabilizers (see, e.g., Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

The formulations to be used for in vivo administration must be sterile. This is readily accomplished for instance by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

A preferred formulation for systemic administration of the antibodies of the invention is disclosed in provisional patent application U.S. 61/042,736, "Pharmaceutical Compositions for Binding Sphingosine-1-Phosphate", filed Apr. 5, 2008, and commonly owned with the instant invention. This formulation is described in Example 12 hereinbelow.

D. Non-therapeutic Uses for the Antibodies

Antibodies to bioactive lipids may be used as affinity purification agents. In this process, the antibodies are immobilized on a solid phase such a Sephadex resin or filter paper, using methods well known in the art. The immobilized antibody is contacted with a sample containing the sphingolipid to be purified, and thereafter the support is washed with a suitable solvent that will remove substantially all the material in the sample except the sphingolipid, which is bound to the immobilized antibody. Finally, the support is washed with another suitable solvent, such as glycine buffer, for instance between pH 3 to pH 5.0, that will release the sphingolipid from the antibody.

Anti-lipid antibodies may also be useful in diagnostic assays for the target lipid, e.g., detecting its expression in specific cells, tissues (such as biopsy samples), or bodily fluids. Such diagnostic methods may be useful in diagnosis of a cardiovascular or cerebrovascular disease or disorder.

For diagnostic applications, the antibody typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available. For example, U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclicoxidases (such as uricase and xanthine oxidase), lactoperoxidase, microperoxidase, and the like. Techniques for conjugating enzymes to antibodies are described in O'Sullivan, et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the antibody need not be labeled, and the presence thereof can be detected using a labeled secondary antibody which binds to the anti-lipid antibody.

The antibodies of the present invention may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

Competitive binding assays rely on the ability of a labeled standard to compete with the test sample analyte for binding with a limited amount of antibody. The amount of bioactive lipid in the test sample is inversely proportional to the amount of standard that becomes bound to the antibodies. To facilitate determining the amount of standard that becomes bound, the antibodies generally are insoluble before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the blood or tissue sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}$In, $^{99}$Tc, $^{14}$C, $^{131}$I, $^{125}$I, $^{3}$H, $^{32}$P or $^{35}$S) so that the bound target molecule can be localized using immunoscintillography.

E. Diagnostic Kits

As a matter of convenience, antibodies to bioactive lipids can be provided in a kit, for example, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. Therapeutic Uses for the Antibody

For therapeutic applications, antibodies to bioactive lipids are administered to a mammal, preferably a human, in a pharmaceutically acceptable dosage form such as those discussed above, including those that may be administered to a human intravenously as a bolus or by continuous infusion over a period of time, by intramuscular, intraperitoneal, intracerebrospinal, subcutaneous, intra-articular, intrasynovial, intrathecal, oral, topical, or inhalation routes.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 ug/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 µg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic imaging.

According to another embodiment of the invention, the effectiveness of the antibody in preventing or treating disease may be improved by administering the antibody serially or in combination with another agent that is effective for those purposes, such as chemotherapeutic anti-cancer drugs, for example. Such other agents may be present in the composition being administered or may be administered separately. The antibody is suitably administered serially or in combination with the other agent.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-sphingolipid antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

H. Structure-based Design of Humanized Monoclonal Antibodies to Recognize Bioactive Lipids: Platform for Drug Discovery Lpath's proprietary Immune Y2™ technology allows the generation of monoclonal antibodies against bioactive lipids, including sphingolipids. Lpath's mAbs Sonepcizumab and Lpathomab (also referred to as LT1009 and LT3015, targeted to S1P and LPA, respectively) are first-in-class examples of antibody drugs against bioactive lipids.

Because of similarities in the structural framework of LT1009 and LT3015, and aided by recently derived x-ray diffraction data on LT1009 Fab fragment-S1P co-crystals, it is believed that in silico modeling can be used to generate new mAbs against different bioactive lipid targets without the need to immunize mice. This is facilitated by the relatively small sequence/structure space of sphingolipids and similar bioactive lipids compared to that of proteinaceous antigens. It is believed that the expensive and complicated process of humanization can also be avoided by using this in silico method. It is proposed to use structure activity relationship (SAR) assays unique to the Immune Y2 platform to make mutations in the humanized framework and CDRs of LT3015 and/or LT1009, to alter their affinity and/or specificity for their respective ligands. Ultimately it is believed that mutations can be made to alter the specificity to such a point that the binding specificity of the antibody can be converted to a different ligand entirely; e.g., from LPA or S1P (depending on whether LT3015 or LT1009 was the starting point) to another bioactive lipid.

The invention will be better understood by reference to the following Examples, which are intended to merely illustrate the best mode now known for practicing the invention. The scope of the invention is not to be considered limited thereto.

EXAMPLES

Example 1

Murine Monoclonal Antibody to S1P (Sphingomab™; LT1002)

One type of therapeutic antibody specifically binds undesirable sphingolipids to achieve beneficial effects such as, e.g., (1) lowering the effective concentration of undesirable, toxic sphingolipids (and/or the concentration of their metabolic precursors) that would promote an undesirable effect such as a cardiotoxic, tumorigenic, or angiogenic effect; (2) to inhibit the binding of an undesirable, toxic, tumorigenic, or angiogenic sphingolipids to a cellular receptor therefore, and/or to lower the concentration of a sphingolipid that is available for binding to such a receptor. Examples of such therapeutic effects include, but are not limited to, the use of anti-S1P antibodies to lower the effective in vivo serum concentration of available S1P, thereby blocking or at least limiting S1P's tumorigenic and angiogenic effects and its role in post-MI heart failure, cancer, or fibrongenic diseases.

Thiolated S1P was synthesized to contain a reactive group capable of cross-linking the essential structural features of S1P to a carrier molecule such as KLH. Prior to immunization, the thio-S1P analog was conjugated via IOA or SMCC cross-linking to protein carriers (e.g., KLH) using standard protocols. SMCC is a heterobifunctional crosslinker that reacts with primary amines and sulfhydryl groups, and represents a preferred crosslinker.

Swiss Webster or BALB-C mice were immunized four times over a two month period with 50 µg of immunogen (SMCC facilitated conjugate of thiolated-S1P and KLH) per injection. Serum samples were collected two weeks after the second, third, and fourth immunizations and screened by direct ELISA for the presence of anti-S1P antibodies. Spleens from animals that displayed high titers of the antibody were subsequently used to generate hybridomas per standard fusion procedures. The resulting hybridomas were grown to confluency, after which the cell supernatant was collected for ELISA analysis. Of the 55 mice that were immunized, 8 were good responders, showing significant serum titers of antibodies reactive to S1P. Fusions were subsequently carried out using the spleens of these mice and myeloma cells according to established procedures. The resulting 1,500 hybridomas were then screened by direct ELISA, yielding 287 positive hybridomas. Of these 287 hybridomas screened by direct ELISA, 159 showed significant titers. Each of the 159 hybridomas was then expanded into 24-well plates. The cell-conditioned media of the expanded hybridomas were then re-screened to identify stable hybridomas capable of secreting antibodies of interest. Competitive ELISAs were performed on the 60 highest titer stable hybridomas.

Of the 55 mice and almost 1,500 hybridomas screened, one hybridoma was discovered that displayed performance characteristics that justified limited dilution cloning, as is required to ultimately generate a true monoclonal antibody. This process yielded 47 clones, the majority of which were deemed positive for producing S1P antibodies. Of these 47 clones, 6 were expanded into 24-well plates and subsequently screened by competitive ELISA. From the 4 clones that remained positive, one was chosen to initiate large-scale production of the S1P monoclonal antibody. SCID mice were injected with these cells and the resulting ascites was protein A-purified (50% yield) and analyzed for endotoxin levels (<3 EU/mg). For one round of ascites production, 50 mice were injected, producing a total of 125 mL of ascites. The antibodies were isotyped as IgG1 kappa, and were deemed >95% pure by HPLC. The antibody was prepared in 20 mM sodium phosphate with 150 mM sodium chloride (pH 7.2) and stored at −70° C. This antibody is designated LT1002 or Sphingomab™.

The positive hybridoma clone (designated as clone 306D326.26) was deposited with the ATCC (safety deposit storage number SD-5362), and represents the first murine mAb directed against S1P. The clone also contains the variable regions of the antibody heavy and light chains that could be used for the generation of a "humanized" antibody variant, as well as the sequence information needed to construct a chimeric antibody.

Screening of serum and cell supernatant for S1P-specific antibodies was by direct ELISA using a thiolated S1P analog as the antigen. A standard ELISA was performed, as described below, except that 50 ul of sample (serum or cell supernatant) was diluted with an equal volume of PBS/0.1% Tween-20 (PBST) during the primary incubation. ELISAs were performed in 96-well high binding ELISA plates (Costar) coated with 0.1 µg of chemically-synthesized thiolated-S1P conjugated to BSA in binding buffer (33.6 mM $Na_2CO_3$, 100 mM $NaHCO_3$; pH 9.5). The thiolated-S1P-BSA was incubated at 37° C. for 1 hr. at 4° C. overnight in the ELISA plate wells. The plates were then washed four times with PBS (137 mM NaCl, 2.68 mM KCl, 10.14 mM $Na_2HPO_4$, 1.76 mM $KH_2PO_4$; pH 7.4) and blocked with PBST for 1 hr. at room temperature. For the primary incubation step, 75 uL of the sample (containing the S1P to be measured), was incubated with 25 uL of 0.1 ug/mL anti-S1P mAb diluted in PBST and added to a well of the ELISA plate. Each sample was performed in triplicate wells. Following a 1 hr. incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1M $H_2SO_4$. Optical density of the samples was determined by measurement at 450 nm using an EL- X-800 ELISA plate reader (Bio-Tech).

For cross reactivity, a competitive ELISA was performed as described above, except for the following alterations. The primary incubation consisted of the competitor (S1P, SPH, LPA, etc.) and a biotin-conjugated anti-S1P mAb. Biotinylation of the purified monoclonal antibody was performed using the EZ-Link Sulfo-NHS-Biotinylation kit (Pierce). Biotin incorporation was determined as per kit protocol and ranged from 7 to 11 biotin molecules per antibody. The competitor was prepared as follows: lipid stocks were sonicated and dried under argon before reconstitution in DPBS/BSA [1 mg/ml fatty acid free BSA (Calbiochem) in DPBS (Invitrogen 14040-133)]. Purified anti-S1P mAb was diluted as necessary in PBS/0.5% Triton X-100. Competitor and antibody solutions were mixed together so to generate 3 parts competitor to 1 part antibody. A HRP-conjugated streptavidin secondary antibody (Jackson Immunoresearch) was used to generate signal.

Another aspect of the competitive ELISA data is that it shows that the anti-S1P mAb was unable to distinguish the thiolated-S1P analog from the natural S1P that was added in the competition experiment. It also demonstrates that the antibody does not recognize any oxidation products since the analog was constructed without any double bonds. The anti-S1P mAb was also tested against natural product containing the double bond that was allowed to sit at room temperature for 48 hours. Reverse phase HPLC of the natural S1P was performed according to methods reported previously (Deutschman, et al. (July 2003), *Am Heart J.*, vol. 146(1):62-8), and the results showed no difference in retention time. Further, a comparison of the binding characteristics of the monoclonal antibody to various lipids indicates that the epitope recognized by the antibody do not involve the hydrocarbon chain in the region of the double bond of natural S1P. On the other hand, the epitope recognized by the monoclonal antibody is the region containing the amino alcohol on the sphingosine base backbone plus the free phosphate. If the free phosphate is linked with a choline (as is the case with SPC), then the binding was somewhat reduced. If the amino group is esterfied to a fatty acid (as is the case with C1P), no antibody binding was observed. If the sphingosine amino alcohol backbone was replaced by a glycerol backbone (as is the case with LPA), there the S1P-specific monoclonal exhibited no binding. These epitope mapping data indicate that there is only one epitope on S1P recognized by the monoclonal antibody, and that this epitope is defined by the unique polar headgroup of S1P.

In a similar experiment using ELISA measurements, suitable control materials were evaluated to ensure that this anti-S1P monoclonal antibody did not recognize either the protein carrier or the crosslinking agent. For example, the normal crosslinker SMCC was exchanged for IOA in conjugating the thiolated-S1P to BSA as the laydown material in the ELISA. When IOA was used, the antibody's binding characteristics were nearly identical to when BSA-SMCC-thiolated-S1P was used. Similarly, KLH was exchanged for BSA as the protein that was complexed with thiolated-S1P as the laydown material. In this experiment, there was also no significant difference in the binding characteristics of the antibody.

Binding kinetics: The binding kinetics of S1P to its receptor or other moieties has, traditionally, been problematic because of the nature of lipids. Many problems have been associated with the insolubility of lipids. For BIAcore measurements, these problems were overcome by directly immobilizing S1P to a BIAcore chip. Antibody was then flowed over the surface of the chip and alterations in optical density were measured to determine the binding characteristics of the antibody to S1P. To circumvent the bivalent binding nature of antibodies, S1P was coated on the chip at low densities. Additionally, the chip was coated with various densities of S1P (7, 20, and 1000 RU) and antibody binding data was globally fit to a 1:1 interaction model. The results demonstrate the changes in optical density due to the binding of the monoclonal antibody to S1P at three different densities of S1P. Overall, the affinity of the monoclonal antibody to S1P was determined to be very high, in the range of approximately 88 picomolar (pM) to 99 nM, depending on whether a monovalent or bivalent binding model was used to analyze the binding data.

Example 2

ELISA Assays

1. Quantitative ELISAs

Microtiter ELISA plates (Costar, Cat No. 3361) were coated with rabbit anti-mouse IgG, F(ab')$_2$ fragment specific antibody (Jackson, 315-005-047) diluted in 1M Carbonate Buffer (pH 9.5) at 37° C. for 1 h. Plates were washed with PBS and blocked with PBS/BSA/Tween-20 for 1 hr at 37° C. For the primary incubation, dilutions of non-specific mouse IgG or human IgG, whole molecule (used for calibration curve) and samples to be measured were added to the wells. Plates were washed and incubated with 100 ul per well of HRP conjugated goat anti-mouse (H+L) diluted 1:40,000 (Jackson, cat No 115-035-146) for 1 hr at 37° C. After washing, the enzymatic reaction was detected with tetramethylbenzidine (Sigma, cat No T0440) and stopped by adding 1 M H$_2$SO$_4$. The optical density (OD) was measured at 450 nm using a Thermo Multiskan EX. Raw data were transferred to GraphPad software for analysis.

2. Direct ELISAs

Microtiter ELISA plates (Costar, Cat No. 3361) were coated with LPA-BSA diluted in 1M Carbonate Buffer (pH 9.5) at 37° C. for 1 h. Plates were washed with PBS (137 mM NaCl, 2.68 mM KCl, 10.1 mM Na$_2$HPO$_4$, 1.76 mM KH$_2$PO$_4$; pH 7.4) and blocked with PBS/BSA/Tween-20 for 1 h at room temperature or overnight at 4° C. The samples to be tested were diluted at 0.4 ug/mL, 0.2 ug/mL, 0.1 ug/mL, 0.05 ug/mL, 0.0125 ug/mL, and 0 ug/mL and 100 ul added to each well. Plates were washed and incubated with 100 ul per well of HRP conjugated goat anti-mouse (1:20,000 dilution) (Jackson, cat. no. 115-035-003) for 1 h at room temperature. After washing, the enzymatic reaction was detected with tetramethylbenzidine (Sigma, cat. no. T0440) and stopped by adding 1 M H$_2$SO$_4$. The optical density (OD) was measured at 450 nm using a Thermo Multiskan EX. Raw data were transferred to GraphPad software for analysis.

3. Competition Assays

The specificity of mAbs was tested in ELISA assays. Microtiter plates ELISA plates (Costar, Cat No. 3361) were coated with 18:0 LPA-BSA diluted in 1M Carbonate Buffer (pH 9.5) at 37° C. for 1 h. Plates were washed with PBS (137 mM NaCl, 2.68 mM KCl, 10.1 mM Na$_2$HPO$_4$, 1.76 mM KH$_2$PO$_4$; pH 7.4) and blocked with PBS/BSA/Tween-20 at 37° C. for 1 h or overnight at room temperature. For the primary incubation 0.4 ug/mL anti-LPA mAb and designated amounts of (14:0, 16:0, 18:0, 18:1, 18:2 and 20:4) LPA, DSPA, 18:1 LPC (lysophosphatidylcholine), S1P, ceramide and ceramide-1-phosphate were added to wells of the ELISA plates and incubated at 37° C. for 1 h. Plates were washed and incubated with 100 ul per well of HRP conjugated goat anti-mouse (1:20,000 dilution) (Jackson, cat No 115-035-003) or HRP conjugated goat anti-human (H+ L) diluted 1:50,000 (Jackson, cat No109-035-003) at 37° C. for 1 h. After washing, the enzymatic reaction was detected with tetramethylbenzidine and stopped by adding 1 M H$_2$SO$_4$. The optical density (OD) was measured at 450 nm using a Thermo Multiskan EX. Raw data were transferred to GraphPad software for analysis.

Example 3

SPHINGOMAB Murine mAb is Highly Specific for S1P

A competitive ELISA demonstrates SPHINGOMAB's specificity for S1P compared to other bioactive lipids. SPHINGOMAB demonstrated no cross-reactivity to sphingosine (SPH), the immediate metabolic precursor of S1P or lysophosphatidic acid (LPA), an important extracellular signaling molecule that is structurally and functionally similar to S1P. SPHINGOMAB did not recognize other structurally similar lipids and metabolites, including ceramide-1-phosphate (C1P), dihydrosphingosine (DH-SPH), phosphatidyl serine (PS), phosphatidyl ethanolamine (PE), or sphingomyelin (SM). SPHINGOMAB did cross react with dihydrosphingosine-1-phosphate (DH-S1P) and, to a lesser extent, sphingosylphorylcholine (SPC).

Example 4

Biological Activity of SPHINGOMAB

SPHINGOMAB has been shown to significantly reduce choroidal neovascularization (CNV) and scar formation in the eye in a murine model of CNV, and inhibits cardiac scar formation in mice as well. These results and others are disclosed in U.S. patent application Ser. No. 11/924,890, filed on Oct. 26, 2007, entitled "Compositions and Methods for Binding Sphingosine-1-Phosphate," which is incorporated herein in its entirety.

Example 5

Cloning and Characterization of the Variable Domains of an S1P Murine Monoclonal Antibody (LT1002; Sphingomab)

This example reports the cloning of the murine mAb against S1P. The overall strategy consisted of cloning the murine variable domains of both the light chain (VL) and the heavy chain (VH). The consensus sequence of 306D VH shows that the constant region fragment is consistent with a gamma 2b isotype. The murine variable domains were cloned together with the constant domain of the light chain (CL) and with the constant domain of the heavy chain (CH1, CH2, and CH3), resulting in a chimeric antibody construct.

1. Cloning of the Murine mAb

A clone from the anti-S1P hybridoma cell line 306D326.1 (ATCC#SD-5362) was grown in DMEM (Dulbecco's Dulbecco's Modified Eagle Medium with GlutaMAX™ 1,4500 mg/L D-Glucose, Sodium Puruvate; Gibco/Invitrogen, Carlsbad, Calif., 111-035-003), 10% FBS (Sterile Fetal Clone I, Perbio Science), and 1× glutamine/Penicillin/Streptomycin (Gibco/Invitrogen). Total RNA was isolated from $10^7$ hybridoma cells using a procedure based on the RNeasy Mini kit (Qiagen, Hilden Germany). The RNA was used to generate first strand cDNA following the manufacturer's protocol (1$^{st}$ strand synthesis kit, Amersham Biosciences).

The immunoglobulin heavy chain variable region (VH) cDNA was amplified by PCR using an MHV7 primer (MHV7: 5'-ATGGRATGGAGCKGGRTCTTTMTCTT-3' [SEQ ID NO: 1]) in combination with a IgG2b constant region primer MHCG1/2a/2b/3 mixture (MHCG1: 5'-CAGTGGATAGACAGATGGGGG-3' [SEQ ID NO: 2]; MHCG2a: 5'-CAGTGGATAGACCGATGGGGC-3 [SEQ ID NO: 3]; MHCG2b: 5'-CAGTGGATAGACTGATGGGGG-3' [SEQ ID NO: 4]; MHCG3: 5'-CAAGGGATAGACA-GATGGGGC-3' [SEQ ID NO: 5]). The product of the reaction was ligated into the pCR2.1®-TOPO® vector (Invitrogen) using the TOPO-TA Cloning® kit and sequence. The variable domain of the heavy chain was then amplified by PCR from this vector and inserted as a Hind III and Apa I fragment and ligated into the expression vector pG1D200 (see U.S. Pat. No. 7,060,808) or pG4D200 (id.) containing the HCMVi promoter, a leader sequence, and the gamma-1 constant region to generate the plasmid pG1D200306DVH. The consensus sequence of 306D $V_H$ (shown below) showed that the constant region fragment was consistent with a gamma 2b isotype.

Similarly, the immunoglobulin kappa chain variable region (VK) was amplified using the MKV 20 primer (5'-GTCTCT-GATTCTAGGGCA-3' [SEQ ID NO: 6]) in combination with the kappa constant region primer MKC (5'-ACTGGATG-GTGGGAAGATGG-3' [SEQ ID NO: 7]). The product of this reaction was ligated into the pCR2.1®-TOPO® vector using the TOPO-TA Cloning® kit and sequence. The variable domain of the light chain was then amplified by PCR and then inserted as a Bam HI and Hind III fragment into the expression vector pKN100 (see U.S. Pat. No. 7,060,808) containing the HCMV promoter, a leader sequence, and the human kappa constant domain, generating plasmid pKN100306DVK.

The heavy and light chain plasmids pG1D200306DVH plus pKN100306DVK were transformed into DH4a bacteria and stocked in glycerol. Large-scale plasmid DNA was prepared as described by the manufacturer (Qiagen, endotoxin-free MAXIPREP™ kit). DNA samples, purified using Qiagen's QIAprep Spin Miniprep Kit or EndoFree Plasmid Mega/Maxi Kit, were sequenced using an ABI 3730×1 automated sequencer, which also translates the fluorescent signals into their corresponding nucleobase sequence. Primers were designed at the 5' and 3' ends so that the sequence obtained would overlap. The length of the primers was 18-24 bases, and preferably they contained 50% GC content and no predicted dimers or secondary structure. The amino acid sequences for the mouse $V_H$ and $V_L$ domains from Sphingomab™ are SEQ ID NOS: 8 and 9, respectively (Table 2). The CDR residues (see Kabat, E A (1982), Pharmacol Rev, vol. 34: 23-38) are underlined in Table 2, and are shown separately below in Table 3.

TABLE 2

$V_H$ and $V_L$ domains from the murine mAb, Sphingomab™

| | |
|---|---|
| mouse $V_H$ domains | QAHLQQSDAELVKPGASVKISCKVSGFIFID<u>HTIH</u>WMKQRPEQGLEWI GC<u>ISPRHDITKYNEMFRG</u>KATLTADKSSTTAYIQVNSLTFEDSAVYFC AR<u>GGFYGSTIWFDF</u>WGQGTTLTVS |
| | SEQ ID NO: 8 |
| mouse $V_L$ domains | ETTVTQSPASLSMAIGEKVTIRC<u>ITTTDIDDDMN</u>WFQQKPGEPPNLLIS<u>EGNIL</u> <u>RP</u>GVPSRFSSSGYGTDFLFTIENMLSEDVADYYC<u>LQSDNLPFT</u>FGSGTKLEIK |
| | SEQ ID NO: 9 |

TABLE 3

Mouse Sphingomab™ CDR sequences of the mouse $V_H$ and $V_L$ domains

| | | CDR |
|---|---|---|
| $V_L$ CDR | | |
| ITTTDIDDDMN | (SEQ ID NO: 10) | CDR1 |
| EGNILRP | (SEQ ID NO: 11) | CDR2 |
| LQSDNLPFT | (SEQ ID NO: 12) | CDR3 |
| $V_H$ CDR | | |
| DHTIH | (SEQ ID NO: 13) | CDR1 |
| CISPRHDITKYNEMFRG | (SEQ ID NO: 14) | CDR2 |
| GGFYGSTIWFDF | (SEQ ID NO: 15) | CDR3 |

The amino acid sequences of several chimeric antibody variable ($V_H$ and $V_L$) domains are compared in Table 4. These variants were cloned into expression vectors behind germ line leader sequences. The germ line leader sequences are underlined in Table 4 on the pATH200 (first 19 amino acids) and pATH300 sequences (first 22 amino acids). The CDRs are shown in bold. Amino acids that follow the C-terminus of each of the heavy and light chain sequences in Table 4 are shown in italics. These are the first few amino acids of the constant domain and not part of the variable domain.

It should be noted that while the pATH200 and pATH300 series numbers usually refer to a vector containing a particular variable domain variant sequence, for convenience this nomenclature may be used herein to refer to and distinguish the variant variable domains per se.

Sequences of the murine $V_H$ and $V_L$ domains were used to construct a molecular model to determine which framework residues should be incorporated into the humanized antibody.

into DH4a bacteria and stocked in glycerol. Large scale plasmid DNA was prepared as described by the manufacturer (Qiagen, endotoxin-free MAXIPREP™ kit Cat. No. 12362).

For antibody expression in a non-human mammalian system, plasmids were transfected into the African green monkey kidney fibroblast cell line COS 7 by electroporation (0.7 ml at $10^7$ cells/ml) using 10 ug of each plasmid. Transfected cells were plated in 8 ml of growth medium for 4 days. The chimeric 306DH1×306DVK-2 antibody was expressed at 1.5 μg/ml in transiently co-transfected COS cell conditioned medium. The binding of this antibody to S1P was measured using the S1P ELISA.

The expression level of the chimeric antibody was determined in a quantitative ELISA as follows. Microtiter plates (Nunc MaxiSorp immunoplate, Invitrogen) were coated with

TABLE 4

Amino acid sequences of the humanized $V_H$ (pATH200 series) and $V_L$ (pATH300 series) domains-from the humanized anti-S1P antibody variants.

$V_H$ Variants

```
pATH200     mgstailalllavlqgvcsevqlvqsgaevkkpgeslkiscqsfgyifidhtihwvrqmpgqglewmgcisprhditkyn
SEQ ID
NO: 16
pATH201     ..............................................................m.................
pATH202     ........................................f.........m.........i..................
pATH203     ...................................................................i...........
pATH204     ........................................f.......................................
pATH205     ........................................f.........m.........i..................
pATH206     ..............a.........................f.........m.........i..................
pATH207     ...................................................m.................a.........

Sequences Continue:
pATH200     emfrgqvtisadkssstaylqwsslkasdtamyfcarggfygstiwfdfwgqgtmvtvssastkgps
continued
pATH201     ..................................................................
pATH202     ..................................................................
pATH203     ..................................................................
pATH204     ..................................................................
pATH205     .....a.l............................................................
pATH206     .....a.l............................................................
pATH207     ..................................................................
```

$V_L$ Variants

```
pATH300     mdmrvpaqllglllllwlpgarcettltqspsflsasvgdrvtitcitttdiddmnwyqqepgkapklliyegnilrpgv
(SEQ ID
NO: 17)
pATH301     .............................................................................s.........
pATH302     .....................................................................f.................
pATH303     ...................................v...................................s.........
pATH304     .....................................................................f........s.........
pATH305     ...................................v...............................f........s.........
pATH306     ...................................v...............................f........s.........
pATH308     ...................................v...............................f........s.........
pATH309     .............................................................................s.........

Sequences continue
pATH300
continued   psrfsgsgsgtdftltisklqpedfatyyclqsdnlpftfgqgtkleikrewip
pATH301     ......................................................
pATH302     ......................................................
pATH303     .....................................................-
pATH304     .....................................................-
pATH305     ....................................................--
pATH306     .....s..............................................--
pATH308     .....s..y.............................................
pATH309     .....s..y.............................................
```

Leaders are underlined, CDRs are in bold.

2. Expression and Binding Properties of the Chimeric Antibody

The heavy and light chain plasmids of both pG1D200306DVH plus pKN100306DVK were transformed 100 μl aliquots of 0.4 μg/ml goat anti-human IgG antibody (Sigma, St. Louis, Mo.) diluted in PBS and incubate overnight at 4° C. The plates were then washed three times with 200 μl/well of washing buffer (1×PBS, 0.1% TWEEN). Aliquots of 200 µL of each diluted serum sample or fusion supernatant were transferred to the toxin-coated plates and incubated for 37° C. for 1 hr. Following 6 washes with washing buffer, the goat anti-human kappa light chain peroxidase conjugate (Jackson Immuno Research) was added to each well at a 1:5000 dilution. The reaction was carried out for 1 hr at room temperature, plates were washed 6 times with the washing buffer, and 150 µL of the K-BLUE substrate (Sigma) was added to each well, incubated in the dark at room temperature for 10 min. The reaction was stopped by adding 50 µl of RED STOP solution (SkyBio Ltd.) and the absorption was determined at 655 nm using a Microplater Reader 3550 (Bio-Rad Laboratories Ltd.).

3. 293F Expression

The heavy and light chain plasmids were transformed into Top 10 *E. coli* (One Shot Top 10 chemically competent *E. coli* cells (Invitrogen, C4040-10)) and stocked in glycerol. Large scale plasmid DNA was prepared as described by the manufacturer (Qiagen, endotoxin-free MAXIPREP™ kit CatNo 12362).

For antibody expression in a human system, plasmids were transfected into the human embryonic kidney cell line 293F (Invitrogen) using 293fectin (Invitrogen) and using 293F-FreeStyle Media (Invitrogen) for culture. Light and heavy chain plasmids were both transfected at 0.5 g/mL. Transfections were performed at a cell density of $10^6$ cells/mL. Supernatants were collected by centrifugation at 1100 rpm for 5 minutes at 25° C. 3 days after transfection. Expression levels were quantified by quantitative ELISA (see previous examples) and varied from ~0.25-0.5 g/mL for the chimeric antibody.

4. Antibody Purification

Monoclonal antibodies were purified from culture supernatants by passing culture supernatants over protein A/G columns (Pierce, Cat. No 53133) at 0.5 mL/min. Mobile phases consisted of 1× Pierce IgG binding Buffer (Cat. No 21001) and 0.1 M glycine pH 2.7 (Pierce, Elution Buffer, Cat. No 21004). Antibody collections in 0.1 M glycine were diluted 10% (v/v) with 1 M Phosphate Buffer, pH 8.0, to neutralize the pH. $IgG_1$ collections were pooled and dialyzed exhaustively against 1×PBS (Pierce Slide-A-Lyzer Cassette, 3,500 MWCO, Cat. No 66382). Eluates were concentrated using Centricon YM-3 (10,000 MWCO Amicon Cat. No 4203) by centrifugation for 1 h at 2,500 ref. The antibody concentration was determined by quantitative ELISA as described above using a commercial myeloma $IgG_1$ stock solution as a standard. Heavy chain types of mAbs were determined by ELISA using Monoclonal Antibody Isotyping Kit (Sigma, ISO-2).

5. Comparative Binding of Antibody Variants to S1P

Table 5, below, shows a comparative analysis of mutants with the chimeric antibody. To generate these results, bound antibody was detected by a second antibody, specific for the mouse or human IgG, conjugated with HRP. The chromogenic reaction was measured and reported as optical density (OD). The concentration of the panel of antibodies was 0.1 ug/ml. No interaction of the second antibody with S1P-coated matrix alone was detected.

TABLE 5

Comparative binding to S1P on variants of the chimeric anti-S1P antibody.

| Variable Domain | Mutation | Plasmids | Binding |
|---|---|---|---|
| HC | Chimeric | pATH50 + pATH10 | 1.5 |
|  | CysAla | pATH50 + pATH11 | 2 |
|  | CysSer | pATH50 + pATH12 | 0.6 |

TABLE 5-continued

Comparative binding to S1P on variants of the chimeric anti-S1P antibody.

| Variable Domain | Mutation | Plasmids | Binding |
|---|---|---|---|
|  | CysArg | pATH50 + pATH14 | 0.4 |
|  | CysPhe | pATH50 + pATH16 | 2 |
| LC | MetLeu | pATH53 + pATH10 | 1.6 |

6. Determination of Binding Kinetics by Surface Plasmon Resonance (SPR)

All binding data were collected on a Biacore 2000 optical biosensor (Biacore AB, Uppsala Sweden). S1P was coupled to a maleimide CM5 sensor chip. First the CM5 chip was activated with an equal mixture of NHS/EDC for seven minutes followed by a 7 minute blocking step with ethyldiamine. Next sulfo-MBS (Pierce Co.) was passed over the surfaces at a concentration of 0.5 mM in HBS running buffer (10 mM HEPES, 150 mM NaCl, 0.005% p20, pH 7.4). S1P was diluted into the HBS running buffer to a concentration of 0.1 mM and injected for different lengths of time producing 2 different density S1P surfaces (305 and 470 RU). Next, binding data for the mAb was collected using a 3-fold dilution series starting with 16.7 nM, 50.0 nM, 50.0 nM, 16.7 nM, and 16.7 nM for the mouse, 201308, 201309, and 207308 antibodies respectively.

Each concentration was tested in duplicate. Surfaces were regenerated with 50 mM NaOH. All data were collected at 25'C. Responses data were processed using a reference surface as well as blank injections. The data sets (responses from two surfaces and each variant tested twice were fit to interaction models to obtain binding parameters. Data from the different mAb concentrations were globally fitted using a 1:1 (mouse) or 1:2 (variants) interaction model to determine apparent binding rate constants. The number in parentheses indicates the error in the last digit.

Example 6

Chimeric mAb to S1P

As used herein, the term "chimeric" antibody (or "immunoglobulin") refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., supra; Morrison et al., Proc. Natl. Acad. Sci. U.S.A. 81:6851 (1984)).

A chimeric antibody to S1P was generated using the variable regions (Fv) containing the active S1P binding regions of the murine antibody from a particular hybridoma (ATCC safety deposit storage number SD-5362) with the Fc region of a human IgG1 immunoglobulin. The Fc regions contained the CL, ChL, and Ch3 domains of the human antibody. Without being limited to a particular method, chimeric antibodies could also have been generated from Fc regions of human IgG1, IgG2, IgG3, IgG4, IgA, or IgM. As those in the art will appreciate, "humanized" antibodies can been generated by grafting the complementarity determining regions (CDRs, e.g. CDR1-3) of the murine anti-S1P mAb with a human antibody framework regions (e.g., Fr1, Fr4, etc.) such as the framework regions of an IgG1.

For the direct ELISA experiments, the chimeric antibody to S1P had similar binding characteristics to the fully murine monoclonal antibody. ELISAs were performed in 96-well high-binding ELISA plates (Costar) coated with 0.1 ug of chemically-synthesized, thiolated S1P conjugated to BSA in binding buffer (33.6 mM $Na_2CO_3$, 100 mM $NaHCO_3$; pH 9.5). The thiolated S1P-BSA was incubated at 37° C. for 1 hr. or at 4° C. overnight in the ELISA plate. Plates were then washed four times with PBS (137 mM NaCl, 2.68 mM KCl, 10.14 mM $Na_2HPO_4$, 1.76 mM $KH_2PO_4$; pH 7.4) and blocked with PBST for 1 hr. at room temperature. For the primary incubation step, 75 uL of the sample (containing the S1P to be measured), was incubated with 25 µL of 0.1 µg/mL anti-S1P monoclonal antibody diluted in PBST and added to a well of the ELISA plate. Each sample was performed in triplicate wells. Following a 1 hr. incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1M $H_2SO_4$. Optical density of the samples was determined by measurement at 450 nm using an EL-X-800 ELISA plate reader (Bio-Tech).

Again, the preferred method of measuring either antibody titer in the serum of an immunized animal or in cell-conditioned media (for example, supernatant) of an antibody-producing cell such as a hybridoma, involves coating the ELISA plate with a target ligand (e.g., a thiolated analog of S1P, LPA, etc.) that has been covalently linked to a protein carrier such as BSA.

Without being limited to particular method or example, chimeric antibodies could be generated against other lipid targets such as LPA, PAF, ceramides, sulfatides, cerebrosides, cardiolipins, phosphotidylserines, phosphotidylinositols, phosphatidic acids, phosphotidylcholines, phosphatidylethanolamines, eicosinoids, and other leukotrienes, etc. Further, many of these lipids could also be glycosylated and/or acetylated, if desired.

Example 7

Generation and Characterization of Humanized Anti-S1P Monoclonal Antibody LT1009 (Sonepcizumab)

The murine anti-S1P monoclonal antibody 306D (LT1002; Sphingomab™), which specifically binds S1P, has been shown to potently suppress angiogenesis and tumor growth in various animal models. As discussed below, LT1002 was humanized using sequence identity and homology searches for human frameworks into which to graft the murine CDRs and a computer-generated model to guide some framework backmutations. Two variants, HuMAbHCLC$_3$ (LT1004) (with 3 backmutations in the light chain) and HuMAbHCLC$_5$ (LT1006) (with 5 backmutations in the light chain) exhibited binding affinity in the nanomolar range. Further engineering was performed in an effort to improve the biophysical and biological properties of the humanized variants. The humanized variants HuMAbHC$_{CysAla}$LC$_3$ (LT1007) and HuMAbH-C$_{CysAla}$LC$_5$ (LT1009) in which a free-cysteine residue in HCDR2 was replaced with alanine exhibited a binding affinity in the picomolar range. All humanized variants inhibited angiogenesis in the choroid neovascularization (CNV) model of age-related macular degeneration (AMD), with HuMAb-HC$_{CysAla}$LC$_5$ (LT1009) exhibiting superior stability and in vivo efficacy compared to the parent murine antibody. The variant huMAbHCcysalaLC$_5$ (LT1009) was designated Sonepcizumab™.

1. Humanization Design for the Anti-S1P Antibody

The variable domains of murine mAb LT1002 (Sphingomab™) were humanized via CDR grafting (Winter U.S. Pat. No. 5,225,539). The CDR residues were identified based on sequence hypervariability as described by Kabat et al. 1991.

In this study, suitable acceptor structures were selected based on a homology search of human antibodies in the IMGT and Kabat databases using a structural alignment program (SR v7.6). The initial step was to query these human heavy variable (VH) and light variable (VL) sequence databases with LT1002 VH and VL protein sequences respectively, to identify human frameworks (FR) with high sequence identity in the FR, at Vernier (Foote, J. & Winter, G. Antibody framework residues affecting the conformation of the hypervariable loops. *J Mol. Biol.* 224, 487-499 (1992)), Canonical (Morea, et al., Antibody modeling: implications for engineering and design, Methods 20, 267-279 (2000) and VH-VL interface (Chothia, C., Novotny, J., Bruccoleri, R., & Karplus, M. Domain association in immunoglobulin molecules. The packing of variable domains. J. Mol. Biol. 186, 651-663 (1985)) residues and with CDRs of identical canonical class and/or length. The identity of each member of this library to individual aligned residues of the mouse antibody was calculated using the program. Those human sequences with FR sequence most identical to the mouse FR were identified, producing an initial shortlist of human "acceptor" sequences. Those sequences with most identity to the mouse antibody, at Vernier, Canonical and VH-VL Interface (VCI) residues, were also calculated. Differences at these positions between human and mouse were classified into conservative and non-conservative substitutions, so that the best framework choice would have the lowest number of non-conservative VCI differences from LT1002. The CDR loops L3 and H1 of LT1002 could be classified into canonical structures. These L3 and H1 structures were used to select human antibody FRs with identical canonical structures. For unclassified CDRs, an attempt was made to select human frameworks with CDR lengths identical to the mouse antibody. The rationale is that CDR loop structures are dependent not only on the CDR loop sequence itself, but also on the underlying framework residues (canonical residues). Therefore a human framework with matching canonical CDR structures and/or CDR lengths is likely to hold the grafted mouse CDRs in the most appropriate orientation to maintain antigen binding affinity. This was achieved for all CDRs except CDR H3, by the choice of human framework sequences. Additionally, frameworks with unusual cysteine or proline residues were excluded where possible. These calculations were performed separately for the heavy and light chain sequences. Finally, individual sequence differences, throughout the framework region, in the best matching sequences were compared. Of the human antibodies that best fit the above comparative calculations, the antibodies AY050707 and AJ002773 were selected as the most appropriate human framework provider for the light chain and the heavy chain respectively. The AY050707 framework was described by van den Brink, et al. (Blood, 15 Apr. 2002, Vol. 99, No. 8, pp 2828-2834) and its sequence is available via Genbank (accession no. AY050707; *Homo sapiens* clone WR3VL immunoglobulin light chain variable region mRNA, partial cds.; submitted Nov. 13, 2001, last revision Apr. 8, 2002).

Similarly, the AJ002773 antibody framework was described by Snow, et al. [Eur. J. Immunol. 28 (10), 3354-3361 (1998)], and its sequence is available via Genbank (accession no. AJ002772; *Homo sapiens* mRNA for variable region 5 of immunoglobulin G4 heavy chain patient 2,2; submitted Nov. 6, 1998, last revision Oct. 16, 2006).

Both the AY050707 (light chain) and the AJ002773 (heavy chain) sequences are also found in IMGT/LIGM, a comprehensive database of immunoglobulin (IG) and T cell receptor (TR) nucleotide sequences from human and other vertebrate species. This database was created in 1989 by Marie-Paule Lefranc, LIGM, Montpellier, France, and has been available online since July 1995.

The second step was to generate a molecular model of the variable regions of LT1002 and to identify FR residues which might affect antigen binding but were not included in the group of Vernier, Canonical and Interface residues. Many structural features of the graft donor and acceptor variable domains were examined in order to better understand how various FR residues influence the conformation of the CDR loops and vice versa. Non-conserved FR residues in LT1002 that were likely to impact the CDRs were identified from the Vernier and Canonical definitions (see above) and thus several residues of the human FR were restored to the original murine amino acids (backmutated).

2. Mutagenesis

Mutations within the variable domain sequences were created using the QuikChange Site-Directed Mutagenesis Kit (Stratagene, Catalog #200524). Individual reactions were carried out with 50 ng of double-stranded DNA template, 2.5 U of PfuUltre HF DNA polymerase and its corresponding buffer (Stratagene, Catalog #200524), 10 mM dNTP mix and 125 ng of each of the mutagenic oligonucleotides resuspended in 5 mM Tris-HCl (pH 8.0), and 0.1 mM EDTA. The initial denaturation was carried out at 95° C. for 30 s, followed by 16 cycles of amplification: 95° C. for 30 s, 55° C. for 60 s and 68° C. for 8 min. Following temperature cycling, the final reaction was then digested with DpnI digest at 37° C. for 1 h to remove methylated parental DNA. The resultant mutant was transformed into competent XL1-Blue *E. coli* and plated on LB-agar containing 50 μg/ml Ampicillin. The colonies were then checked by sequencing. Each of the mutants were then cultured in 1 liter shake flasks and purified using the EndoFree Plasmid Purification Kit from Qiagen, catalog #12362.

3. Generation of the Humanized Antibody Variants

A mouse-human chimeric antibody (chMAb S1P) was constructed by cloning the variable domains of LT1002 into a vector that contained the human constant regions of the kappa and heavy chains to allow expression of the full length antibody into mammalian cells. The generation of the humanized heavy chain was the result of the graft of the Kabat CDRs 1, 2 and 3 from LT1002 $V_H$ into the acceptor framework of AJ002773. The nearest germ line gene to AJ002773 was VH5-51, whose leader sequence was incorporated, as a leader sequence, into the humanized heavy chain variant. The protein sequence of pATH200, the first humanized version of LT1002 $V_H$, with the VH5-51 leader sequence, is shown in Table 4. In the case of the $V_H$ domain of LT1002, residues at position 2, 27, 37, 48, 67 and 69 were Vernier residues or at the interface of the $V_H$ and $V_L$ domains and likely to influence CDR orientation. Position 37 appeared to be critical for the interface between the $V_H$ and $V_L$ domains. The residues at these positions in the human framework were backmutated with the murine residue found at the corresponding position. The mutations, V37M, M48I and Y27F, were tested individually. One version (pATH205) contained all 3 mutations together with V67A plus I69L and another version (pATH206) contained all 5 mutations plus V2A.

The generation of the humanized light chain was the result of the graft of the Kabat CDRs 1, 2 and 3 from LT1002 $V_L$ into the acceptor framework of AY050707. The nearest germ line gene to AY050707 was L11, whose leader sequence was incorporated into the humanized light chain construct. The protein sequence of pATH300 (LT1002 light chain) is shown in Table 4. Germline leader sequences are indicated by underlining in Table 4. In the case of $V_L$, four non-conserved Vernier positions 4, 36, 49, 64 were selected for backmutation to murine residues as they are involved in supporting the structure of the CDR loops. Inspection of the molecular model of LT1002 suggested that Tyr 67 is close to the CDR surface and oriented towards the antigen binding plane and could interact with S1P. Therefore the S67Y backmutation was also added to later humanized versions. Two mutations were introduced separately to generate two versions containing either Y49S or Y36F. Several versions were created with the following combinations of mutations: (Y49S, F4V), (Y49S,Y36F), (Y49S,Y36F,F4V), (Y49S, G64S), (Y49S, Y36F, F4V,G64S), (Y49S,Y36F, F4V, G64S, S67Y), (Y49S, G64S,S67Y).

4. Selection of the Humanized Lead Candidates

The variable regions of the basic grafted versions (pATH 200 and pATH 300) and all the variants containing backmutations were cloned into expression vectors containing the human $V_H$ or $V_L$ constant regions. All the humanized variants were produced in mammalian cells under the same conditions as the chimeric (chMAb) antibody and were tested for binding to S1P by ELISA. The yield was approximately 10-20 mg/l for the humanized variants and 0.3-0.5 mg/l for chMAb S1P. SDS-PAGE under reducing conditions revealed two bands at 25 kDa and 50 kDa with high purity (>98%), consistent with the expected masses of the light and heavy chains. A single band was observed under non-reducing conditions with the expected mass of ~150 k. chMAb was used as a standard in the humanized antibody binding assays because it contained the same variable regions as the parent mouse antibody and bore the same constant regions as the humanized antibodies and therefore could be detected using the same ELISA protocol.

The initial humanized antibody, in which the six murine CDRs were grafted into unmutated human frameworks, did not show any detectable binding to S1P. The kappa light chain containing the 4 backmutations (Y49S, Y36F, F4V and G64S), in association with chimeric heavy chain, exhibited suboptimal binding to S1P as measured by ELISA. The incorporation of an additional mutation at position Y67 significantly improved the binding. Version pATH308 which contained backmutations Y49S, Y36F, F4V, G64S and S67Y and version pATH309 which contained the backmutations Y49S, G64S and S67Y, in association with chimeric heavy chain, both generated antibodies which bound S1P similarly to the chimeric antibody as determined by ELISA. The 2 mutations Y36F and F4V were not considered necessary backmutations from the viewpoint of S1P binding. The engineering of 3 to 5 backmutations in the VL framework was required to restore activity.

The incorporation of the Vernier backmutation V37M into the human framework of the heavy chain, in association with the chimeric light chain, was sufficient to restore a binding behavior similar to the chimeric antibody.

In summary, humanization of the LT1002 $V_H$ domain required only one amino acid from the murine framework sequence whereas the murine $V_L$ framework domain, three or five murine residues had to be retained to achieve binding equivalent to the murine parent LT1002.

5. Optimization of a Humanized Lead Candidate

The murine anti-S1P antibody contains a free cysteine residue in CDR2 (Cys50) of the heavy chain that could potentially cause some instability of the antibody molecule. Using site directed mutagenesis, variants of pATH201 were created with substitution of the cysteine residue with alanine (huMAbHCcysalaLC$_3$) (pATH207), glycine (huMAbHCcysglaLC$_3$), serine (huMAbHCcysserLC$_3$), and phenylalanine (huMAbHCcyspheLC$_3$). The cysteine mutant heavy chain was also tested with the humanized light chain (pATH 308) containing 5 backmutations (huMAbHCcysalaLC$_5$=LT1009). The variants were expressed in mammalian cells and then characterized in a panel of in vitro assays. Importantly, the expression rate of the humanized variants was significantly higher than for chMAb S1P.

6. In-Depth Characterization of the Humanized Lead Candidate i. Specificity. The humanized variants were tested for specificity in a competitive ELISA assay against S1P and several other biolipids. This assay has the added benefit to allow for epitope mapping. The humanized antibody LT1009 demonstrated no cross-reactivity to sphingosine (SPH), the immediate metabolic precursor of S1P, or LPA (lysophosphatidic acid), an important extracellular signaling molecule that is structurally and functionally similar to S1P. Moreover, rhuMAb S1P did not recognize other structurally similar lipids and metabolites, including ceramide (CER), ceramide-1-phosphate (C1P). However as expected LT1009 did cross react with sphingosyl phosphocholine (SPC), a lipid in which the free phosphate group of S1P is tied up with a choline residue. Importantly, all the humanized variants exhibited a specificity profile comparable to the mouse antibody.

ii. Binding affinity. Biacore measurements of IgG binding to a S1P coated chip showed that the variants LT1004 or LT1006 exhibited binding affinity in the low nanomolar range similar to chMAb S1P. The humanized variants LT1007 and LT1009 in which the cysteine residue was replaced with alanine exhibited a binding affinity in the picomolar range similar to the murine parent LT1002 (Sphingomab™).

iii. Stability. The humanized variants were tested for stability after challenge at high temperature. The approximate midpoints of the thermal unfolding transitions ($T_M$) were determined for every humanized variant by subjecting the supernatants to temperatures ranging from 60 to 74° C. These temperatures were chosen based on the denaturation profile observed for the murine antibody molecule after thermochallenging between a broad range of temperatures between 50 and 80° C. The binding properties of each variant were determined before and after thermochallenge. The murine antibody exhibited a $T_M$ of 65° C. The variant huMAbHCcysalaLC$_5$ (LT1009) exhibited superior $T_M$ compared to all other variants. Table 6 shows the lead humanized candidates and their characteristics.

TABLE 6

Lead humanized S1P mAb candidates and characteristics
The number of mutations in the heavy and light chains are indicated.
The description column gives the identity of the heavy and light chains.

| mAb | Description | Mutations in the Heavy Chain | | Mutations in the Light Chain | | In vitro Activity | |
|---|---|---|---|---|---|---|---|
| | | CDR | Framework | CDR | Framework | Binding Affinity ($K_{D1}$) | Specificity (ELISA) |
| LT1002 | Murine mAb Sphingomab | N/A | N/A | N/A | N/A | 0.026 ± 0.000 nM | High |
| LT1004 | HuHCLC$_3$ pATH201HC pATH309LC | 0 | 1 | 0 | 3 | 1.060 ± 0.010 nM | High |
| LT1006 | HuHCLC$_5$ pATH201HC pATH308LC | 0 | 1 | 0 | 5 | 0.690 ± 0.010 nM | High |
| LT1007 | HuHCcysalaLC$_3$ pATH207HC pATH309LC | 1 | 1 | 0 | 3 | 0.0414 ± 0.0004 nM | |
| LT1009 | HuHCcysalaLC$_5$ pATH207HC pATH308LC | 1 | 1 | 0 | 5 | 0.056 ± 0.001 nM | High | iv. Sequences

As with naturally occurring antibodies, LT1009 includes three complementarity determining regions (each a "CDR") in each of the two light chain polypeptides and each of the two heavy chain polypeptides that comprise each antibody molecule. The amino acid sequences for each of these six CDRs is provided immediately below ("VL" designates the variable region of the immunoglobulin light chain, whereas "VH" designates the variable region of the immunoglobulin heavy chain):

```
CDR1   VL: ITTTDIDDDMN        [SEQ ID NO: 10]

CDR2   VL: EGNILRP             [SEQ ID NO: 11]
```

```
            -continued
CDR3    VL: LQSDNLPFT           [SEQ ID NO: 12]

CDR1    VH: DHTIH               [SEQ ID NO: 13]

CDR2    VH: AISPRHDITKYNEMFRG   [SEQ ID NO: 18]

CDR3    VH: GGFYGSTIWFDF        [SEQ ID NO: 15]
```

Example 8

Humanized S1P mAb Production and Purification

This example describes the production of a recombinant humanized monoclonal antibody (LT1009) that binds with high affinity to the bioactive lipid sphingosine-1-phosphate (S1P). LT1009 is a full-length IgG1k isotype antibody composed of two identical light chains and two identical heavy chains with a total molecular weight of approximately 150 kDa. The heavy chain contains an N-linked glycosylation site. The nature of the oligosaccharide structure has not yet been determined but is anticipated to be a complex biantennary structure with a core fucose. The nature of the glycoform that will be predominant is not known at this stage. Some C-terminal heterogeneity is expected because of the presence of lysine residues in the constant domain of the heavy chain. The two heavy chains are covalently coupled to each other through two inter-chain disulfide bonds, which is consistent with the structure of a human IgG1.

LT1009 was originally derived from a murine monoclonal antibody (LT1002; Sphingomab™) that was produced using hybridomas generated from mice immunized with S1P. The humanization of the murine antibody involved the insertion of the six murine CDRs in place of those of a human antibody framework selected for its structure similarity to the murine parent antibody. A series of substitutions were made in the framework to engineer the humanized antibody. These substitutions are called back mutations and replace human with murine residues that are play a significant role in the interaction of the antibody with the antigen. The final humanized version contains one murine back mutation in the human framework of variable domain of the heavy chain and five murine back mutations in the human framework of the variable domain of the light chain. In addition, one residue present in the CDR #2 of the heavy chain was substituted to an alanine residue. This substitution was shown to increase stability and potency of the antibody molecule.

The humanized variable domains (both heavy and light chain) were cloned into the Lonza's GS gene expression system to generate the plasmid pATH1009. The Lonza GS expression system consists of an expression vector carrying the constant domains of the antibody genes and the selectable marker glutamine synthetase (GS). GS is the enzyme responsible for the biosynthesis of glutamine from glutamate and ammonia. The vector carrying both the antibody genes and the selectable marker is transfected into a proprietary Chinese hamster ovary host cell line (CHOK1SV) adapted for growth in serum-free medium and provides sufficient glutamine for the cell to survive without exogenous glutamine. In addition, the specific GS inhibitor, methionine sulphoximine (MSX), is supplemented in the medium to inhibit endogenous GS activity such that only the cell lines with GS activity provided by the vector can survive. The resulting CHO cell line transfected with pATH1009 is named LH1.

It should be noted that the natural germ line gene leader sequences described in the above examples are replaced by leader sequences in the GS expression vector backbone used to produce the plasmid pATH1009. The latter leader sequences can be seen as 19 amino acids beginning "mewswv," at the N-terminus of the LT1009 heavy chain (SEQ ID NO: 19 and 24), and the LC leader is 20 amino acids beginning "msvpt" (as shown at the N-terminus of SEQ ID NO: 20 and 26).

The transfected CHO LH1 cells were selected for their ability to grow in glutamine-free medium in the presence of MSX and isolates (clones) were selected for high level of secretion of active LT1009. LH1 275 is the name given to the lead clone of the LH1 CHO cell line containing the pATH1009 vector selected for the creation of a Master Cell Bank (MCB) for production of all lots of LT1009 antibody product. Material for toxicology studies and clinical development were then produced for tox and clinical development.

ATCC deposits: *E. coli* StB12 containing the pATH1009 plasmid has been deposited with the American Type Culture Collection (deposit number PTA-8421). CHO cell line LH1 275, which contains the pATH1009 vector has also been deposited with the American Type Culture Collection (deposit number PTA-8422).

Sequences:

The nucleotide and amino acid sequences for the heavy and light chain polypeptides of LT1009 are listed immediately below. Leader sequences (from Lonza GS expression vector) are underlined; CDRs are in bold.

```
LT1009 HC amino acid sequence of the variable domain [SEQ ID NO: 19]:
  1 mewswvflfflsvttqvhsevqlvqsgaevkkpgeslkiscgsfgyifid 51 htihwmrqmpgqglewmgaisprhditkynemfrgqvtisadkssstayl 101 qwsslkasdtamyfcarggfygstiwfdfwgqgtmvtvss LT1009 LC amino acid sequence of the variable domain [SEQ ID NO: 20]:
  1 msvptqvlqllllwltdarcettvtqspsflsasvgdrvtitcitttdid 51 ddmnwfqqepgkapkllisegnilrpgvpsrfsssgygtdftltisklqp 101 edfatyyclqsdnlpftfgqgtkleik
```

Corresponding nucleotide sequences encoding the heavy and light chain variable domains are listed immediately below. Leader sequences (from Lonza GS expression vector) are underlined; sequences preceding the leader are HindIII cut site (aagctt) and Kozak consensus sequence (gccgccacc), which plays a major role in the initiation of translation process; CDRs are in bold:

LT1009 HC nucleotide sequence of the variable domain [SEQ ID NO: 21]
  1  aagcttgccg ccacc<u>atgga atggagctgg gtgttcctgt tctttctgtc</u>

51  <u>cgtgaccaca ggcgtgcatt ct</u>gaggtgca gctggtgcag tctggagcag 101  aggtgaaaaa gcccggggag tctctgaaga tctcctgtca gagttttgga 151  tacatcttta tcgaccatac tattcactgg atgcgccaga tgcccgggca 201  aggcctggag tggatggggg ctatttctcc cagacatgat attactaaat

251  acaatgagat gttcaggggc caggtcacca tctcagccga caagtccagc 301  agcaccgcct acttgcagtg gagcagcctg aaggcctcgg acaccgccat 351  gtatttctgt gcgagagggg ggttctacgg tagtactatc tggtttgact

401  tttggggcca agggacaatg gtcaccgtct cttca

LT1009 LC nucleotide sequence of the variable domain [SEQ ID NO. 22]
  1  aagcttgccg ccacc<u>atgtc tgtgcctacc caggtgctgg gactgctgct</u>

51  <u>gctgtggctg acagacgccc gctgt</u>gaaac gacagtgacg cagtctccat 101  ccttcctgtc tgcatctgta ggagacagag tcaccatcac ttgcataacc

151  accactgata ttgatgatga tatgaactgg ttccagcagg aaccagggaa 201  agcccctaag ctcctgatct ccgaaggcaa tattcttcgt cctggggtcc 251  catcaagatt cagcagcagt ggatatggca cagatttcac tctcaccatc 301  agcaaattgc agcctgaaga ttttgcaact tattactgtt tgcagagtga

351  taacttacca ttcactttcg gccaagggac caagctggag atcaaa

LT1009 full length HC nucleotide (cDNA) sequence [SEQ ID NO: 23] with
CDRs in bold and leader region underlined; hinge region is in italics.
Sequences preceding the leader are HindIII cut site (aagctt) and Kozak
sequence (gccgccacc):
aagcttgccgccacc<u>atggaatggagctgggtgttcctgttctttctgtccgtgaccacaggcgtgcatt</u>

<u>ct</u>gaggtgcagctggtgcagtctggagcagaggtgaaaaagcccggggagtctctgaagatctcctgtca gagttttggatacatctttatcgaccatactattcactggatgcgccagatgcccgggcaaggcctggag tggatgggggctatttctcccagacatgatattactaaatacaatgagatgttcaggggccaggtcacca tctcagccgacaagtccagcagcaccgcctacttgcagtggagcagcctgaaggcctcggacaccgccat gtatttctgtgcgagaggggggttctacggtagtactatctggtttgacttttggggccaagggacaatg gtcaccgtctcttcagcctccaccaagggcccatcggtcttccccctggcacccctcctccaagagcacct ctggggggcacagcggccctgggctgcctggtcaaggactacttccccgaaccggtgacggtgtcgtggaa ctcaggcgccctgaccagcggcgtgcacaccttcccggctgtcctacagtcctcaggactctactccctc agcagcgtggtgaccgtgccctccagcagcttgggcacccagacctacatctgcaacgtgaatcacaagc ccagcaacaccaaggtggacaagagagtt*gagcccaaatcttgtgacaaaactcacacatgcccaccgtg*

*ccc*agcacctgaactcctggggggaccgtcagtcttcctcttccccccaaaacccaaggacaccctcatg atctcccggacccctgaggtcacatgcgtggtggtggacgtgagccacgaagaccctgaggtcaagttca actggtacgtggacggcgtggaggtgcataatgccaagacaaagccgcgggaggagcagtacaacagcac gtaccgtgtggtcagcgtcctcaccgtcctgcaccaggactggctgaatggcaaggagtacaagtgcaag gtctccaacaaagccctcccagcccccatcgagaaaaccatctccaaagccaaagggcagccccgagaac cacaggtgtacaccctgcccccatcccgggaggagatgaccaagaaccaggtcagcctgacctgcctggt caaaggcttctatcccagcgacatcgccgtggagtgggagagcaatgggcagccggagaacaactacaag accacgcctcccgtgctggactccgacggctccttcttcctctatagcaagctcaccgtggacaagagca ggtggcagcaggggaacgtcttctcatgctccgtgatgcatgaggctctgcacaaccactacacgcagaa gagcctctccctgtctccgggtaaatag LT1009 HC amino acid sequence, with leader (underlined) and minus the hinge region. CDRs are shown in bold. [SEQ ID NO: 24]:

```
  1 mewswvflff lsvttqvhse vqlvqsgaev kkpgeslkis cqsfgyifid 51 htihwmrqmp gqglewmgai sprhditkyn emfrgqvtis adkssstayl 101 qwsslkasdt amyfcarggf ygstiwfdfw gqgtmvtvss astkgpsvfp 151 lapssksts g gtaalgclvk dyfpepvtvs wnsgaltsgv htfpavlqss 201 glyslssvvt vpssslgtqt yicnvnhkps ntkvdkrvap ellggpsvfl 251 fppkpkdtlm isrtpevtcv vvdvshedpe vkfnwyvdgv evhnaktkpr 301 eeqynstyrv vsvltvlhqd wlngkeykck vsnkalpapi ektiskakgq 351 prepqvytlp psreemtknq vsltclvkgf ypsdiavewe sngqpennyk 401 ttppvldsdg sfflyskltv dksrwqqgnv fscsvmheal hnhytqksls 451 lspgk
```

LT1009 LC full length nucleotide sequence [SEQ ID NO: 25] with leader underlined and CDRs in bold; sequences preceding the leader are HindIII cut site (aagctt) and Kozak sequence (gccgccacc):

```
  1 aagcttgccg ccaccatgtc tgtgcctacc caggtgctgg gactgctgct 51 gctgtggctg acagacgccc gctgtgaaac gacagtgacg cagtctccat 101 ccttcctgtc tgcatctgta ggagacagag tcaccatcac ttgcataacc 151 accactgata ttgatgatga tatgaactgg ttccagcagg aaccagggaa 201 agcccctaag ctcctgatct ccgaaggcaa tattcttcgt cctggggtcc 251 catcaagatt cagcagcagt ggatatggca cagatttcac tctcaccatc 301 agcaaattgc agcctgaaga ttttgcaact tattactgtt tgcagagtga 351 taacttacca ttcactttcg gccaaggdac caagctggag atcaaacgta 401 cggtggctgc accatctgtc ttcatcttcc cgccatctga tgagcagttg 451 aaatctggaa ctgcctctgt tgtgtgcctg ctgaataact tctatcccag 501 agaggccaaa gtacagtgga aggtggataa cgccctccaa tcgggtaact 551 cccaggagag tgtcacagag caggacagca aggacagcac ctacagcctc 601 agcagcaccc tgacgctgag caaagcagac tacgagaaac acaaagtcta 651 cgcctgcgaa gtcacccatc agggcctgag ctcgcccgtc acaaagagct 701 tcaacagggg agagtgttag
```

LT1009 LC amino acid sequence with leader underlined and CDRs in bold [SEQ ID NO: 26]:

```
  1 msvptqvlgl lllwltdarc ettvtqspsf lsasvgdrvt itcitttdid 51 ddmnwfqqep gkapkllise gnilrpgvps rfsssgygtd ftltisklqp 101 edfatyyclq sdnlpftfgq gtkleikrtv aapsvfifpp sdeqlksgta 151 svvcllnnfy preakvqwkv dnalqsgnsq esvteqdskd styslsstlt 201 lskadyekhk vyacevthqg lsspvtksfn rgec
```

Sequences of the LT1009 heavy and light chains without leader sequences (and without preceding nuclease cut sites and Kozak sequences) are as follows. CDRs are shown in bold.

LT1009 HC amino acid sequence of the variable domain [SEQ ID NO: 27]:
evqlvqsgaevkkpgeslkiscqsfgyifidhtihwmrqmpgqglewmgaisprhditkynemfrgqvtisadksssstaylqwsslkasdtamyfcarggfygstiwfdfwgqgtmvtvss Corresponding LT1009 HC nucleotide sequence encoding the variable domain [SEQ ID NO: 28]:
gaggtgcagctggtgcagtctggagcagaggtgaaaaagcccggggagtctctgaagatctcctgtcagagttttggatacatctttatcgaccatacta

-continued
ttcactggatgcgccagatgcccgggcaaggcctggagtggatggggct
atttctcccagacatgatattactaaatacaatgagatgttcaggggcca
ggtcaccatctcagccgacaagtccagcagcaccgcctacttgcagtgga
gcagcctgaaggcctcggacaccgccatgtatttctgtgcgagagggggg
ttctacggtagtactatctggtttgacttttggggccaagggacaatggt
caccgtctcttca LT1009 LC amino acid sequence of the variable
domain [SEQ ID NO: 29]:
ettvtqspsflsasvgdrvtitcitttdidddmnwfqqepgkapkllise
gnilrpgvpsrfsssgygtdftltisklqpedfatyyclqsdnlpftfgq
gtkleik Corresponding LT1009 LC nucleotide sequence
encoding the variable domain [SEQ ID NO: 30]:
gaaacgacagtgacgcagtctccatccttcctgtctgcatctgtaggaga
cagagtcaccatcacttgcataaccaccactgatattgatgatgatatga
ctggttccagcaggaaccagggaaagcccctaagctcctgatctccgaa
ggcaatattcttcgtcctggggtcccatcaagattcagcagcagtggata
tggcacagatttcactctcaccatcagcaaattgcagcctgaagattttg
caacttattactgtttgcagagtgataacttaccattcactttcggccaa
gggaccaagctggagatcaaa The amino acid sequences of the full length LT1009 heavy and light chains without leaders are as follows (CDRs are in bold):

LT1009 full length heavy chain amino acid sequence
without leader (and without preceding nuclease
cleavage site and Kozak sequence) and including
hinge (underlined) (SEQ ID NO: 31):
evqlvqsgaevkkpgeslkiscqsfgyifidhtihwmrqmpgqglewmga
isprhditkynemfrgqvtisadkssstaylqwsslkasdtamyfcargg
fygstiwfdfwgqgtmvtvssastkgpsvfplapssktsggtaalgclv
kdyfpepvtvswnsgaltsgvhtfpavlqssglyslssvvtvpssslgtq
tyicnvnhkpsntkvdkrv<u>epkscdkthtcppcp</u>apellggpsvflfppk
pkdtlmisrtpevtcvvvdvshedpevkfnwyvdgvevhnaktkpreeqy
nstyrvvsvltvlhqdwlngkeykckvsnkalpapiektiskakgqprep
qvytlppsreemtknqvsltclvkgfypsdiavewesngqpennykttpp
vldsdgsfflyskltvdksrwqqgnvfscsvmhealhnhytqkslslspg
k LT1009 full length light chain amino acid sequence
without leader. [SEQ ID NO 32]:
ettvtqspsflsasvgdrvtitcitttdidddmnwfqqepgkapkllise
gnilrpgvpsrfsssgygtdftltisklqpedfatyyclqsdnlpftfgq
gtkleikrtvaapsvifppsdeqlksgtasvvcllnnfypreakvqwkv
dnalqsgnsqesvteqdskdstyslsstltlskadyekhkvyacevthqg
lsspvtksfnrgec The corresponding nucleotide sequences (without leaders or preceding nuclease or Kozak sites) are below. It will be understood that due to the degeneracy of the genetic code, alternative nucleotide sequences also may encode virtually any given amino acid sequence.

LT1009 full length heavy chain nucleotide (cDNA)
sequence [SEQ ID NO: 33]:
gaggtgcagctggtgcagtctggagcagaggtgaaaaagcccggggagtc
tctgaagatctcctgtcagagttttggatacatctttatcgaccatacta
ttcactggatgcgccagatgcccgggcaaggcctggagtggatgggggct
atttctcccagacatgatattactaaatacaatgagatgttcaggggcca
ggtcaccatctcagccgacaagtccagcagcaccgcctacttgcagtgga
gcagcctgaaggcctcggacaccgccatgtatttctgtgcgagagggggg
ttctacggtagtactatctggtttgacttttggggccaagggacaatggt
caccgtctcttcagcctccaccaagggcccatcggtcttcccctggcac
cctcctccaagagcacctctgggggcacagcggccctgggctgcctggtc
aaggactacttccccgaaccggtgacggtgtcgtggaactcaggcgccct
gaccagcggcgtgcacaccttcccggctgtcctacagtcctcaggactct
actccctcagcagcgtggtgaccgtgccctccagcagcttgggcacccag
acctacatctgcaacgtgaatcacaagcccagcaacaccaaggtggacaa
gagagtt*gagcccaaatcttgtgacaaaactcacacatgcccaccgtgcc*
cagcacctgaactcctggggggaccgtcagtcttcctcttccccccaaaa
cccaaggacaccctcatgatctcccggacccctgaggtcacatgcgtggt
ggtggacgtgagccacgaagaccctgaggtcaagttcaactggtacgtgg
acggcgtggaggtgcataatgccaagacaaagccgcgggaggagcagtac
aacagcacgtaccgtgtggtcagcgtcctcaccgtcctgcaccaggactg
gctgaatggcaaggagtacaagtgcaaggtctccaacaaagccctcccag
cccccatcgagaaaaccatctccaaagccaaagggcagccccgagaacca
caggtgtacaccctgcccccatcccgggaggagatgaccaagaaccaggt
cagcctgacctgcctggtcaaaggcttctatcccagcgacatcgccgtgg
agtgggagagcaatgggcagccggagaacaactacaagaccacgcctccc
gtgctggactccgacggctccttcttcctctatagcaagctcaccgtgga
caagagcaggtggcagcaggggaacgtcttctcatgctccgtgatgcatg
aggctctgcacaaccactacacgcagaagagcctctccctgtctccgggt
aaatag LT1009 full length light chain nucleotide sequence
[SEQ ID NO 34]:
gaaacgacagtgacgcagtctccatccttcctgtctgcatctgtaggaga
cagagtcaccatcacttgcataaccaccactgatattgatgatgatatga
ctggttccagcaggaaccagggaaagcccctaagctcctgatctccgaa
ggcaatattcttcgtcctggggtcccatcaagattcagcagcagtggata
tggcacagatttcactctcaccatcagcaaattgcagcctgaagattttg
caacttattactgtttgcagagtgataacttaccattcactttcggccaa
gggaccaagctggagatcaaacgtacggtggctgcaccatctgtcttcat
cttcccgccatctgatgagcagttgaaatctggaactgcctctgttgtgt

```
gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgttag
```

The C-Terminal Lysine on the LT1009 Heavy Chain May not Always be Present on the Mature Heavy Chain Protein. While the nucleotide and amino acid sequences for LT1009 heavy chain reveal a lysine as the last (most C-terminal) amino acid residue of the protein, LT1009 when expressed, for example, in CHO cell clone LH1 275, does not contain the C-terminal lysine. This is shown by peptide mapping and, while not wishing to be bound by theory, is believed to result from posttranslational modification of the protein in mammalian systems. Again not wishing to be bound by theory, it is believed that in other expression systems, particularly non-mammalian systems, the C-terminal lysine is present on the mature LT1009 heavy chain.

```
The LT1009 heavy chain amino acid sequence as
expressed in CHO cells (i.e., without leaders and
without the C-terminal lysine) is shown below
(CDRs are in bold, hinge in italics) [SEQ ID NO
35]:
evqlvqsgaevkkpgeslkiscqsfgyifidhtihwmrqmpgqglewmga isprhditkynemfrgqvtisadkssstaylqwsslkasdtamyfcargg fygstiwfdfwgqgtmvtvssastkgpsvfplapsskstsggtaalgclv kdyfpepvtvswnsgaltsgvhtfpavlqssglyslssvvtvpssslgtq tyicnvnhkpsntkvdkrvepkscdkthtcppcpapellggpsvflfppk pkdtlmisrtpevtcvvvdvshedpevkfnwyvdgvevhnaktkpreeqy nstyrvvsvltvlhqdwlngkeykckvsnkalpapiektiskakgqprep qvytlppsreemtknqvsltclvkgfypsdiavewesngqpennykttpp vldsdgsfflyskltvdksrwqqgnvfscsvmhealhnhytqkslslspg
```

An example of a nucleotide sequence that could encode this amino acid sequence is shown below as SEQ ID NO: 36. It will be understood that, due to the degeneracy of the genetic code, multiple nucleotide sequences may encode the same amino acid sequence, and for this reason, these and other nucleotide sequences shown herein as encoding amino acid sequences are recognized to be for purposes of exemplification. CDRs are shown in bold and the hinge region is in italics:

```
gaggtgcagctggtgcagtctggagcagaggtgaaaaagccggggagtc tctgaagatctcctgtcagagttttggatacatctttatcgaccatacta ttcactggatgcgccagatgccgggcaaggcctggagtggatggggct atttctcccagacatgatattactaaatacaatgagatgttcaggggcca ggtcaccatctcagccgacaagtccagcagcaccgcctacttgcagtgga gcagcctgaaggcctcggacaccgccatgtatttctgtgcgagggggg ttctacggtagtactatctggtttgacttttggggccaagggacaatggt caccgtctcttcagcctccaccaagggcccatcggtcttccccctggcac cctcctccaagagcacctctgggggcacagcggccctgggctgcctggtc aaggactacttccccgaaccggtgacggtgtcgtggaactcaggcgccct gaccagcggcgtgcacaccttcccggctgtcctacagtcctcaggactct actccctcagcagcgtggtgaccgtgccctccagcagcttgggcacccag acctacatctgcaacgtgaatcacaagcccagcaacaccaaggtggacaa gagagttggtgagaggccagcacagggagggagggtgtctgctggaagcc aggctcagcgctcctgcctggacgcatcccggctatgcagtcccagtcca gggcagcaaggcaggccccgtctgcctcttcacccggaggcctctgcccg ccccactcatgctcagggagagggtcttctggcttttccccaggctctg ggcaggcacaggctaggtgcccctaacccaggccctgcacacaaagggc aggtgctgggctcagacctgccaagagccatatccgggaggaccctgccc ctgacctaagcccaccccaaaggccaaactctccactccctcagctcgga caccttctctcctcccagattccagtaactcccaatcttctctctgcaga gcccaaatcttgtgacaaaactcacacatgcccaccgtgcccaggtaagc cagcccaggcctcgccctccagctcaaggcgggacaggtgccctagagta gcctgcatccagggacaggccccagccgggtgctgacacgtccacctcca tctcttcctcagcacctgaactcctgggggggaccgtcagtcttcctcttc cccccaaaacccaaggacaccctcatgatctcccggacccctgaggtcac atgcgtggtggtggacgtgagccacgaagaccctgaggtcaagttcaact ggtacgtggacggcgtggaggtgcataatgccaagacaaagccgcgggag gagcagtacaacagcacgtaccgtgtggtcagcgtcctcaccgtcctgca ccaggactggctgaatggcaaggagtacaagtgcaaggtctccaacaaag ccctcccagcccccatcgagaaaaccatctccaaagccaaaggtgggacc cgtggggtgcgagggccacatggacagaggccggctcggcccaccctctg ccctgagagtgaccgctgtaccaacctctgtccctacagggcagccccga gaaccacaggtgtacaccctgcccccatcccgggaggagatgaccaagaa ccaggtcagcctgacctgcctggtcaaaggcttctatcccagcgacatcg ccgtggagtgggagagcaatgggcagccggagaacaactacaagaccacg cctcccgtgctggactccgacggctccttcttcctctatagcaagctcac cgtggacaagagcaggtggcagcaggggaacgtcttctcatgctccgtga tgcatgaggctctgcacaaccactacacgcagaagagcctctccctgtct ccgggttag
```

Peptide Mapping of LT1009

Peptide mapping of LT1009 (four different lots, all expressed in CHO cell line LH1 275) was able to confirm >99% of the protein sequence. The only peptides not observed were single amino acids. Evidence of a deglycosylation reaction was present in fragment T23 of the heavy chain, wherein asparagine (N) was converted to aspartic acid (D) upon deglycosylation. This indicates prior glycosylation at this site, which corresponds to amino acid 301 (N) of the heavy chain amino acid sequence (as shown in, for example, SEQ ID NO: 31). It was also shown by peptide mapping that the C-terminal lysine was not present in the LT1009 heavy chain as expressed in CHO cell line LH1 275.

Example 9

In Vivo Efficacy of Murine mAb (Sphingomab) Vs, Humanized mAb (Sonepcizumab)

Sphingomab (LT1002) and Sonepcizumab (LT1009) were compared in an assortment of animal and in vitro models as disclosed in U.S. patent application Ser. No. 11/924,890, filed on Oct. 26, 2007, entitled "Compositions and Methods for Binding Sphingosine-1-Phosphate," which is incorporated herein in its entirety.

The humanized antibody variants and the murine antibody were compared for their ability to inhibit neo-vascularization in the CNV animal model of AMD. Three of the humanized variants inhibited angiogenesis essentially equivalently to the murine antibody as assessed by measurement of CNV area. Both the murine mAb LT1002 (Sphingomab™) and the humanized mAb LT1009 (Sonepcizumab™) significantly decreased lesion size in this mouse model of CNV. All mAbs tested showed approximately 80-98% reduction of lesion size, which was significant ($p<0.001$ vs. saline) in all cases. In addition, LT1007 and LT1009 also showed significant inhibition ($p<0.05$) compared to non-specific antibody control. Percent inhibition of lesion size was approximately 80% for LT1002 (murine), 82% for LT1004 (humanized), 81% for LT1006 and 99% for LT1009. Thus, LT1009 was most active in this in vivo model of neovascularization.

LT1009 was also effective in reducing the development of retinal neovascularization in murine model of retinopathy of prematurity [U.S. patent application Ser. No. 11/924,890, filed on Oct. 26, 2007, entitled "Compositions and Methods for Binding Sphingosine-1-Phosphate," which is incorporated herein in its entirety]. Intravitreal administration of LT1009 (5.0 μg/eye) resulted in a nearly 4-fold reduction in retinal neovascularization compared to saline control.

LT1009 also blocked nearly 80% of VEGF-induced Angiogenesis in a Matrigel plug assay. This reduction is significant ($p<0.05$ compared to VEGF alone) and confirms the potent anti-angiogenic activity of LT1009 and strongly suggest that LT1009 is capable of significantly inhibiting VEGF induced angiogenesis. This finding is consistent with data from Lpath's oncology program whereby that S1P antibody reduced serum levels of several angiogenic factors, including VEGF, in a murine orthotopic breast cancer model.

LT1009 also significantly reduces choroidal neovascularization and vascular leakage following laser rupture of Bruch's membrane. The area of choroidal neovascularization (stained by PECAM-1) was approximately 0.015 mm² for animals treated with LT1009 and approximately 0.03 mm² for saline-treated control animals. This is a 50% reduction in neovascularization (p-0.018). The area of leakage from choroidal neovascularization (stained by fluorescein) was approximately 0.125 mm² for animals treated with LT1009 and approximately 0.2 mm² for saline-treated control animals. This is approximately a 38% reduction (p-0.017) in blood vessel leakage.

These and other results showing efficacy of LT1009 (Sonepcizumab) in models e.g., for angiogenesis and cancer, are disclosed in U.S. patent application Ser. No. 11/924,890, filed on Oct. 26, 2007, entitled "Compositions and Methods for Binding Sphingosine-1-Phosphate," which is incorporated herein in its entirety.

Example 10

Anti-S1P Antibodies LT1002 and LT1009 Decrease Lymphocyte Counts When Administered to c57/bl6 Mice or Cynomologous Monkeys, Respectively Murine Studies with LT1002

The purpose of this study was to determine the toxicity and toxicokinetic profile of the murine anti-S1P monoclonal antibody, LT1002, following daily administration to C57/BL6 mice. The study was conducted by an independent contract laboratory organization, LAB Research, Inc. The LT1002 dosing solutions were administered for 28 consecutive days to animals in each group by bolus intravenous injection via the tail vein (Days 1-14) and then by bolus intraperitoneal injection (Days 15-28), over a period of approximately 0.5-1.0 minute. The treated group animals were dosed with LT1002 at 30, 75 or 200 mg/kg (n=6 per group) and compared to animals treated with PBS as a saline (vehicle) control group.

During the study, animals were monitored for effects on mortality, clinical condition, body weight and food consumption. Blood samples were collected from a subgroup of animals at necropsy for assessment of hematology, coagulation and clinical chemistry. Study animals were euthanized and subjected to a necropsy examination. Selected organs were weighed and a full list of tissues was retained. A histopathology examination was performed on the full tissue list from all control and high dose animals (200 mg/kg/day) and all abnormalities, while target organs were examined on lower dose groups. Blood samples were collected from the toxicokinetic animals (3 animals/sex/group/time point) on Days 1, 14 and 28 and the animals were euthanized and discarded without examination.

Mean lymphocyte counts were significantly ($p<0.001$) reduced in all LT1002-treated dosing groups with a weak dose-response effect. The average lymphocyte counts ($10^9$ cells/L+/−SD) for the control, untreated group were 2.9+/−1.3 (n=6), which were reduced in the 30, 75 and 200 mg/kg groups, respectively to 0.856+/−0.426 (n=6), 0.902+/−0.269 (n=5) and 0.638+/−0.262 (n=4). These data are consistent with those in the example above, showing that, in the murine EAE model of multiple sclerosis, LT1002 caused substantial reductions in lymphocyte counts correlated with reductions in axonal degeneration, demyelination and infiltration of inflammatory cells.

Non-Human Primate Studies

The purpose of this study was to determine the toxicity and toxicokinetic profile of LT1009 when administered to Cynomolgus monkeys in a GLP 28-day safety toxicology study conducted by an independent contract laboratory organization, LAB Research, Inc. LT1009 was administered by 30-minute intravenous infusion every third day for 28 days (10 doses). LT1009 was formulated in vehicle containing 20 mM sodium phosphate, 148 mM sodium chloride, 0.02% polysorbate-80, pH=6.5 for i.v. administration at doses of 3, 10, 30 and 100 mg/kg; For toxicological assessment, blood samples were collected from all animals at several timepoints on Days 1, 16 and 28. In addition, blood was collected from recovery animals 48, 72, 144 and 240 hours following the end of the last dose. Parameters monitored during this study included mortality, clinical signs, body weight, qualitative evaluation of the food consumption, ophthalmology, electrocardiography, and clinical pathology (hematology, clinical chemistry, coagulation and urinalysis). Blood samples were also collected for immunophenotyping assessments, at pretreatment, on the last day of treatment, and on days 35, 42 and at the end of the recovery period. At termination, a macroscopic examination was performed and selected organs were weighed. Histological evaluation of tissues was conducted on all animals.

There was no mortality, treatment-related adverse clinical signs, or toxicologically-significant effects on body weight, ophthalmology or electrocardiography results, or clinical pathology (hematology, coagulation, clinical chemistry and urinalysis) during this study. There were no organ weight changes or macroscopic or microscopic findings to indicate an adverse effect of LT1009. LT1009 formulation every third day over 28 days (10 treatments) to Cynomolgus monkeys, at dose levels of 3, 10, 30 and 100 mg/kg was well tolerated and did not result in any toxicologically significant changes. As such, the No Observed Toxic Effect Level (NOTEL) for LT1009 in this study was considered to be 100 mg/kg.

However, there were significant (p<0.001) reductions in peripheral blood lymphocyte counts at the high dose only (100 mg/kg). Of the 10 animals in the 100 mg/kg cohort, the mean lymphocyte counts ($10^9$ cells/L+/−SD) were 5.61+/− 2.24 before treatment, and were significantly (p<0.001) reduced to 3.18+/−1.25 (n=10) when males (n=5) and females (n=5) were combined for the analysis. This change was reversed during 7 days of recovery and was not considered adverse under the conditions of the study. No test-article related effect was observed on lymphocyte subpopulations following administration of LT1009 at dose level up to and including 30 mg/kg, or apparent relationship between the LT1009 administration and the absolute number of B and NK cells at any of the dose levels tested. On Day 28, the absolute number of T cells showed a statistically significant decrease following administration of 100 mg/kg LT1009 formulation in both males and females, consistent with the reductions in lymphocyte counts. Analysis of the two main T-cell subsets, T-helper (CD4) and T-cytotoxic (CD8), indicated that the observed reduction in T cells was correlated with a decrease in the absolute number of T-helper cells, whereas the T cytotoxic cells were not affected.

These mouse and primate studies indicate that anti-S1P antibody treatment can reduce lymphocyte counts. These findings are consistent with the scientific literature suggesting that S1P is involved in lymphocyte trafficking and egress from primary and secondary lymphoid tissue into the peripheral circulation. Consequently in humans, it is possible that changes in lymphocyte counts could be a pharmacodynamic marker that could indicate in vivo biological activity of the humanized LT1009 drug candidate formulated for systemic administration. Further, it is possible that systemic administration of LT1009 could be used to alter lymphocyte trafficking with resulting lymphopenia necessary for the treatment of multiple sclerosis or other disorders which might benefit from reduced peripheral blood lymphocyte counts.

Example 11

Purification of LT1009 Antibody with low S1P Carry-Over

Generating highly pure, highly qualified antibodies for pre-clinical or clinical use is of paramount importance for therapeutic drug development. In addition to being free of cellular proteins, DNA and viruses, the antibody preparation should also not contain any of the antigen, so the antibody is fully active and able to bind its target when administered to a patient. Normally, purification and formulation of an antibody removes the antigen, but after purification of the anti-sphingosine-1-phosphate (S1P) monoclonal antibody, LT1009, Lpath sometimes observes significant levels of S1P carried over from the antibody production. S1P is a bioactive lipid that is synthesized by mammalian cells, including Chinese Hamster Ovary (CHO) cells. During production of LT1009, e.g., from the transfected CHO cell line LH1 275 (ATCC Accession No. PTA-8422), intracellular pools of S1P can be released into the media as a result of normal cellular signaling and/or as a consequence of cell rupture after cell death. The LT1009 antibody expressed in the cell-conditioned medium (supernatant) is able to bind to this S1P. As production continues, more S1P may be released and accumulate in the supernatant as a complex with LT1009. While not wishing to be bound by theory, it is believed that the more time the antibody has in contact with the S1P in the medium, the more of that extracellular S1P would be bound to the LT1009 and carried over into the antibody preparation. When produced in CHO cells, LT1009 antibody preparations may contain in excess of 0.5 moles (50 mole percent, mol %) of S1P per mole of antibody. Thus in order to reduce the amount of S1P carry-over, steps must be taken in both upstream and downstream processing to minimize the amount of S1P in the crude harvest and to promote removal of that S1P during purification.

S1P Quantification Methods:

The S1P concentrations in various preparations of the LT1009 antibody were measured at WindRose Analytica by RP-HPLC-MS-MS method. Mass spectrometry is rapid and sensitive and, if applied properly, can quantify picogram amounts of analyte. The approach taken in this analytical method is to introduce the S1P into an electrospray mass spectrometer source by reversed phase liquid chromatography (RPC). The RPC step separates the S1P from protein, salts and other contaminants. Following the chromatographic step the S1P is ionized in the source and passed onto an ion trap mass analyzer. All ions except those of the appropriate mass-to-charge ratio (m/z=380) are ejected from the trap. The remaining ions are fragmented in the ion trap and a specific daughter ion (m/z=264) is monitored. The results verify sample identity in three dimensions of analysis: RPC retention time, parent ion m/z of 380, and daughter ion m/z of 264. It is unlikely that any other compound would satisfy all three of these criteria. Additionally, the MS-MS step maximizes signal-to-noise and therefore increases sensitivity significantly. Since there is no extraction step required there is no need for an internal standard. Additionally, the direct injection of sample into the HPLC-MS increases recovery and sensitivity and decreases complexity and analysis time.

For comparison, the concentration of S1P in extracts of selected antibody preparations was determined using a S1P-quantification ELISA. A 4-fold excess of 1:2 chloroform:methanol was added to 1 mg/ml antibody samples to extract the S1P. The aqueous/organic solution was extensively vortexed and sonicated to disrupt antibody-lipid complexes and incubated on ice. After centrifugation, the soluble fraction was evaporated using a speed-vac, and the dried S1P was resuspended in delipidated human serum. The S1P concentration in the resuspended sample was determined by a competitive ELISA using an anti-S1P antibody and a S1P-coating conjugate. The coating conjugate, a covalently linked S1P-BSA, was prepared by coupling a chemically synthesized thiolated S1P with maleimide-activated BSA. For the S1P standard, mono-layer S1P was solubilized in 1% BSA in PBS (137 mM NaCl, 2.68 mM KCl, 10.1 mM Na2HPO4, 1.76 mM KH2PO4; pH 7.4) by sonication to obtain 10 uM S1P (S1P-BSA complex). The S1P-BSA complex solution was further diluted with delipidated human serum to appropriate concentrations (up to 2 uM). Microtiter ELISA plates (Costar, high-binding plate) were coated with S1P-coating material diluted in 0.1 M sodium carbonate buffer (pH 9.5) at 37° C. for 1 hour. Plates were washed with PBS and blocked with PBS/1% BSA/0.1% Tween-20 for 1 hr at room temperature. For the primary incubation, 0.4 ug/mL biotin-labeled anti-S1P antibody, designated amounts of S1P-BSA complex and samples to be tested were added to wells of the ELISA plates. After 1 hour-incubation at room temperature, plates were washed followed by incubation with 100 ul per well of HRP conjugated streptavidin (1:20,000 dilution) for 1 hour at room temperature. After washing, the peroxidase reaction was developed with TMB substrate and stopped by adding 1 M H2S04. The optical density was measured at 450 nm using a Thermo Multiskan EX.

Upstream Processing to Minimize S1P:

For upstream processing, culturing the CHO cells in serum-free medium (Invitrogen, Cat # 10743-029) is essential because serum contains contaminating S1P that could add to that produced by the CHO cells themselves. In addition to use of serum-free medium, harvesting the antibody from the bioreactor prior to extensive cell death will prevent intracellular pools of S1P to be released into the medium. Finally, initiating the downstream processing immediately after harvest minimizes the time the LT1009 spends in the presence of S1P and the amount of lipid carried over to the final preparation. Despite attempts to minimize the S1P levels during upstream processing, significant S1P often remains in the crude harvest which typically ranges between 0.1-0.2 molar ratio (10-20 mol %) of bound S1P per mol of antibody.

Therefore, Lpath developed downstream methods to remove lipids from antibody preparations in order to generate LT1009 material with very low S1P carry-over levels. These methods (described immediately below) were developed by Lpath and transferred to Laureate Pharma, Inc. to incorporate into their processing methods. As a result, the final drug product produced by Laureate has very low levels of bound S1P (<0.4 mol % measured by HPLC-MS-MS).

Downstream Processing to Reduce S1P:

Traditionally, purification of antibodies from cultured supernatant or ascites fluid involves affinity chromatography. This one-step methods uses recombinant protein-A covalently bond to highly cross-linked agarose (GE healthcare, Cat No 17-5199-04). The protein-A acts as a ligand for Fc domains of monoclonal antibodies. Since the protein-A and S1P binding sites are distinct, S1P does not displace when LT1009 binds the protein-A resin. The high affinity for LT1009 and low solubility in aqueous buffers ensures that S1P remains associated with LT1009 even through extensive washes with high salt buffers (see below). Therefore, conventional antibody purification process that included: Protein A Chromatography, Low pH Viral Inactivation, followed by Neutralization, Q Anion Exchange Chromatography, Viral Nanofiltration and Final Ultrafiltration/Diafiltration did not remove co-purified (bound to LT1009) S1P. In order to dissociate S1P from the bound LT1009, Lpath exploits a special feature in the mechanism of binding.

Lpath in-house research demonstrated that S1P binding activity of LT1009 was reduced at pH<4.0, or at pH>8.5. However, conducting Protein A chromatography at pH<4.0 in order to reduce bound S1P was not feasible because antibody will not bind to Protein A resin at such low pH. Therefore, high salt, pH 8.5 wash step was incorporated in protein A chromatography to reduce S1P bound to LT1009. Further studies demonstrated that the high salt buffer (650 mM NaCl) and 50 mM Sodium Phosphate buffer pH 8.5 did not effectively remove S1P from LT1009. Further increasing of salt concentration from 0.65 M to 1 M (pH 8.5) and extending of the high salt wash step from four column volumes to five column volumes did not yield product with lower bound S1P.

Use of metal chelators to remove S1P: Lpath developed a method that involved premixing of two volumes of crude LT1009 antibody harvest, produced from CHO cells bioreactor campaign, with one volume of Protein A IgG binding buffer ("Pierce binding buffer," Pierce Protein Research Products, Thermo Fisher Scientific, Rockford Ill.), containing 50 mM Potassium Phosphate, 1M NaCl, 2 mM EDTA and 5% glycerol, pH 8.0. According to this procedure the Protein A column was equilibrated with Pierce binding buffer, loaded with premixed crude harvest and washed with 10 column volumes of the same binding buffer. The resulting purified LT1009 contained 2-fold less mole percent of S1P as judged by the S1P-quantification ELISA.

It is currently believed that a metal chelator (e.g., EDTA) is important or even essential for effective reduction of S1P carryover in LT1009 antibody preparations. Indeed, titration of LT1009 with EDTA, which chelates divalent metal cations, abrogates S1P binding. The ability of EDTA to dissociate S1P from LT1009 is believed to facilitate removal of S1P during purification of LT1009. Addition of 2 mM EDTA in the binding and washing buffers effectively lowered the S1P carryover twofold in the eluted antibody fractions. It should be noted that the S1P levels in this study are relatively low initially, and including EDTA should produce greater reduction in lipid carryover in samples with higher initial S1P levels. Without being limited by the following examples, other metal chelators such as EGTA, histidine, malate and phytochelatin may be useful in dissociating S1P from the antibody. EGTA and EDTA are presently preferred divalent metal chelators for separating S1P from anti-S1P antibodies.

Based on these results, a new high salt buffer was developed by Lpath that was comparable in pH and conductivity to the Pierce buffer, and the new premixing step was incorporated in the LT1009 manufacturing process.

Current Downstream Purification Process Includes:
- Premixing of crude harvest with 4× potassium high salt EDTA buffer (200 mM KPi, 4M NaCl, 8 mM EDTA, 20% glycerol, pH 8.0) in ratio of 2 L crude harvest to 0.182 L KPi high salt-EDTA buffer. This step is intended to disrupt and dissociate S1P from LT1009
- Capture of Crude Harvest-High Salt mix on Protein A column and washing the column with 10 column volumes of High Salt-EDTA buffer to remove S1P
- Elution of LT1009 from Protein A resin at low pH (3.6-3.8)
- Low pH hold of Protein A Eluate at pH 3.6-3.8 for a viral inactivation followed by neutralization of the eluate to neutral pH
- Sartobind Q anion exchange chromatography to remove residual host cell proteins and nucleotides, as well as any leached protein A.
- Nanofiltration using Virosart CPV nanofilter as an additional step for virus removal
- Final UF/DF filtration for protein concentration and final formulation Use of low pH and C8 resins to remove S1P: In addition to the use of metal chelators such as EDTA during the purification, one can also exploit the hydrophobic nature of S1P to remove the lipid from purified antibody preparations. This method involves a two-step process: 1) dissociation of the lipid from the antibody, and 2) physical separation of the lipid from the aqueous environment. The applicant employs a pH induced Lipid removal (pHiL) treatment as an easy, robust method to promote dissociation from antibody preparations. Antibodies generally exhibit markedly reduced antigen-binding affinity at low pH. Antibodies generated against phospholipids (e.g. S1P and LPA) fail to bind lipids at pH 3.0-3.5, depending on the specific antibody and the lipid. In determining the correct pH to promote dissociation, a pH titration experiment should be performed to determine the pH that abrogates binding yet maintains an intact IgG, such that binding activity is restored once the pH is increased. In other words the antibody should not be irreversibly inactivated. Once this pH has been determined, the antibody is dialyzed against buffer below the critical pH (e.g. 50 mM sodium acetate, pH 3.0-3.5) at 4° C. Under these conditions, both the lipid and antibody exist as isolated components in solution. The dialyzed solution is passed through a material, such as C8 silica resin (e.g., SepPak cartridges, Waters, Cat no WAT036775), that binds the lipid and facilitates separation of the protein free of lipid. As a consequence, the free lipid irreversibly binds the hydrophobic resin (in the case of C8 silica resin) while the antibody flows through without significant loss (~90% recovery). Most of the lipid can be removed with one pass through the cartridge, but modest gains in lipid removal can be achieved with an additional pass (Table 7).

The metal chelation and pHiL methods described above can easily be incorporated into a single purification procedure. EDTA is compatible with most buffers and does not adversely affect antibody stability, solubility or protein-A binding. During purification, washing the bound IgG with copious amount of EDTA-containing buffer will remove a portion of the S1P from the S1P-LT1009 complex as well as potentially dissociate other metal-dependant antigens-antibody complexes. If the EDTA wash does not sufficiently remove the lipid, the eluate from the protein-A column can be treated using the pHiL method. Elution of bound IgG from protein-A is typically achieved using low pH buffers (pH<3.0). If the anti-lipid antibody elutes from the column at a pH or below the critical pH for lipid binding, the sample can simply be applied to the C8 silica resin to remove the lipid. If necessary, the pH can be easily adjusted prior to applying it to the resin.

TABLE 7

Lipid removal using pHiL method

| Monoclonal Antibody | Mole percent of lipid in sample (relative to amount of antibody) | | | Antibody Recovery % Yield (after 1st treatment) |
| --- | --- | --- | --- | --- |
| | Before treatment | After 1st treatment | After 2nd treatment | |
| Murine Anti-S1P | 60% | 6.3% | 0.97% | 88% |
| Humanized Anti-S1P | 46% | 4.3% | 0.81% | 89% |
| Humanized Anti-LPA | 14 | 4.5 | 6.0 | 91% |

Example 12

Formulations Containing the Humanized Monoclonal Antibody LT1009

1. Introduction

This example describes experiments to assess the stability of several formulations containing the humanized monoclonal antibody LT1009, which is reactive against the bioactive signaling lipid sphingosine 1-phosphate (S1P). LT1009 is an engineered full-length IgG1k isotype antibody that contains two identical light chains and two identical heavy chains, and has a total molecular weight of about 150 kDa. The complementarity determining regions (CDRs) of the light and heavy chains were derived from a murine monoclonal antibody generated against S1P, and further include a Cys to Ala substitution in one of the CDRs. In LT1009, human framework regions contribute approximately 95% of the total amino acid sequences in the antibody, which binds S1P with high affinity and specificity.

The purpose of the testing described in this example was to develop one or more preferred formulations suitable for systemic administration that are capable of maintaining stability and bioactivity of LT1009 over time. As is known, maintenance of molecular conformation, and hence stability, is dependent at least in part on the molecular environment of the protein and on storage conditions. Preferred formulations should not only stabilize the antibody, but also be tolerated by patients when injected. Accordingly, in this study the various formulations tested included either 11 mg/mL or 42 mg/mL of LT1009, as well as different pH, salt, and nonionic surfactant concentrations. Additionally, three different storage temperatures (5° C., 25° C., and 40° C.) were also examined (representing actual, accelerated, and temperature stress conditions, respectively). Stability was assessed using representative samples taken from the various formulations at five different time points: at study initiation and after two weeks, 1 month, 2 months, and 3 months. At each time point, testing involved visual inspection, syringeability (by pulling through a 30-gauge needle), and size exclusion high performance liquid chromatography (SE-HPLC). Circular dichroism (CD) spectroscopy was also used to assess protein stability since above a certain temperature, proteins undergo denaturation, followed by some degree of aggregate formation. The observed transition is referred to as an apparent denaturation or "melting" temperature ($T_m$) and indicate the relative stability of a protein.

2. Materials and Methods a. LT1009

The formulation samples (~0.6 mL each) were generated from an aqueous stock solution containing 42 mg/mL LT1009 in 24 mM sodium phosphate, 148 mM NaCl, pH 6.5. Samples containing 11 mg/mL LT1009 were prepared by diluting a volume of aqueous stock solution to the desired concentration using a 24 mM sodium phosphate, 148 mM NaCl, pH 6.5, solution. To prepare samples having the different pH values, the pH of each concentration of LT1009 (11 mg/mL and 42 mg/mL) was adjusted to 6.0 or 7.0 with 0.1 M HCl or 0.1 M NaOH, respectively, from the original 6.5 value. To prepare samples having different NaCl concentrations, 5 M NaCl was added to the samples to bring the salt concentration to either 300 mM or 450 mM from the original 148 mM. To prepare samples having different concentrations of nonionic surfactant, polysorbate-80 was added to the samples to a final concentration of either 200 ppm or 500 ppm. All samples were aseptically filtered through 0.22 µm PVDF membrane syringe filters into sterile, depyrogenated 10 mL serum vials. The vials were each then sealed with a non-shedding PTFE-lined stopper that was secured in place and protected from contamination with a crimped on cap. Prior to placement into stability chambers, the vials were briefly stored at 2-8° C.; thereafter, they were placed upright in a stability chamber adjusted to one of three specified storage conditions: 40° C. (±2° C.)/75% (±5%) relative humidity (RH); 25° C. (±2° C.)/60% (±5%) RH; or 5° C. (±3° C.)/ambient RH. A summary of the formulation variables tested appears in Table 8, below.

TABLE 8

Formulation Summary

| LT1009, 11 mg/mL | | | LT1009, 42 mg/mL | | |
|---|---|---|---|---|---|
| Polysorbate 80 | NaCl | pH | Polysorbate 80 | NaCl | pH |
| 0.02% Polysorbate | 148 mM NaCl | 7<br>6.5<br>6 | 0.02% Polysorbate | 148 mM NaCl | 7<br>6.5<br>6 |
|  | 300 mM NaCl | 7<br>6.5<br>6 |  | 300 mM NaCl | 7<br>6.5<br>6 |
|  | 450 mM NaCl | 7<br>6.5<br>6 |  | 450 mM NaCl | 7<br>6.5<br>6 |
| 0.05% Polysorbate | 148 nM NaCl | 7<br>6.5<br>6 | 0.05% Polysorbate | 148 mM NaCl | 7<br>6.5<br>6 |
|  | 300 mM NaCl | 7<br>6.5<br>6 |  | 300 mM NaCl | 7<br>6.5<br>6 |
|  | 450 mM NaCl | 7<br>6.5<br>6 |  | 450 mM NaCl | 7<br>6.5<br>6 | b. Taking of Samples

Samples of each formulation were analyzed according to the schedule listed in Table 9, below. One vial was used for each storage condition for all time points. On a date when samples were to be taken, vials were pulled from each stability chamber and 150 μL of each sample were transferred into correspondingly labeled separate vials that were placed on the bench for 1 hour prior to testing. The original vial was immediately placed back into the specified stability chamber after withdrawing the aliquot to be tested.

TABLE 9

Drug Product Formulation Study Stability Matrix

| Protein Concentration Storage Conditions | Intervals (months) | | | | |
|---|---|---|---|---|---|
|  | T = 0 | 0.5 | 1 | 2 | 3 |
| LT1009, 11 mg/mL | | | | | |
| 40° C. | x, y | x, y | x | x | x, y |
| 25° C. | x, y | x, y | x | x | x, y |
| 5° C. | x, y | x, y | x | x | x, y |
| LT1009, 42 mg/mL | | | | | |
| 40° C. | x, y | x, y | x | x | x, y |
| 25° C. | x, y | x, y | x | x | x, y |
| 5° C. | x, y | x, y | x | x | x, y | x = Appearance, pH, SDS-PAGE, SE-HPLC, UV OD-280, IEF
y = Syringeability (performed by aseptically drawing 200 μL of a sample with a 30-gauge needle connected to a disposable 1-mL syringe)

c. Analytical Procedures

For a given time point, aliquots from each sample were subjected to a series of standard analyses, including visual inspection, syringeability, pH, SDS-PAGE (under both reducing and non-reducing conditions), SE-HPLC, and IEF. Protein concentrations were determined by UV spectroscopy (OD-280). Circular dichroism (CD) studies were also performed.

Circular dichroism spectroscopy was performed separately from the formulation studies. An Aviv 202 CD spectrophotometer was used to perform these analyses. Near UV CD spectra were collected from 400 nm to 250 nm. In this region, the disulfides and aromatic side chains contribute to the CD signals. In the far UV wavelength region (250-190 nm), the spectra are dominated by the peptide backbone. Thermal denaturation curves were generated by monitoring at 205 nm, a wavelength commonly used for b-sheet proteins. Data was collected using 0.1 mg/ml samples with heating from 25° C. to 85° C. Data were collected in 1° C. increments. The total time for such a denaturation scan was between 70 and 90 minutes. The averaging time was 2 seconds.

3. Results and Discussion

For all samples analyzed, visual appearance did not change over time. Likewise, syringeability testing demonstrated that samples could be pulled into a syringe equipped with a 30-gauge needle without difficulty. The results of the various analytical tests were consistent, and SE-HPLC was determined to be an excellent stability-indicating method for LT1009. These results showed that increasing salt concentration reduced both the generation of aggregates and the generation of smaller non-aggregate impurities. It was also found that decreasing pH also reduced aggregate and impurity formation. In addition, it was determined that increasing the polysorbate-80 concentration above 200 ppm did not further stabilize LT1009. The SE-HPLC experiments were performed on samples containing 11 mg/mL LT1009, and comparable results were obtained for samples containing 42 mg/mL LT1009, although lower LT1009 concentrations showed less potential for aggregate formation as compared to the higher concentration, indicating that the antibody appeared to be slightly less stable under all conditions tested at the higher concentration.

From the circular dichroism studies, it was found that LT1009 adopts a well-defined tertiary structure in aqueous solution, with well-ordered environments around both Tyr and Trp residues. It also appeared that at least some of the disulfides in antibody molecules experience some degree of bond strain, although this is not uncommon when both intra- and inter-chain disulfides are present. The secondary structure of LT1009 was found to be unremarkable, and exhibited a far UV CD spectrum consistent with β-sheet structure. The observed transition is referred to as an apparent denaturation or "melting" temperature ($T_m$). Upon heating, LT1009 displayed an apparent $T_m$ of approximately 73° C. at pH 7.2. The apparent $T_m$ increased to about 77° C. at pH 6.0. These results indicate that a slightly acidic pH could enhance long-term stability of aqueous formulations of LT1009. Addition of NaCl and/or polysorbate-80 also provided additional stabilization.

Together, the data from these experiments indicate that LT1009 is most stable around pH 6 and 450 mM NaCl independent of antibody concentration. Indeed, SE-HPLC testing indicated that increasing the salt concentration to 450 mM and decreasing the pH to 6.0 while maintaining the polysorbate-80 concentration at 200 ppm had a very beneficial effect on the stability of LT1009. Inclusion of polysorbate-80 above 200 ppm had no further mitigating effect against aggregate formation, probably because it was already above its critical micelle concentration at 200 ppm. While not wishing to be bound by any particular theory, the fact that aggregate formation in LT1009 was reduced with increasing salt concentration under the studied conditions could indicate that aggregate formation is at least in part based more on ionic interactions between molecules rather than hydrophobic interactions. The observation that lowering the pH from 7 to 6 also reduces aggregate formation could be explained by reduced hydrophobicity of the amino acid histidine at the lower pH. Finally, the observed increased tendency of aggregate formation at increased LT11009 concentration can simply be explained by the greater chance of molecules hitting each other at the right time at the right place for aggregate formation.

As these experiments show, a preferred aqueous LT1009 formulation is one having 24 mM phosphate, 450 mM NaCl, 200 ppm polysorbate-80, pH 6.1. The relatively high tonicity of this formulation should not pose a problem for systemic applications since the drug product will likely be diluted by injection into iv-bags containing a larger volume of PBS prior to administration to a patient.

Example 13

Production and Purification of Anti-S1P and Anti-LPA Antibodies

Because X-ray crystallography requires substantial amounts of material, a stable CHO cell line that produces >0.5 mg/L of anti-S1P antibody is used. While maintaining a viability of >95%, cells are seeded at a density of $0.4 \times 10^6$ cells/ml into 1 liter shaker flasks with 500 ml of CD-CHO medium (Invitrogen, San Diego, cat. No. 10743-029) containing 25 µM L-methionine sulphoximine (Sigma, St. Louis Mo., Cat. No. M5379). Cells are grown in an atmosphere of 7.5% $CO_2$ for ten days or until the viability dropped to 45-50%. Supernatants are then harvested by centrifugation at 1500 rpm for 10 minutes and sterile-filtered through a 0.22 micron filter system (Corning, Lowell Mass., cat no. 431098). The clarified supernatants are concentrated tenfold using a Labscale Tangential Flow Filtration system installed with a Pellicon XL Biomax 50 cartridge (Millipore, Billerica Mass., Cat. no PXB050A50) according to manufacturer's protocol assuring that all tubing and vessels were cleaned prior to use with 0.5% NaOH and thoroughly rinsed with DNase and RNase-free distilled water (Invitrogen, San Diego Calif., cat no. 10977-015).

Clarified, concentrated supernatants were diluted with equal volumne IgG binding buffer (Pierce, Rockford Ill., cat. no. 21001) and applied to a gravity-flow column packed with ProSep-vA-Ultra resin (Millipore, cat. no. 115115827) equilibrated with 5 column volumes of binding buffer. The flow through was collected and the bound IgG was washed with 10-15 column volumes of binding buffer. The bound IgG was eluted with elution buffer (Pierce, cat no. 21004) and collected in 40 ml fractions containing 5 ml of binding buffer to neutralize the pH. Fractions with a absorption at 280 nm (A280) of greater than 0.1 were pooled and concentrated using an Amicon stirred cell equipped with a 50 kDa molecular weight cut off (MWCO) filter (Millipore, Cat No PBQK07610). The concentrated antibody was extensively dialyzed against 1×PBS (Cellgro, Manassas Va., Cat No 21-040), filtered through a 0.22 uM syringe-driven filter unit (Millipore, Cat No SLGP033RS) and stored at 4° C.

Anti-LPA antibody is produced and purified in substantially the same manner as the S1P antibody.

Example 14

Isolation of Fab Fragments from Anti-S1P and Anti-LPA Monoclonal Antibodies

Treatment of purified whole IgG preparations with the protease papain separates a Fab fragment consisting of both variable domains and the Ck and Ch1 constant domains from the Fc domain, which contains a pair of Ch2 and Ch3 domains. The Fab fragment retains one entire variable region and, therefore, serves as a useful tool for biochemical characterization of a 1:1 interaction between the antibody and epitope. Furthermore, because it lacks the flexibility and, generally, the glycosylation inherent in native purified whole IgG, the Fab fragment is generally an excellent platform for structure studies via single crystal x-ray diffraction.

Purified, intact anti-S1P IgG was digested with activated papain (incubated 10 mg/ml papain in 5.5 mM cysteine-HCL, 1 mM EDTA, 70 µM 2-mercaptoethanol for 0.5 hours at 37° C.) in digestion buffer (100:1 LT1009:papain in 50 mM sodium phosphate pH 7.2, 2 mM EDTA). After 2 hours at 37° C., the protease reaction was quenched with 50 mM iodoacetamide, dialyzed against 20 mM TRIS pH 9, and loaded onto 2×5 ml HiTrap Q columns. The bound protein was eluted with a linear gradient of 20 mM TRIS pH 8, 0.5 M NaCl and collected in 4 ml fractions. The fractions containing the anti-S1P Fab fragment were pooled and loaded onto a protein A column equilibrated with 20 mM TRIS pH 8. The intact antibody and the Fc fragment bound to the resin, while the Fab fragment was present in the flow through fraction. The Fab fragment was concentrated using a centricon-YM30 centrifugal concentrator (Millipore, Cat No 4209), dialyzed against 25 mM HEPES pH 7, and stored at 4° C. The anti-LPA Fab fragment is prepared similarly.

Example 15

Formation of the Fab/Lipid Complexes

The concentration of the isolated Fab fragment was calculated from the $A_{280}$ value using an extinction coefficient of 1.4 ml/mg. A 5-fold molar excess of 1 mM S1P (Avanti, Cat No 860429P) suspended in methanol was dried in 13×100 mm borosilicate glass tubes by holding in a low vacuum for three hours. The lipids were resuspended in 500 µL of purified anti-S1P Fab by pipetting and filtered through a 0.22 µm Costar Spin-X centrifugal cellulose acetate filter (Corning, Cat No 8160). The complex is concentrated to approximately 12 mg/ml using the centriprep-10 centrifugal concentrator (Millipore). The concentrated Fab/lipid complexes were stored at 4° C. Similarly, Fab/LPA complexes are prepared using LPA (Avanti, Cat No 857120×) and isolated LPA Fab.

Example 16

Crystallization of the Fab/Lipid Complexes

For both Fab/lipid complexes, initial crystallization conditions were determined by the use of a sparse matrix screen (Hampton Research, Aliso Viejo Calif.) and the hanging drop vapor diffusion method. In the case of the Fab/S1P complex, single crystals suitable for diffraction studies were grown at room temperature. 1 microliter of 12 mg/ml Fab/S1P complex was mixed with 1 microliter of reservoir solution containing 22% (w/v) polyethylene glycol 3350, 100 mM $MgSO_4$, 100 mM sodium citrate (pH 6.0) and 10% (v/v) ethylene glycol and sealed over 1 milliliter of reservoir solution. Crystals grew to a final size of 0.2×0.2×0.2 mm in two days. The crystals were harvested from the crystallization drop with nylon loops and flash cooled directly in liquid nitrogen.

Example 17

X-Ray Crystallography

X-ray crystallography is a powerful tool that enables researchers to visualize the mechanisms of molecular recognition at the atomic level. This information is extremely valuable to understand the mode of action for therapeutic antibodies as well as engineer antibodies for enhanced binding characteristics or novel antigen specificities. A combination of x-ray crystallography with innovative biochemical methods is used herein to study two monoclonal antibodies that specifically recognize two bioactive lipids. In addition, these techniques will be used to engineer antibodies with novel specificities for other lipids. This technology grants researchers new tools for studying lipid pathways, metabolism and signaling and hopefully arms clinicians with powerful new weapons against lipid-based pathologies. As lipidomics emerges as an important field in medicine and as more bioactive lipids become implicated in human disease, antibodies that recognize lipids and other non-proteinaceous targets will likely play a significant role in biomedical research.

Due to the structural flexibility and heterogeneity in glycosylation of intact IgGs, the structural studies proposed here focus on the isolated Fab fragments from the anti-S1P and anti-LPA antibodies. High-resolution structures comprising the Fab domain in complex with the lipid target contain sufficient information to elucidate the structural basis for S1P and LPA recognition by their cognate antibodies.

1. X-ray Diffraction Data Collection and Processing. For the Fab/S1P complex, complete X-ray diffraction data was collected at 100 K on an R-Axis IV++ image plate detector (Rigaku, The Woodlands, Tex.) at the San Diego State University Macromolecular X-ray Crystallography Facility (MXCF). X-rays were produced by an RU-H3R rotating anode x-ray generator functioning at 100 mA and 50 kV with Osmic Blue confocal optics (Rigaku). Data indexing and scaling were carried out using HKL2000. Otwinowski, Z. and W. Minor (1997) Methods Enzymol. 276:307-326. Cryo-cooled crystals were tested on the San Diego State University Macromolecular X-ray Crystallography Facility and were observed to diffract x-rays to beyond 2.7 Å resolution (FIG. 1c). The data coordinates for this crystal are provided in U.S. application Ser. No. 12/631,784, filed 4 Dec. 2009, the contents of which are hereby incorporated by reference in their entirety. Data of this quality are suitable for structure determination and a complete set of diffraction intensities have been collected (93.1% completeness overall, 86.2% in highest resolution shell; greater than 3.3-fold redundancy on average throughout all data shells; overall I/sigma 8.7, I/sigma for highest resolution shell 2.7; overall Rsym 12.9%, Rsym in highest resolution shell 47.1%).

Figure 3:
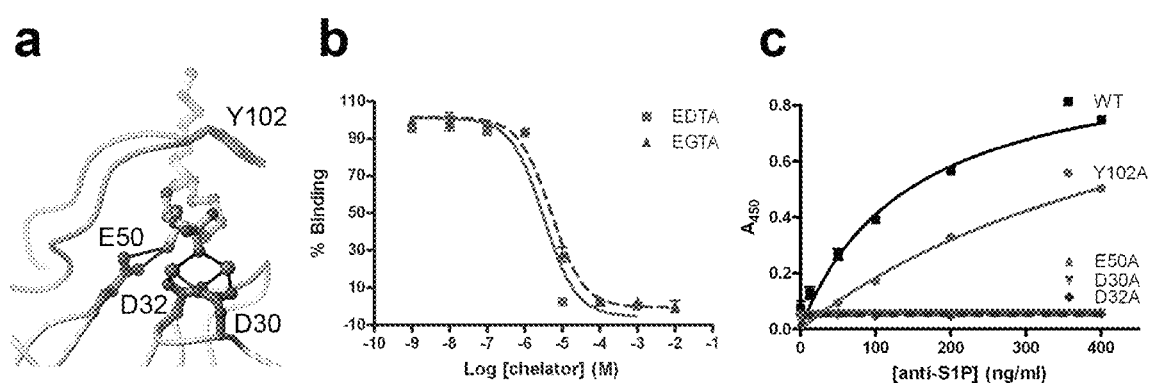

3. Overall Complex Structure:

The LT1009 Fab fragment structure exhibits the standard immunoglobulin domain folds. The structural novelty of the antibody derives from its high affinity binding of the bioactive lipid ($K_D$=10-5-nM) and the direct participation of a pair of $Ca^{2+}$ ions in S1P binding, as shown in FIG. 3a. This is believed to be the first known example of metal ions bridging an antibody and its epitope in a crystal structure.

In its complex-bound state the S1P ligand adopts a slightly curled conformation as it perfectly fits the refined electron density with near ideal stereochemistry, bond lengths, and angles. In addition to the two bridging metal ions, the most striking feature of the S1P:LT1009Fab complex structure is the extent (approx. 70%) to which the ligand is almost completely engulfed by its antibody. The exposed portions include most of the phosphate head group and the terminal carbon atom of the hydrocarbon tail, which was the point of attachment when the derivatized S1P hapten was prepared for immunization. Thus, the LT1009 Fab intimately contacts nearly all of the S1P atoms.

In an effort to determine the source of the metal ions in our refined structure, we have carried out inductively coupled plasma (ICP) spectroscopy on the complexes in solution. These studies reveal the presence of $Ca^{2+}$ at roughly a 2:1 stoichiometric ratio to the complex in the proteins prior to crystallization. No $Mg^{2+}$ or $Mn^{2+}$ ions are present in these complexes. This result indicates that the two ions or $Ca^{2+}$ that we observe in the x-ray structure are inherent to the antibody/ligand complex, while the $Mg^{2+}$ ion and ethylene glycol molecule observed in the electron density appear almost certainly as a consequence of the conditions under which the crystals were grown.

Strikingly, these two calcium atoms appear to mediate interactions between side chains of the antibody light chain and the phosphate group of the lipid. This type of metal bridge is extremely unusual in antibody-antigen interactions. Notably, the calcium atoms remain bound throughout the purification of the intact IgG, proteolytic digestion, Fab purification and extensive dialysis, all of which were performed in buffers without calcium added. This apparent strong affinity of LT1009 for calcium is consistent with the crystal structure; all the distances between the calcium atoms and the coordinating oxygen atoms in LT1009 are less than 2.3 Å and exhibit good geometry. In the structure, the metal atoms are coordinated by the side chains of four aspartic acid residues, including two bivalent interactions from aspartic acids D30 and D32 of the CDR L1. (FIG. 3a). Interestingly, when either unbound whole LT1009 IgG or Fab fragments were analyzed by ICP, the amount of detected $Ca^{2+}$ corresponded to less than one metal ion per binding site.

The role of calcium in the LT1009-S1P interaction has been investigated using metal chelating agents. Titration of LT1009 with EDTA, which chelates divalent metals nonspecifically, or EGTA, which chelates Ca2+ specifically, reveals that ~100-fold excess of either chelator abrogates S1P binding (FIG. 3b). While not wishing to be bound by theory, this is likely due to EDTA/EGTA competing with S1P for the bound Ca2+ rather than displacement of the bound metal, since extensive dialysis of LT1009 after spiking the antibody with high concentrations of EDTA does not render the antibody inactive. When whole LT1009 IgG was first pre-incubated with 50 μM EDTA or EGTA, S1P binding could be rescued by the addition of either $Mg^{2+}$ or $Ca^{2+}$. These results suggest that both $Mg^{2+}$ and $Ca^{2+}$ are capable of bridging the LT1009 antibody and its S1P epitope, and illustrate the extremely stable binding of $Ca^{2+}$ in the complex.

The coordination sphere is made up of both amino acid side chains from the LT1009 light chain and the phosphate group of S1P. Both $Ca^{2+}$ are octahedrally coordinated through one terminal syn $\eta^1$ bond from either aspartic acid D31 in the antibody light chain to one calcium (designated Ca1) and from aspartic acid D92 in the antibody light chain to the other calcium (designated Ca2). Two bridging interactions with the side chains of aspartic acids at positions 30 and 32 in the light chain provide another pair of bonds to each metal ion. Two separate pairs of water molecules occupy symmetrically similar positions about the ions providing the fourth and fifth ligands. Finally, an oxygen atom from the phosphate head group of S1P completes the coordination of both ions via a bridge. This ligand arrangement allows the two $Ca^{2+}$ to come within 3.81 Å of each other without any linking atoms directly between them.

In addition to this electrostatic interaction between the two bound $Ca^{2+}$ atoms and the oxygen from the phosphate head group, there are also hydrogen bonds between LT1009 and the amino alcohol region of the S1P. Both the C2-amino and C3-hydroxyl groups of S1P participate in two hydrogen bonds. Only the hydrogen bond between the carboxylic acid group of glutamic acid E50 in the LT1009 light chain and the amino group of S1P involves an amino acid side chain. This interaction is believed to be critical for specificity. The C3-hydroxyl moiety forms hydrogen bonds with the backbone amides of glycine 99 and serine 100, both from CDR-H3.

The remaining contacts between S1P and the LT1009 Fab are hydrophobic in nature. These include amino acid residues leucine L94 and phenylalanine F96 from the light chain and threonine T33, histidine H35, alanine A50, serine S52, histidine H54, isoleucine 156, lysine K58, phenylalanine F97, tyrosine Y98, threonine T100A and tryptophan W100C from the antibody heavy chain (Kabat numbering). Although some of these contain polar or charged side chains, each contributes to create a network of closely packed carbon atoms and create a hydrophobic channel that surrounds the lipid aliphatic tail. The CDR-H3 loop of the heavy chain appears to fold over the top of the lipid upon S1P binding to the antibody, with tyrosine Y98 thought to function as a "gate" or "latch" that passes over the bound S1P molecule and fastens to the side chains of leucine at position 94 of the light chain and lysine at position 58 of the heavy chain through van der Waals forces.

In order to demonstrate a gain of function role for divalent metals in the Fab-S1P interaction, LT1009 Fab binding to an immobilized S1P derivative was measured using Surface Plasmon Resonance (SPR) in the presence and absence of calcium. LT1009 Fab was passed over C18 thiolated S1P (S1P-SH) coated on a ProteOn GLM sensor chip using sulfo-MBS coupling. The results show that the presence of 50 μM $CaCl_2$ significantly promotes complex formation by decreasing the equilibrium dissociation binding constant ($K_D$) over 100 fold (Table 12). These data are entirely consistent with the crystal structure, mutagenesis, and binding studies in the presence of chelators demonstrating that divalent metals, including calcium, play a major role in formation of the LT1009 Fab-S1P complex.

TABLE 10

LT1009 binding to S1P in presence and absence of calcium

| Buffer 10 mM HEPES pH 7.4, 150 mM NaCl, 0.005% tween-20, 0.1 mg/ml BSA | S1P-SH density (RU) | ka ($M^{-1}s^{-1}$) | kd ($s^{-1}$) | $K_D$ (nM) |
|---|---|---|---|---|
| without $CaCl_2$ | 600 | 5.5E+4 | 7.03E−3 | 131 |
| +50 μM $CaCl_2$ | 900 | 3.03E+5 | 3.00E−4 | 0.99 |

Example 18

Mutagenesis and Biochemical Characterization of the Antibody-Lipid Complexes Lpath's Immune Y2 technology provides a powerful, sensitive and robust method for rapidly analyzing the lipid-binding characteristics of many antibody variants. This platform is disclosed in Lpath's patent applications US20070281320, US20080138334 and US20080090303A1, all of which are herein incorporated in their entirety for all purposes.

The Immune Y2 platform relies upon a derivatized bioactive lipid for immunogen preparation and for detection and characterization methods. The highly reactive sulfhydryl group covalently attached to the terminal carbon of the aliphatic lipid chain enables the thiolated S1P and LPA (including C12 and C18 isoforms) to be directly coupled to a surface plasma resonance (SPR) chip or conjugated with a protein (e.g., albumin) to serve as the coating material for enzyme-linked immunosorbent assays (ELISA). With this technology, the antibody-lipid interactions can be studied either directly or via competition between the lipid coated on a plate and other lipids presented in solution. This competition ELISA measures the crossreactivity of either wild type (WT) or mutant antibodies to a variety of structurally related lipids. ELISAS are described in Examples 1 and 2, and below. The ELISA results confirm that the anti-S1P and anti-LPA antibodies LT1009 and LT3015 are highly specific for their lipid targets. The direct-binding ELISA, competition ELISA and SPR methods are used to determine the effect of mutating amino acids in the variable domains of the anti-S1P and anti-LPA antibodies on the ability of those variants to recognize and bind lipids.

1. Production of Antibody Variants

These techniques have several practical advantages, such as the relatively small amounts of material required to perform the experiment. SPR requires only microgram quantities while the direct-binding and competition ELISA use mere nanograms of a particular antibody. Therefore, antibodies harboring essentially any desired mutation can be produced by transiently transfecting HEK 293 cells. These cultures typically produce 10-50 ug/ml of antibody, thereby requiring small quantities of reagents and providing a cost-effective, efficient method to generate sufficient material to fully characterize each antibody variant. Another advantage of these experiments is that binding studies can be performed using the clarified supernatant, thereby eliminating the purification step. However, antibody secreted into the supernatant is easily purified using protein-A affinity chromatography, if desired. Using this production method, several antibody variants can be studied simultaneously. A comprehensive analysis of the amino acids that contact the lipid in the crystal structure can be evaluated to determine their affect on lipid binding and specificity.

a. Mutagenesis. Plasmid constructs containing mutations within the variable domains of the heavy and light chains are created using the QuikChange Site-Directed Mutagenesis Kit (Stratagene, San Diego Calif., Cat. No 200524). Individual reactions are carried out with 50 ng of double-stranded DNA template, 2.5 U of Pfu Ultra HF DNA polymerase and its corresponding buffer (Stratagene, Cat. No 200524), 10 mM dNTP mix and 125 ng of each of the mutagenic oligonucleotides (provided in kit) resuspended in 5 mM Tris-HCl (pH 8.0), and 0.1 mM EDTA. The initial denaturation is carried out at 95° C. for 30 seconds, followed by 16 cycles of amplification: 95° C. for 30 seconds, 55° C. for 1 minute and 68° C. for 8 minutes. Following temperature cycling, the final reaction was then digested with DpnI digest at 37° C. for 1 h to remove methylated parental DNA. The resultant mutants are transformed into competent XL1-Blue *E. coli* and plated on LB-agar containing 50 μg/ml ampicillin. The colonies are screened by DNA sequencing to confirm the presence of the mutation. Each mutant is cultured in 1 liter shake flasks and purified using the EndoFree Plasmid Purification Kit from Qiagen, Valencia Calif. (Cat. No 12362).

b. Expression and Production of Mutant Antibodies in Mammalian Cells. Purified plasmids containing the mutations are transfected into the human embryonic kidney cell line 293F using 293fectin and using 293F-FreeStyle Media (Invitrogen) for culture. Light and heavy chain plasmids are both transfected at 0.5 μg/mL following manufacturer's instructions. The purity and structurally integrity is judged using SDS-PAGE. Under reducing conditions, the expected masses of the heavy and light chains are 25 kDa and 50 kDa, while a single band is observed under non-reducing conditions with the expected mass of ~150 kDa.

c. Purification of Mutant Antibodies. Mutant antibodies expressed from transient transfections are purified using protein-A affinity chromotagraphy as described for the wild-type antibodies. The antibody concentration is determined using quantitative ELISA.

d. Quantitative ELISA. Goat-anti human IgG-Fc antibody (Bethyl, Montgomery Tex., Cat no. A80-104A, 1 mg/ml) is diluted 1:100 in carbonate buffer (100 mM $NaHCO_3$, 33.6 mM $Na_2CO_3$, pH 9.5). Plates are coated with 100 ul/well of coating solution and incubated at 37° C. for 1 hour. The plates are then washed 4× with TBS-T (50 mM Tris, 0.14 M NaCl, 0.05% Tween-20, pH 8.0) and blocked with 200 µl/well TBS/BSA (50 mM Tris, 0.14 M NaCl, +1% BSA, pH 8.0) for 1 hour at 37° C. Samples and standards are prepared on non-binding plates with enough volume to run in duplicate.

The standard is prepared by diluting human reference serum (Bethyl RS10-110; 4 mg/ml) in TBS-T/BSA (50 mM Tris, 0.14 NaCl, 1% BSA, 0.05% Tween-20, pH 8.0) to the following dilutions: 500 ng/ml, 250 ng/ml, 125 ng/ml, 62.5 ng/ml, 31.25 ng/ml, 15.625 ng/ml, 7.8125 ng/ml, and 0.0 ng/ml. The samples are prepared by making appropriate dilutions in TBS-T/BSA so that the samples OD fall within the range of this standard curve, the most linear range being from 125 ng/ml to 15.625 ng/ml. After washing the plates 4 times with TBS-T, 100 µl of the standard/samples preparation is added to each well and incubated at 37° C. for 1 hour. Next, the plates are washed 4 times with TBS-T and then incubated for 1 hour at 37° C. with 100 ul/well of HRP-goat anti-human IgG antibody (Bethyl A80-104P, 1 mg/ml) diluted 1:150,000 in TBS-T/BSA. The plates are washed 4 additional times with TBS-T and developed using 100 µl/well TMB substrate at 4° C. After 7 minutes, the reaction is stopped by adding 100 µl/well of 1 M $H_2SO_4$. The OD is measured at 450 nm. Data is analyzed using Graphpad Prizm software.

e. Direct-Binding ELISA. Microtiter ELISA plates (Costar, Corning Inc., Lowell Mass., Cat No. 3361) are coated overnight with either S1P or LPA conjugated to delipidated BSA diluted in 0.1M Carbonate Buffer (pH 9.5) at 37° C. for 1 h. Plates are washed with PBS (137 mM NaCl, 2.68 mM KCl, 10.1 mM $Na_2HPO_4$, 1.76 mM $KH_2PO_4$; pH 7.4) and blocked with PBS/BSA/Tween-20 for 1 hour at room temp or overnight at 4° C. For the primary incubation (1 hour at room temp.), a dilution curve (0.4 µg/mL, 0.2 µg/mL, 0.1 µg/mL, 0.05 µg/mL, 0.0125 µg/mL, and 0 µg/mL) of the wild-type or mutant antibody is built (100 µl/well). Plates are washed and incubated with 100 µl/well of HRP conjugated goat anti-mouse (1:20,000 dilution) (Jackson Immunoresearch, West Grove Pa., Cat No 115-035-003) or HRP conjugated goat anti-human (H+L) diluted 1:50,000 (Jackson, Cat No 109-035-003) for 1 hour at room temperature. After washing, the peroxidase is developed with Tetramethylbenzidine substrate (Sigma, cat No T0440) and quenched by addition of 1 M $H_2SO_4$. The optical density (OD) is measured at 450 nm using a Thermo Multiskan EX. The raw data is transferred to the GraphPad software and the concentration of lipid that produced half maximal effect ($EC_{50}$) and the maximum binding absorbance (Vmax) is calculated using a 4-parameter nonlinear least squares fit of the saturation binding curves.

f. Lipid Competition Assay. The ability of various lipids in solution to inhibit direct-S1P or direct-LPA binding by the WT/mutant antibodies is tested using an ELISA assay format. Microtiter ELISA plates (Costar, Cat No. 3361) are coated with S1P diluted in 0.1 M Carbonate Buffer (pH 9.5) at 37° C. for 1 hour. Plates are washed with PBS (137 mM NaCl, 2.68 mM KCl, 10.1 mM $Na_2HPO_4$, 1.76 mM $KH_2PO_4$; pH 7.4) and blocked with PBS/BSA/Tween-20 for 1 hour at room temp or overnight at 4° C. For the primary incubation, 0.4 µg/mL of antibody and designated amounts of lipid are added to wells of the ELISA plates and incubated at room temp for 1 hr. Plates are washed and incubated with 100µ per well of HRP conjugated goat anti-mouse (1:20,000 dilution) (Jackson, cat No 115-035-003) or HRP conjugated goat anti-human (H+L) diluted 1:50,000 (Jackson, cat No 109-035-003) for 1 hour at room temperature. After washing, the peroxidase reaction is developed with Tetramethylbenzidine substrate and stopped by adding 1 M $H_2SO_4$. The optical density (OD) is measured at 450 nm using a Thermo Multiskan EX. The maximum binding absorbance (Vmax) and percent inhibition are calculated by linear regression of the Lineweaver-Burke plots using Excel software.

g. Surface Plasmon Resonance. All binding data is collected on a ProteOn optical biosensor (BioRad, Hercules Calif.). Thiolated lipids are coupled to a maleimide modified GLC sensor chip (Cat. No 176-5011). First, the GLC chip is activated with an equal mixture of sulfo-NHS/EDC for seven minutes followed by a 7 minute blocking step with ethyldiamine. Next sulfo-MBS (Pierce Co Rockford, Ill., cat #22312) is passed over the surfaces at a concentration of 0.5 mM in HBS running buffer (10 mM HEPES, 150 mM NaCl, 0.005% tween-20, pH 7.4). The thiolated lipid is diluted into the HBS running buffer to a concentration of 10, 1 and 0.1 µM and injected for 7 minutes producing different lipid density surfaces (~100, ~300 and ~1400 RU). Next, binding data for the WT and mutant antibodies is collected using a 3-fold dilution series starting with 25 nM as the highest concentration. Surfaces are regenerated with a 10 second pulse of 100 mM HCl. All data is collected at 25° C. Controls are processed using a reference surface as well as blank injections. In order to extract binding parameters, the data is globally fit using 1-site and 2-site models.

2. Mutations Designed to Abrogate Lipid Binding

Initially, mutations in the anti-S1P and anti-LPA antibodies are designed to test the x-ray structures with biochemical techniques. Amino acids in the variable domains that directly contact the lipids in the complex are substituted with amino acids designed to reduce binding in the SPR and direct-binding ELISA. The importance of the electrostatic charge, polarity and hydrophobicity of the amino acids are thus investigated. Based on preliminary data, it is presently believed that amino acids recognize the S1P head group using electrostatic and hydrogen bonding interactions, whereas hydrophobic residues stabilize the aliphatic carbon chain of S1P. Therefore, it is believed that mutating residues that contact the lipid head groups to alanine or a residue with opposite charge will abrogate lipid binding. In addition, select residues that form the hydrophobic pocket are substituted with charged, polar residues (such as glutamic acid) designed to dramatically alter the electrostatic surface of the variable domain and sequester water into the hydrophobic binding pocket and dramatically reduce stability of the complex.

These experiments also identify positions in the variable domains that influence lipid binding and specificity. It is currently believed that a limited number of positions in the variable domains provide the major determinants for lipid recognition. At these positions subtle amino acid substitutions (such as glutamine to asparagine) are believed to cause a dramatic effect in lipid binding or specificity. Here, investigations are designed to probe the size of the side chains as well as the role of the framework residues that support the position and orientation of the residues that directly contact the lipids. By ‘fine-tuning’ the antibody-lipid interaction through conservative mutagenesis, it is believed to be possible to improve the overall affinity of the antibodies for their cognate lipids, or improve the lifetime of the complex. This is believed to enhance the therapeutic potential of the antibody by increasing its ability to sequester and neutralize the bioactive lipid target.

Figure 2:
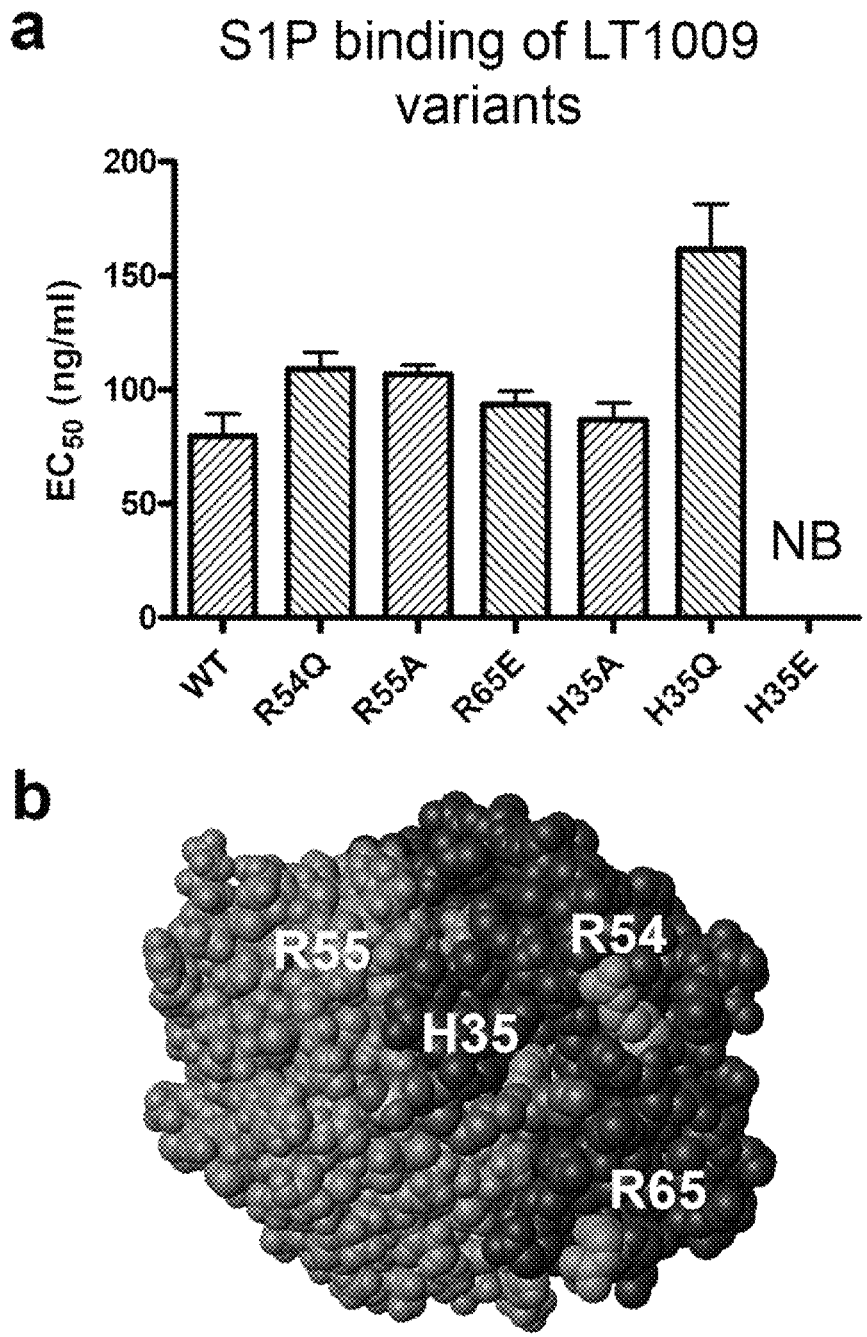
FIG. 2: S1P binding of LT1009 variants.

During development of the humanized monoclonal anti-S1P antibody LT1009, numerous biochemical studies were initiated to characterize S1P binding, crossreactivity, thermostability and solubility, as described above. Several variants of the antibody were designed with point mutations located within the antigen-binding surfaces in the heavy and light chains. These variants were produced, purified and their S1P-binding affinities were measured using the direct-binding ELISA as described above. Mutating several solvent-exposed arginine residues (R55 in CDRL2, R54 in CDRH2, and R65 in CDRH2, using sequential numbering) did not affect the S1P binding affinities (FIG. 2a). However, mutation of histidine H35 in the CDR H1, resulted in markedly altered S1P binding compared to wildtype. Mutation of this residue to an alanine does not significantly change S1P binding, while a variant containing a glutamine substitution at this position exhibits a twofold increase in EC50 (from approximately 80 ng/ml for wildtype to approximately 160 ng/ml for H35Q), indicating decreased S1P binding, and mutation to glutamic acid at this position (H35E) eliminates measurable S1P binding altogether (FIG. 2a). While not wishing to be bound by theory, these data suggest that position 35 in CDR H1 likely forms hydrophobic contacts with S1P in the complex. Indeed, when the positions of the mutations are mapped onto the initial X-ray structures, histidine H35 in the heavy chain appears to pack tightly against the hydrophobic tail of S1P, and substitution to a glutamic acid dramatically alters the electrostatic environment to create an unfavorable binding pocket (FIG. 2b). This is consistent with the observations that the alanine variant, which forms energetically favorable hydrophobic interactions, retains S1P binding. Mutation of tyrosine 98 in the heavy chain to alanine also resulted in a significant decrease in binding. The other LT1009 variants containing arginine mutations (R55 in CDR L2, R54 in CDR H2 and R65 in CDR H2), which do not show significant differences in S1P binding compared to WT, are far removed from the bound S1P in the LT1009Fab/S1P complex. These data demonstrate that the structural and biochemical data are in excellent agreement and suggest that the crystal structures of the LT1009Fab/S1P and LT3015Fab/LPA complexes will provide a reliable structural basis for the understanding of, and manipulation of, particular amino acid residues in the antibodies that serve as the major determinants for lipid recognition.

An interesting feature detected in the LT1009Fab/S1P structure is the position of Y102 in the CDR H3. In the S1P-bound confirmation, the side chain of this tyrosine residue appears to fold over the hydrocarbon tail of S1P, clamping down on the lipid. In this conformation, the lipid is unable to freely dissociate from the antibody. Based on the structure, a conformational change in the CDR H3 or the Y102 side chain rotomer position is believed to take place which allows the lipid to dissociate. While not wishing to be bound by theory, this is believed to play an important role in the lifetime of the LT1009-S1P complex.

To further investigate this 'tyrosine gate' mechanism, position 102 in the CDRH3 was mutated to an alanine and S1P binding of the mutant was measured. The equilibrium S1P binding constant of the Y102A mutant was ~4-fold higher than WT, indicating that the affinity of the mutant for the lipid was significantly reduced. However, the loss of binding was not absolute as with the mutation in the calcium binding site (FIG. 3c). Future experiments using surface plasmon resonance (SPR) are planned to determine whether the kinetic effect of mutating Y102 is greater than at equilibrium. While again not wishing to be bound by theory, it is anticipated that the off-rate of the mutant will be much faster than the wild type antibody.

Finally, the effect of mutating glutamic acid E50 in the LT1009 CDR L2 was investigated; this amino acid has been predicted to form a specific interaction with S1P. Computational studies suggest that the ammonium group in S1P likely contains a +1 charge in the "free" lipid. This is consistent with the observed structure, which shows the ammonium ion forming an electrostatic interaction with the negatively charged side chain of E50 in the CDR L2. We hypothesize that this interaction is likely a major determinant of S1P specificity, and mutating this position would dramatically reduce S1P binding. As expected, mutating this position to an alanine abrogates S1P binding (FIG. 3c). Altogether, these studies validate the LT1009Fab/S1P crystal structure and elucidate the positions in LT1009 that are important for lipid binding.

3. Mutations Designed to Modulate Lipid Specificity

Once the major determinants that govern lipid recognition have been identified, antibody variants are generated and cross-reactivity with other lipids is measured using the competition ELISA. Using molecular modeling software to morph S1P and LPA into structurally related lipid, positions in the variable domains to be substituted are identified. Eventually, libraries of variants will be built up, providing rapid analysis of a variety of lipids. Because the structure space of lipids, including bioactive lipids, is small, the task of modulating the lipid specificity of an antibody is a manageable one, unlike the case for antibodies against protein antigens, which are much larger and more variable in secondary and tertiary structure.

Previous modeling studies on $S1P_1$ identified a single glutamic acid residue that when mutated to glutamine causes the receptor to become activated and internalized by LPA. Wang, D. A., et al. (2001) J Biol Chem, 2001. 276: 49213-20. The same research group also identified a single position in the LPA receptors, $LPA_{1-3}$, where a single glutamine to glutamic acid substitution enables the receptor to become more responsive to S1P. Valentine, W. J., et al. (2008) J Biol. Chem. 283: 12175-87. The modeling studies predict the glutamic acid/glutamine residue interacts with the primary amine group of S1P. Interesting, in the LT1009Fab/S1P complex this moiety forms an analogous electrostatic interaction with glutamic acid E50 in the CDR L2 light chain. Therefore, it is believed that mutating glutamic acid E50 in CDR L2 to a glutamine will cause LT1009 to gain LPA-binding activity. Alternatively, we can substitute the entire CDR L2 from the anti-LPA mAb, since glutamic acid E50 is the only position in CDR L2 that directly contacts the lipid. We believe that the CDRs from either LT1009 or LT3015, or a combination thereof, that contact the lipid phosphate group may be used to design an antibody against other bioactive lipids, particularly lysolipids.

It is also believed that the Vh framework may present a favorable, universal binding pocket for lysolipids. The LT1009 and LT3015 Vh sequences are 93% identical outside the CDRs (as expected, the CDRs have lower identity, in this case 46%). The Vk sequences are 59% identical outside the CDRs (19% identity within the CDRs). In the LT1009Fab/S1P structure, the less conserved Vk domain exclusively contacts the head group of S1P, which is dissimilar to LPA, whereas the highly conserved Vh domain primarily contacts the hydrocarbon chain, which is chemically conserved between S1P and LPA. The fact that the homology among variable domains directly relates to the chemical similarity among lipid regions suggests common mechanisms in antibody-lipid interactions, which we may be able to exploit to generate libraries of CDRs that specifically recognize the various structural and functional groups that distinguish bioactive lipids. By using different combinations of CDRs, it is believed to be possible to develop novel antibodies, in silico, against a wide range of therapeutic targets. The crystal structure disclosed herein for S1P-LT1009 will be used as a template for direction of in silico modeling. Different bioactive lipids are docked in the S1P binding pocket and the antibody will be morphed in silico such that the new antibodies form stabilizing interactions analogous or similar to the ones described herein for LT1009 and S1P. Once additional co-crystals are available (e.g., humanized anti-LPA antibody and LPA), it is envisioned that information from multiple co-crystals, particularly bioactive lipid-antibody co-crystals, may be used together in the design of new anti-lipid antibodies.

It has now been demonstrated that mutating glutamic acid at position 50 of the light chain to a glutamine changes the antibody specificity. While not wishing to be bound by theory, the crystal structure of sphingosine-1-phosphate (S1P) in complex with the Fab fragment of LT1009 suggests that S1P specificity of the antibody may be governed by an interaction with the ammonium group located at the C2 position of the lipid. Under physiological conditions, this moiety is likely positively charged in both in S1P and dihydro S1P, which show high affinity for the Fab, and neutral in sphingosine and sphingosylphosphorylcholine, which have relatively lower affinities for the Fab. In the S1P structure, the ammonium group forms a single, electrostatic interaction with side chain of glutamic acid at position 50, which protrudes from the antibody light chain. These observations invited speculation that changing the amino acid at this position may modulate the antibody's specificity for other lipid targets, such as lysophosphatidic acid (LPA).

Figure 4:
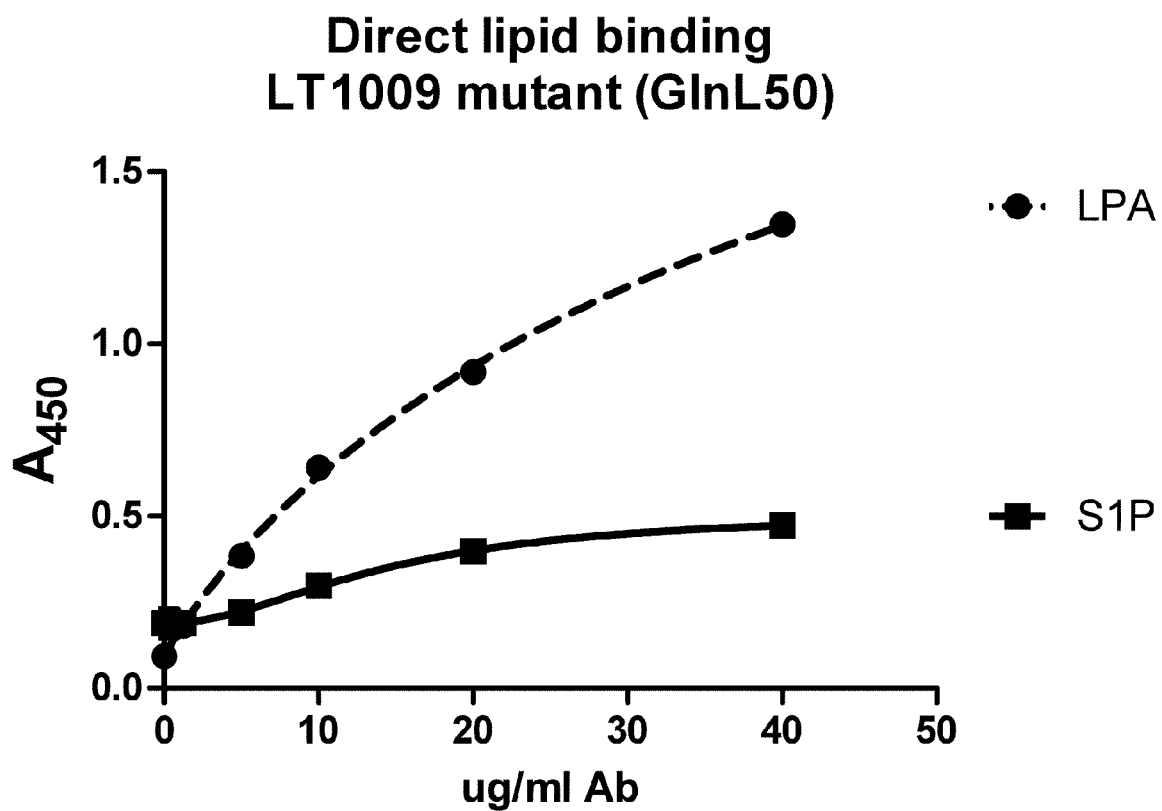

To test this idea, this glutamic acid (GluL50) was mutated to glutamine (GlnL50) and binding of these antibodies to either S1P or LPA was assayed using a direct ELISA. As expected, the wild-type (WT) LT1009 shows high affinity for the S1P-BSA coating material, while no binding activity was observed for C12 LPA-BSA coated on the plate. In contrast, the LT1009 GlnL50 mutant antibody shows significantly higher affinity for the C12 LPA-BSA conjugate compared to S1P-BSA (FIG. 4), suggesting that this amino acid plays a significant role in S1P specificity and changes at this position alters target specificity.

While not wishing to be bound by theory, these results are consistent with the chemical nature of the amino acid side chains and the functional groups in the lipid targets. In the Fab-S1P crystal structure, the positively charged ammonium group of S1P forms an electrostatic interaction with the negatively charged GluL50 side chain. In LPA, the ammonium group is replaced with an uncharged hydroxyl group, so the favorable electrostatic interaction is not available for binding to the WT antibody. The GlnL50 mutation introduces a neutral, polar side chain capable of forming a hydrogen bond with the hydroxyl group of LPA. The presence of this interaction apparently stabilizes binding of the mutant LT1009 to LPA and destabilizes binding to S1P. Thus antibody in silico antibody design has been used here to convert an anti-S1P antibody to an antibody that binds LPA better than it binds S1P.

4. Mutations to Disrupt the Calcium Binding Site:

The effect of the bound calcium in S1P binding was further investigated using site-directed mutagenesis. Aspartic acids D30 and D32 in the CDR L1 were changed to alanine to disrupt the calcium-binding site. Antibodies harboring either of these mutations did not bind any S1P (FIG. 3c). Inductively coupled plasma (ICP) spectroscopy will be used to compare the metal content of the wildtype LT1009 antibody, which measures a 2:1 Ca2+:LT1009 stoichiometry, with the D30A and D32A mutants to confirm the absence of calcium.

Example 19

Specific Intermolecular Contacts Between Antibody (LT1009 Fab) and Ligand (S1P)

Based on the crystal structure determined in previous examples, it is possible to assign roles to many amino acid positions within the LT1009 antibody, in terms of their contacts with the SIP ligand or in metal binding (calcium coordination). These interactions are listed in Table 11.

TABLE 11

Specific intermolecular contacts between the antibody (LT1009 Fab) and the ligand (S1P).

| Residue | Position | Interactions with calcium or S1P |
|---|---|---|
| Asp | L30 | calcium coordination |
| Asp | L31 | calcium coordination |
| Asp | L32 | calcium coordination |
| Glu | L50 | Electrostatic contact with C2 ammonium group |
| Asp | L92 | calcium coordination |
| Leu | L94 | Van der Waals contacts with C8, C10, C12 |
| Phe | L96 | Van der Waals contacts with C6, C8 |
| Thr | H33 | Van der Waals contacts with C13, C14 |
| His | H35 | Van der Waals contacts with C11, C12, C13 |
| Ala | H50 | Van der Waals contacts with C12, C14 |
| Ser | H52 | Van der Waals contacts with C16, C17, C18 |
| His | H54 | Van der Waals contact with C18 |
| Ile | H56 | Van der Waals contacts with C15, C17 |
| Lys | H58 | Van der Waals contacts with C14, C15 |
| Phe | H97 | Van der Waals contacts with C9, C10, C11, C13, C16, C18 |
| Tyr | H98 | Van der Waals contact with C7, C9, C10, C15, C16, C17 |
| Gly | H99 | Hydrogen bond (amide) with C3 hydroxyl group |
| Ser | S100 | Hydrogen bond (carbonyl) with C3 hydroxyl group |
| Thr | H100A | Van der Waals contact with C1 |
| Trp | H100C | Van der Waals contacts with C4, C9, C11 |

Example 20

Additional Variants Designed Based on Antibody:Lipid Co-Crystal Structure

Based on the structural information derived from x-ray analysis of the LT1009 Fab: S1P crystal, additional variants of LT1009 have been designed.

Variants Designed to have Altered Affinity for S1P:

A number of amino acid residues in both the light chain and the heavy chain of LT1009 have been identified as likely to play a role in antibody binding to S1P because these residues are shown to be in contact with the lipid, based on the structure of the antibody-lipid complex. These positions include aspartic acid residue at position 28 (D28), glycine residue G51, leucine residue L94 and phenylalanine residue F96 of the light chain, and histidine residue H35, serine residue S52, proline residue P52A, histidine residue H54, isoleucine residue I56, lysine residue K58, phenylalanine residue F97, tyrosine residue Y98, glycine residue G99, serine residue 100, threonine residue T100A, tryptophan residue W100C, arginine residue R54, arginine residue R65 and tyrosine residue Y102 of the heavy chain.

Additional variants at certain of these positions have been generated. In the light chain, aspartic acid D28 was replaced by asparagine (D28N); glycine G51 was replaced by glutamic acid (G51E) or by tyrosine (G51Y), and phenylalanine residue F96 was replaced by alanine (F96A). In the heavy chain, histidine residue H35 was replace by alanine (H35A), glutamine (H35Q) or glutamic acid (H35E), serine residue S52 was replaced by glycine (S52G) or alanine (S52A), proline residue P52A was replaced by glycine (P52AG), histidine residue H54 was replaced with phenylalanine ($H_{54}F$) or with tryptophan (H54W), isoleucine residue I56 was replaced with tryptophan (I56W) or with lysine (I56K), lysine residue K58 was replaced with glutamine (K58Q), phenylalanine residue F97 was replaced with tyrosine (F97Y), tyrosine residue Y98 was replaced with alanine (Y98A) or with tryptophan (Y98W), glycine residue G99 was replaced with lysine (G99K), threonine residue T100A was replaced with glutamic acid (T100AE), with arginine (T100AR) or with glycine (T100AG), tryptophan residue W100C was replaced with alanine (W100CA), arginine residue R54 was replaced with glutamine (R54Q), arginine residue R65 was replaced with glutamic acid (R65E) and tyrosine residue Y102 was replaced with alanine (Y102A).

Variants Designed to have Altered Lipid Specificity:

Certain amino acid residues in the light chain and heavy chain of LT1009 have been identified as likely to play a role in specificity of the antibody for S1P. These positions include the glutamic acid at position 50 (E50), asparagine residue at position 93 (N93), and tyrosine at position 105A (T105A) of the light chain and glycine at position 99 (G99) and serine at position 100 (S100) of the heavy chain.

Additional variants at certain of these positions have been generated. In the light chain, asparagine N93 was replaced by glycine (N93G) and tyrosine T105A was replaced with glycine (T105AG).

Variants Designed to have Altered Metal Binding:

As was shown in FIG. 3a, aspartic acid residues D30, D31, D32 and D92 of the light chain were found to coordinate the metal atoms that bridge the antibody and its epitope. As described above, changing the aspartic acid to alanine at positions D30 and D32 (D30A and D32A) eliminated S1P binding by the antibody. Additional substitution mutations at these sites have been made to gain further information about the role of each amino acid residue in metal binding (and thus, antibody binding to S1P). Aspartic acid D30 was replaced either by lysine (D30K), threonine (D30T), arginine (D30R) or tyrosine (D30Y). Aspartic acid D31 was replaced by alanine (D31A) or arginine (D31R). Aspartic acid D32 was replaced by asparagine (D32N) or by arginine (D32R). Aspartic acid D92 was replaced either by alanine (D92A), arginine (D92R) or by glutamine (D92Q).

S1P Binding of Variants of LT1009:

The S1P binding ability of selected anti-S1P variants of LT1009 was determined using direct ELISA and these data are shown in Table 12 below.

TABLE 12

S1P-binding parameters for anti-S1P variants using direct ELISA

| $V_L$ plasmid (mutation) | $V_H$ plasmid (mutation) | $EC_{50}$ (ng/ml) | $B_{max}$ ($A_{450}$) | % WT* (6.4 ng/ml) | ΔΔG* | Binding* |
|---|---|---|---|---|---|---|
| Heavy chain mutations | | | | | | |
| pATH320 (WT) | pATH221 (WT) | 27 ± 5 | 1.4 ± 0.1 | 100% | 0.0 | +++ |
| pATH320 (WT) | pATH221 (T100aG) | 56 | 1.2 | 79% | 2.7 | ++ |
| pATH320 (WT) | pATH221 (W100cA) | 68 | 0.69 | 58% | 4.4 | + |
| pATH320 (WT) | pATH221 (Y98A) | 38 | 1.2 | 76% | 3.9 | ++ |
| pATH320 (WT) | pATH230 (Y98W) | 33 | 1.3 | 92% | 2.2 | ++ |
| pATH320 (WT) | pATH231 (K58Q) | 46 | 1.2 | 85% | 2.9 | ++ |
| pATH320 (WT) | pATH232 (P52aG) | 21 | 1.4 | 95% | 1.7 | +++ |
| pATH320 (WT) | pATH233 (S52G) | 30 | 1.4 | 100% | 2.3 | +++ |
| pATH320 (WT) | pATH234 (H54F) | 18 | 1.4 | 95% | 2.2 | +++ |
| pATH320 (WT) | pATH235 (I56W) | 30 | 1.3 | 95% | 2.6 | +++ |
| pATH320 (WT) | pATH236 (S52A, P52aG, H54F) | 24 | 1.3 | 93% | 2.3 | +++ |
| pATH320 (WT) | pATH237 (S52G, H54F) | 36 | 1.3 | 97% | −0.1 | +++ |
| pATH320 (WT) | pATH238 (I56K, F97Y) | 23 | 1.4 | 97% | 1.0 | +++ |
| pATH320 (WT) | pATH239 (T100aE) | ND | ND | ND | ND | ND |
| pATH320 (WT) | pATH240 (G99K) | 51 | 1.4 | 108% | −6.2 | +++ |
| pATH320 (WT) | pATH241 (H54W, F97Y) | 18 | 1.3 | 103% | 1.8 | +++ |
| pATH320 (WT) | pATH242 (T100aR) | 170 | 1.3 | 74% | 3.1 | + |
| pATH320 (WT) | pATH221 (H35E) | 503 | 0.55 | 55% | 6.9 | + |

TABLE 12-continued

S1P-binding parameters for anti-S1P variants using direct ELISA

| $V_L$ plasmid (mutation) | $V_H$ plasmid (mutation) | $EC_{50}$ (ng/ml) | $B_{max}$ ($A_{450}$) | % WT* (6.4 ng/ml) | ΔΔG* | Binding* |
|---|---|---|---|---|---|---|
| pATH320 (WT) | pATH221 (H35Q) | 63 | 1.2 | 94% | 1.5 | ++ |
| pATH320 (WT) | pATH221 (H35A) | 94 | 1.1 | 95% | 2.2 | ++ |
| Light chain mutations | | | | | | |
| pATH320 (D30A) | pATH221 (WT) | 2400 | 0.57 | 27% | 50 | − |
| pATH320 (D32A) | pATH221 (WT) | − | − | − | 18 | − |
| pATH320 (E50A) | pATH221 (WT) | 3800 | 0.16 | 19% | 11 | − |
| pATH323 (E50N) | pATH221 (WT) | 2400 | 0.52 | 38% | 10 | − |
| pATH324 (E50Q) | pATH221 (WT) | 1300 | 0.45 | 36% | 9.6 | − |
| pATH325 (F96A) | pATH221 (WT) | 270 | 0.58 | 53% | 2.9 | + |
| pATH326 (E50N, F96A) | pATH221 (WT) | − | − | − | 12 | − |
| pATH327 (E50Q, F96A) | pATH221 (WT) | − | − | − | 11 | − |
| pATH328 (D30K, E50Q) | pATH221 (WT) | − | − | − | − | − |
| pATH329 (D30K, D31A, D32N, E50Q, D92A) | pATH221 (WT) | − | − | − | − | − |
| pATH330 (D30K, D31R, D32N, E50Q, D92A) | pATH221 (WT) | 10000 | 0.43 | − | 48. | − |
| pATH331 (D30K, D31A, D32R, E50Q, D92A) | pATH221 (WT) | 6000 | 0.80 | − | 47 | − |
| pATH332 (D30K, D31A, D32N, E50Q, D92R) | pATH221 (WT) | 4200 | 0.81 | − | 46 | − |
| pATH333 (D30K, D31R, D32N, E50Q, D92R) | pATH221 (WT) | 1000 | 1.2 | − | 43 | − |
| pATH334 (D30K, D31R, D32N, E50Q, D92R, N93G) | pATH221 (WT) | 840 | 1.2 | − | 46 | |
| pATH335 (E50Q, D92Q) | pATH221 (WT) | − | − | − | − | − |
| pATH337 (G51E, D92R) | pATH221 (WT) | ND | ND | ND | ND | ND |
| pATH338 (D30T, G51E, D92R) | pATH221 (WT) | 1200 | 0.32 | 46% | − | − |
| pATH339 (D28N, D30R, G51Y, D92R) | pATH221 (WT) | 800 | 0.72 | 75% | −12 | + |
| pATH340 (D30Y, D31R D32N, D92R) | pATH221 (WT) | 1200 | − | 33% | − | − |
| Heavy and light chain mutants | | | | | | |
| pATH320 (E50A) | pATH221 (T100aG) | 2900 | 0.22 | 24% | 12 | − |
| pATH323 (E50N) | pATH221 (T100aG) | 2800 | 0.12 | 18% | 11 | − |
| pATH324 (E50Q) | pATH221 (T100aG) | 1100 | 0.50 | 41% | 12 | − |

*% WT refers to the ELISA signal for each variant relative to WT (LT1009) at a particular concentration (6.4 ug/ml), which is useful for purposes of comparison.
ΔΔG values are theoretical, calculated using computational methods to predict lipid binding.
"Binding" is a qualitative comparison of S1P binding (+++ high affinity, ++ moderate affinity, + low affinity, − no binding), based on evaluation of EC50, Bmax, and % WT.

Example 21

Purification and Production of Anti-LPA Antibodies

Applicant has recently developed a mammalian cell line (CHO CK1sv) that expresses >0.5 mg/ml of the humanized, anti-LPA mAb, LT3015. This stable cell line was utilized in a 50 liter bioreactor campaign to produce large quantities of non-GMP material. Purification of LT3015 from the bioreactor supernatant resulted in >10 grams of antibody material. LT3015 was formulated at 18 mg/ml in 24 mM PBS, 148 mM NaCl, pH 6.5, and this preparation meets strict specifications for purity, aggregation and LPA-binding properties. Therefore, suitable material is available for papain digestion, isolation of the Fab fragment, complex formation with LPA, and crystallization of the LT3015Fab/LPA complex.

Example 22

Information Gained from Comparison of Anti-S1P and Anti-LPA Humanized Antibodies Based on primary structure (amino acid sequence) and three-dimensional (crystal) structure, LT1009 and LT3015 are compared. The relatively minor differences in the amino acid sequences of the antibody hypervariable regions function to discriminate between LPA and S1P, two bioactive lipids with such high structural and chemical identity. The anti-LPA and anti-S1P VH sequences (heavy chain variable domain) are 93% identical outside the CDRs (as expected, the CDRs have lower identity, in this case 46%). The Vk sequences (light chain variable domain) are 59% identical outside the CDRs (19% identity within the CDRs). Information on the locations and nature (e.g., size and/or charge of amino acid side chain) of differences between the two antibody sequences will be used to aid in design of variants for SAR testing.

More information about this discrimination is based on the LT1009Fab/S1P complex crystal structure refined at 2.7 Å resolution. A similar approach is used to determine the structure of the LT3015Fab/LPA complex crystal structure, as described in the Examples above. The amino acid composition of the Ch1-3 domains is identical between LT1009 and LT3015, and thus it is believed that the methods used for cocrystallization of LT1009Fab and S1P will also yield cocrystals of LT3015Fab and LPA.

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of generating an optimized humanized antibody to a lipid, comprising:
   a. providing an amino acid sequence of at least one variable region of a heavy or light chain of a first anti-lipid antibody, wherein the first anti-lipid antibody is specific for a first lipid, and wherein the first anti-lipid antibody is LT1009;
   b. replacing one or more amino acids within the at least one variable region with a different amino acid to yield a variant amino acid sequence, wherein the amino acid replacement(s) is(are) within a complementarity-determining region, and wherein the one or more amino acids replaced is/are selected from the group consisting of: aspartic acid at positions 30, 31, and 32, glutamic acid at position 50, aspartic acid at position 92, leucine at position 94 and phenylalanine at position 96, all of the light chain of LT1009; and threonine at position 33, histidine at position 35, alanine at position 50, serine at position 52, histidine at position 54, isoleucine at position 56, lysine at position 58, phenylalanine at position 97, tyrosine at position 98, threonine at position 100A or tryptophan at position 100C, all of the heavy chain of LT1009;
   c. preparing a second anti-lipid antibody containing the variant amino acid sequence, wherein the amino acid sequences of the first and second anti-lipid antibodies differ only in the variant amino acid sequence;
   d. determining one or more activity criteria of the second anti-lipid antibody;
   e. selecting an optimized anti-lipid antibody based on one or more of the activity criteria, wherein the optimized anti-lipid antibody is the second anti-lipid antibody; and
   f. synthesizing the optimized anti-lipid antibody.

2. A method according to claim 1 wherein steps (a)-(e) are performed in silico.

3. A method according to claim 1 wherein the first lipid is a sphingolipid or a lysolipid.

4. A method according to claim 1 wherein determining the one or more activity criteria of the second antibody is selected from the group consisting of molecular modeling, ELISA, or surface plasmon resonance.

5. A method according to claim 1 wherein the one or more activity criteria of the second antibody is selected from the group consisting of binding affinity for the first lipid, binding affinity for a second lipid, and specificity for the first lipid or specificity for a second lipid, wherein the first and second lipids are different lipid species.

6. A method according to claim 1 further comprising use of three-dimensional structural information about the binding of the first anti-lipid antibody and the first lipid to select a location and/or identity of the amino acid replacement(s).

7. A method according to claim 6 wherein the three-dimensional structural information is molecular modeling data or x-ray crystallography data.

* * * * *

SEQUENCE LISTING

<160> NUMBER OF SEQ ID NOS: 36

<210> SEQ ID NO 1
<211> LENGTH: 26
<212> TYPE: DNA
<213> ORGANISM: Artificial Sequence
<220> FEATURE:
<223> OTHER INFORMATION: primer

<400> SEQUENCE: 1
atggratgga gckggrtctt tmtctt                                    26

<210> SEQ ID NO 2
<211> LENGTH: 21
<212> TYPE: DNA
<213> ORGANISM: Artificial sequence
<220> FEATURE:
<223> OTHER INFORMATION: primer

<400> SEQUENCE: 2
cagtggatag acagatgggg g                                         21

<210> SEQ ID NO 3
<211> LENGTH: 21
<212> TYPE: DNA
<213> ORGANISM: Artificial Sequence
<220> FEATURE:

```
<223> OTHER INFORMATION: primer

<400> SEQUENCE: 3
cagtggatag accgatgggg c                                              21

<210> SEQ ID NO 4
<211> LENGTH: 21
<212> TYPE: DNA
<213> ORGANISM: Artificial sequence
<220> FEATURE:
<223> OTHER INFORMATION: primer

<400> SEQUENCE: 4
cagtggatag actgatgggg g                                              21

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
caagggatag acagatgggg c                                              21

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
gtctctgatt ctagggca                                                  18

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
actggatggt gggaagatgg                                                20

<210> SEQ ID NO 8
<211> LENGTH: 82
<212> TYPE: PRT
<213> ORGANISM: Mus musculus

<400> SEQUENCE: 8

Ala His Ser Asp Ala Val Lys Gly Ala Ser Val Lys Ser Cys Lys Val
1               5                   10                  15

Ser Gly Asp His Thr His Trp Met Lys Arg Gly Trp Gly Cys Ser Arg
            20                  25                  30

His Asp Thr Lys Tyr Asn Met Arg Gly Lys Ala Thr Thr Ala Asp Lys
        35                  40                  45

Ser Ser Thr Thr Ala Tyr Val Asn Ser Thr Ser Ala Val Tyr Cys
    50                  55                  60

Ala Arg Gly Gly Tyr Gly Ser Thr Trp Asp Trp Gly Thr Gly Thr Thr
65                  70                  75                  80

Val Ser
```

```
<210> SEQ ID NO 9
<211> LENGTH: 66
<212> TYPE: PRT
<213> ORGANISM: Mus musculus

<400> SEQUENCE: 9

Thr Thr Val Thr Ser Ala Ser Ser Met Ala Gly Lys Val Thr Arg Cys
1               5                   10                  15

Thr Thr Thr Asp Asp Asp Asp Met Asn Trp Lys Gly Asn Ser Gly Asn
            20                  25                  30

Arg Gly Val Ser Arg Ser Ser Ser Gly Tyr Gly Thr Asp Thr Asn Met
        35                  40                  45

Ser Asp Val Ala Asp Tyr Tyr Cys Ser Asp Asn Thr Gly Ser Gly Thr
    50                  55                  60

Lys Lys
65

<210> SEQ ID NO 10
<211> LENGTH: 11
<212> TYPE: PRT
<213> ORGANISM: Mus musculus

<400> SEQUENCE: 10

Ile Thr Thr Thr Asp Ile Asp Asp Met Asn
1               5                   10

<210> SEQ ID NO 11
<211> LENGTH: 7
<212> TYPE: PRT
<213> ORGANISM: Mus musculus

<400> SEQUENCE: 11

Glu Gly Asn Ile Leu Arg Pro
1               5

<210> SEQ ID NO 12
<211> LENGTH: 9
<212> TYPE: PRT
<213> ORGANISM: Mus musculus

<400> SEQUENCE: 12

Leu Gln Ser Asp Asn Leu Pro Phe Thr
1               5

<210> SEQ ID NO 13
<211> LENGTH: 5
<212> TYPE: PRT
<213> ORGANISM: Mus musculus

<400> SEQUENCE: 13

Asp His Thr Ile His
1               5

<210> SEQ ID NO 14
<211> LENGTH: 17
<212> TYPE: PRT
<213> ORGANISM: Mus musculus

<400> SEQUENCE: 14

Cys Ile Ser Pro Arg His Asp Ile Thr Lys Tyr Asn Glu Met Phe Arg
1               5                   10                  15

Gly
```

```
<210> SEQ ID NO 15
<211> LENGTH: 12
<212> TYPE: PRT
<213> ORGANISM: Mus musculus

<400> SEQUENCE: 15

Gly Gly Phe Tyr Gly Ser Thr Ile Trp Phe Asp Phe
1               5                   10

<210> SEQ ID NO 16
<211> LENGTH: 147
<212> TYPE: PRT
<213> ORGANISM: Mus musculus

<400> SEQUENCE: 16

Met Gly Ser Thr Ala Ile Leu Ala Leu Leu Ala Val Leu Gln Gly
1               5                   10                  15

Val Cys Ser Glu Val Gln Leu Val Gln Ser Gly Ala Glu Val Lys Lys
                20                  25                  30

Pro Gly Glu Ser Leu Lys Ile Ser Cys Gln Ser Phe Gly Tyr Ile Phe
            35                  40                  45

Ile Asp His Thr Ile His Trp Val Arg Gln Met Pro Gly Gln Gly Leu
        50                  55                  60

Glu Trp Met Gly Cys Ile Ser Pro Arg His Asp Ile Thr Lys Tyr Asn
65                  70                  75                  80

Glu Met Phe Arg Gly Gln Val Thr Ile Ser Ala Asp Lys Ser Ser Ser
                85                  90                  95

Thr Ala Tyr Leu Gln Trp Ser Ser Leu Lys Ala Ser Asp Thr Ala Met
            100                 105                 110

Tyr Phe Cys Ala Arg Gly Gly Phe Tyr Gly Ser Thr Ile Trp Phe Asp
        115                 120                 125

Phe Trp Gly Gln Gly Thr Met Val Thr Val Ser Ser Ala Ser Thr Lys
130                 135                 140

Gly Pro Ser
145

<210> SEQ ID NO 17
<211> LENGTH: 134
<212> TYPE: PRT
<213> ORGANISM: Mus musculus

<400> SEQUENCE: 17

Met Asp Met Arg Val Pro Ala Gln Leu Leu Gly Leu Leu Leu Leu Trp
1               5                   10                  15

Leu Pro Gly Ala Arg Cys Glu Thr Thr Leu Thr Gln Ser Pro Ser Phe
                20                  25                  30

Leu Ser Ala Ser Val Gly Asp Arg Val Thr Ile Thr Cys Ile Thr Thr
            35                  40                  45

Thr Asp Ile Asp Asp Asp Met Asn Trp Tyr Gln Gln Glu Pro Gly Lys
        50                  55                  60

Ala Pro Lys Leu Leu Ile Tyr Glu Gly Asn Ile Leu Arg Pro Gly Val
65                  70                  75                  80

Pro Ser Arg Phe Ser Gly Ser Gly Ser Gly Thr Asp Phe Thr Leu Thr
                85                  90                  95

Ile Ser Lys Leu Gln Pro Glu Asp Phe Ala Thr Tyr Tyr Cys Leu Gln
            100                 105                 110

Ser Asp Asn Leu Pro Phe Thr Phe Gly Gln Gly Thr Lys Leu Glu Ile
        115                 120                 125
```

-continued

Lys Arg Glu Trp Ile Pro
            130

<210> SEQ ID NO 18
<211> LENGTH: 17
<212> TYPE: PRT
<213> ORGANISM: Mus musculus

<400> SEQUENCE: 18

Ala Ile Ser Pro Arg His Asp Ile Thr Lys Tyr Asn Glu Met Phe Arg
1               5                   10                  15

Gly

<210> SEQ ID NO 19
<211> LENGTH: 140
<212> TYPE: PRT
<213> ORGANISM: Artificial Sequence
<220> FEATURE:
<223> OTHER INFORMATION: humanized antibody sequence

<400> SEQUENCE: 19

Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
                20                  25                  30

Pro Gly Glu Ser Leu Lys Ile Ser Cys Gln Ser Phe Gly Tyr Ile Phe
            35                  40                  45

Ile Asp His Thr Ile His Trp Met Arg Gln Met Pro Gly Gln Gly Leu
        50                  55                  60

Glu Trp Met Gly Ala Ile Ser Pro Arg His Asp Ile Thr Lys Tyr Asn
65                  70                  75                  80

Glu Met Phe Arg Gly Gln Val Thr Ile Ser Ala Asp Lys Ser Ser Ser
                85                  90                  95

Thr Ala Tyr Leu Gln Trp Ser Ser Leu Lys Ala Ser Thr Ala Met
            100                 105                 110

Tyr Phe Cys Ala Arg Gly Gly Phe Tyr Gly Ser Thr Ile Trp Phe Asp
        115                 120                 125

Phe Trp Gly Gln Gly Thr Met Val Thr Val Ser Ser
    130                 135                 140

<210> SEQ ID NO 20
<211> LENGTH: 127
<212> TYPE: PRT
<213> ORGANISM: Artificial Sequence
<220> FEATURE:
<223> OTHER INFORMATION: humanized antibody sequence

<400> SEQUENCE: 20

Met Ser Val Pro Thr Gln Val Leu Gly Leu Leu Leu Trp Leu Thr
1               5                   10                  15

Asp Ala Arg Cys Glu Thr Thr Val Thr Gln Ser Pro Ser Phe Leu Ser
                20                  25                  30

Ala Ser Val Gly Asp Arg Val Thr Ile Thr Cys Ile Thr Thr Asp
            35                  40                  45

Ile Asp Asp Asp Met Asn Trp Phe Gln Gln Glu Pro Gly Lys Ala Pro
        50                  55                  60

Lys Leu Leu Ile Ser Glu Gly Asn Ile Leu Arg Pro Gly Val Pro Ser
65                  70                  75                  80

Arg Phe Ser Ser Ser Gly Tyr Gly Thr Asp Phe Thr Leu Thr Ile Ser
                85                  90                  95

Lys Leu Gln Pro Glu Asp Phe Ala Thr Tyr Tyr Cys Leu Gln Ser Asp
            100                 105                 110

Asn Leu Pro Phe Thr Phe Gly Gln Gly Thr Lys Leu Glu Ile Lys
        115                 120                 125

<210> SEQ ID NO 21
<211> LENGTH: 435
<212> TYPE: DNA
<213> ORGANISM: Artificial Sequence
<220> FEATURE:
<223> OTHER INFORMATION: humanized antibody sequence

<400> SEQUENCE: 21
aagcttgccg ccaccatgga atggagctgg gtgttcctgt tctttctgtc cgtgaccaca      60
ggcgtgcatt ctgaggtgca gctggtgcag tctggagcag aggtgaaaaa gcccggggag     120
tctctgaaga tctcctgtca gagttttgga tacatcttta tcgaccatac tattcactgg    180
atgcgccaga tgcccgggca aggcctggag tggatggggg ctatttctcc cagacatgat    240
attactaaat acaatgagat gttcagggc caggtcacca tctcagccga caagtccagc     300
agcaccgcct acttgcagtg gagcagcctg aaggcctcgg acaccgccat gtatttctgt    360
gcgagagggg ggttctacgg tagtactatc tggtttgact tttggggcca agggacaatg    420
gtcaccgtct cttca                                                    435

<210> SEQ ID NO 22
<211> LENGTH: 396
<212> TYPE: DNA
<213> ORGANISM: Artificial Sequence
<220> FEATURE:
<223> OTHER INFORMATION: humanized antibody sequence

<400> SEQUENCE: 22
aagcttgccg ccaccatgtc tgtgcctacc caggtgctgg gactgctgct gctgtggctg      60
acagacgccc gctgtgaaac gacagtgacg cagtctccat ccttcctgtc tgcatctgta    120
ggagacagag tcaccatcac ttgcataacc accactgata ttgatgatga tatgaactgg    180
ttccagcagg aaccagggaa agcccctaag ctcctgatct ccgaaggcaa tattcttcgt    240
cctggggtcc catcaagatt cagcagcagt ggatatggca cagatttcac tctcaccatc    300
agcaaattgc agcctgaaga ttttgcaact tattactgtt tgcagagtga taacttacca    360
ttcactttcg gccaagggac caagctggag atcaaa                              396

<210> SEQ ID NO 23
<211> LENGTH: 1428
<212> TYPE: DNA
<213> ORGANISM: Artificial Sequence
<220> FEATURE:
<223> OTHER INFORMATION: humanized antibody sequence

<400> SEQUENCE: 23
aagcttgccg ccaccatgga atggagctgg gtgttcctgt tctttctgtc cgtgaccaca      60
ggcgtgcatt ctgaggtgca gctggtgcag tctggagcag aggtgaaaaa gcccggggag     120
tctctgaaga tctcctgtca gagttttgga tacatcttta tcgaccatac tattcactgg    180
atgcgccaga tgcccgggca aggcctggag tggatggggg ctatttctcc cagacatgat    240
attactaaat acaatgagat gttcagggc caggtcacca tctcagccga caagtccagc     300
agcaccgcct acttgcagtg gagcagcctg aaggcctcgg acaccgccat gtatttctgt    360
gcgagagggg ggttctacgg tagtactatc tggtttgact tttggggcca agggacaatg    420

```
gtcaccgtct cttcagcctc caccaagggc ccatcggtct ccccctggc accctcctcc    480 aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagagagttg agcccaaatc ttgtgacaaa actcacacat gcccaccgtg cccagcacct    780
gaactcctgg ggggaccgtc agtcttcctc ttccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caagggcag ccccgagaac cacaggtgta caccctgccc   1140
ccatcccggg aggagatgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tctatagcaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaatag                1428
```

<210> SEQ ID NO 24
<211> LENGTH: 455
<212> TYPE: PRT
<213> ORGANISM: Artificial Sequence
<220> FEATURE:
<223> OTHER INFORMATION: humanized antibody sequence

<400> SEQUENCE: 24

```
Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Glu Ser Leu Lys Ile Ser Cys Gln Ser Phe Gly Tyr Ile Phe
        35                  40                  45

Ile Asp His Thr Ile His Trp Met Arg Gln Met Pro Gly Gln Gly Leu
    50                  55                  60

Glu Trp Met Gly Ala Ile Ser Pro Arg His Asp Ile Thr Lys Tyr Asn
65                  70                  75                  80

Glu Met Phe Arg Gly Gln Val Thr Ile Ser Ala Asp Lys Ser Ser Ser
                85                  90                  95

Thr Ala Tyr Leu Gln Trp Ser Ser Leu Lys Ala Ser Asp Thr Ala Met
            100                 105                 110

Tyr Phe Cys Ala Arg Gly Gly Phe Gly Tyr Gly Ser Thr Ile Trp Phe Asp
        115                 120                 125

Phe Trp Gly Gln Gly Thr Met Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190
```

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Arg Val Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 25
<211> LENGTH: 720
<212> TYPE: DNA
<213> ORGANISM: Artificial Sequence
<220> FEATURE:
<223> OTHER INFORMATION: humanized antibody sequence

<400> SEQUENCE: 25
aagcttgccg ccaccatgtc tgtgcctacc caggtgctgg gactgctgct gctgtggctg      60
acagacgccc gctgtgaaac gacagtgacg cagtctccat ccttcctgtc tgcatctgta     120
ggagacagag tcaccatcac ttgcataacc accactgata ttgatgatga tatgaactgg     180
ttccagcagg aaccagggaa agcccctaag ctcctgatct ccgaaggcaa tattcttcgt     240
cctggggtcc catcaagatt cagcagcagt ggatatggca cagatttcac tctcaccatc     300
agcaaattgc agcctgaaga ttttgcaact tattactgtt tgcagagtga taacttacca     360
ttcactttcg gccaagggac caagctggag atcaaacgta cggtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540

```
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720
```

<210> SEQ ID NO 26
<211> LENGTH: 234
<212> TYPE: PRT
<213> ORGANISM: Artificial Sequence
<220> FEATURE:
<223> OTHER INFORMATION: humanized antibody sequence

<400> SEQUENCE: 26

```
Met Ser Val Pro Thr Gln Val Leu Gly Leu Leu Leu Leu Trp Leu Thr
1               5                   10                  15

Asp Ala Arg Cys Glu Thr Thr Val Thr Gln Ser Pro Ser Phe Leu Ser
                20                  25                  30

Ala Ser Val Gly Asp Arg Val Thr Ile Thr Cys Ile Thr Thr Thr Asp
            35                  40                  45

Ile Asp Asp Asp Met Asn Trp Phe Gln Gln Glu Pro Gly Lys Ala Pro
        50                  55                  60

Lys Leu Leu Ile Ser Glu Gly Asn Ile Leu Arg Pro Gly Val Pro Ser
65                  70                  75                  80

Arg Phe Ser Ser Gly Tyr Gly Thr Asp Phe Thr Leu Thr Ile Ser
                85                  90                  95

Lys Leu Gln Pro Glu Asp Phe Ala Thr Tyr Tyr Cys Leu Gln Ser Asp
                100                 105                 110

Asn Leu Pro Phe Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230
```

<210> SEQ ID NO 27
<211> LENGTH: 121
<212> TYPE: PRT
<213> ORGANISM: Artificial Sequence
<220> FEATURE:
<223> OTHER INFORMATION: humanized antibody sequence

<400> SEQUENCE: 27

```
Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
                20                  25                  30

Thr Ile His Trp Met Arg Gln Met Pro Gly Gln Gly Leu Glu Trp Met
            35                  40                  45
```

```
Gly Ala Ile Ser Pro Arg His Asp Ile Thr Lys Tyr Asn Glu Met Phe
        50                  55                  60

Arg Gly Gln Val Thr Ile Ser Ala Asp Lys Ser Ser Thr Ala Tyr
 65                  70                  75                  80

Leu Gln Trp Ser Ser Leu Lys Ala Ser Asp Thr Ala Met Tyr Phe Cys
                85                  90                  95

Ala Arg Gly Gly Phe Tyr Gly Ser Thr Ile Trp Phe Asp Phe Trp Gly
            100                 105                 110

Gln Gly Thr Met Val Thr Val Ser Ser
            115                 120

<210> SEQ ID NO 28
<211> LENGTH: 363
<212> TYPE: DNA
<213> ORGANISM: Artificial Sequence
<220> FEATURE:
<223> OTHER INFORMATION: humanized antibody sequence

<400> SEQUENCE: 28
gaggtgcagc tggtgcagtc tggagcagag gtgaaaaagc ccggggagtc tctgaagatc      60
tcctgtcaga gttttggata catctttatc gaccatacta ttcactggat cgcccagatg     120
cccgggcaag cctggagtg gatgggggct atttctccca gacatgatat tactaaatac     180
aatgagatgt tcagggggcca ggtcaccatc tcagccgaca gtccagcag caccgcctac     240 ttgcagtgga gcagcctgaa ggcctcggac accgccatgt atttctgtgc gagagggggg     300
ttctacggta gtactatctg gtttgacttt tggggccaag ggacaatggt caccgtctct     360
tca                                                                   363

<210> SEQ ID NO 29
<211> LENGTH: 107
<212> TYPE: PRT
<213> ORGANISM: Artificial Sequence
<220> FEATURE:
<223> OTHER INFORMATION: humanized antibody sequence

<400> SEQUENCE: 29

Glu Thr Thr Val Thr Gln Ser Pro Ser Phe Leu Ser Ala Ser Val Gly
 1               5                  10                  15

Asp Arg Val Thr Ile Thr Cys Ile Thr Thr Thr Asp Ile Asp Asp Asp
                20                  25                  30

Met Asn Trp Phe Gln Gln Glu Pro Gly Lys Ala Pro Lys Leu Leu Ile
            35                  40                  45

Ser Glu Gly Asn Ile Leu Arg Pro Gly Val Pro Ser Arg Phe Ser Ser
 50                  55                  60

Ser Gly Tyr Gly Thr Asp Phe Thr Leu Thr Ile Ser Leu Gln Pro
 65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys
            100                 105

<210> SEQ ID NO 30
<211> LENGTH: 321
<212> TYPE: DNA
<213> ORGANISM: Artificial Sequence
<220> FEATURE:
<223> OTHER INFORMATION: humanized antibody sequence

<400> SEQUENCE: 30
```

```
gaaacgacag tgacgcagtc tccatccttc ctgtctgcat ctgtaggaga cagagtcacc      60
atcacttgca taaccaccac tgatattgat gatgatatga actggttcca gcaggaacca     120
gggaaagccc ctaagctcct gatctccgaa ggcaatattc ttcgtcctgg ggtcccatca     180
agattcagca gcagtggata tggcacagat ttcactctca ccatcagcaa attgcagcct     240
gaagattttg caacttatta ctgtttgcag agtgataact taccattcac tttcggccaa     300
gggaccaagc tggagatcaa a                                               321
```

```
<210> SEQ ID NO 31
<211> LENGTH: 451
<212> TYPE: PRT
<213> ORGANISM: Artificial Sequence
<220> FEATURE:
<223> OTHER INFORMATION: humanized antibody sequence

<400> SEQUENCE: 31
```

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
            20                  25                  30

Thr Ile His Trp Met Arg Gln Met Pro Gly Gln Gly Leu Glu Trp Met
        35                  40                  45

Gly Ala Ile Ser Pro Arg His Asp Ile Thr Lys Tyr Asn Glu Met Phe
    50                  55                  60

Arg Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gly Gly Phe Tyr Gly Ser Thr Ile Trp Phe Asp Phe Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly

```
                305                 310                 315                 320
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 32
<211> LENGTH: 214
<212> TYPE: PRT
<213> ORGANISM: Artificial Sequence
<220> FEATURE:
<223> OTHER INFORMATION: humanized antibody sequence

<400> SEQUENCE: 32

Glu Thr Thr Val Thr Gln Ser Pro Ser Phe Leu Ser Ala Ser Val Gly
1               5                   10                  15

Asp Arg Val Thr Ile Thr Cys Ile Thr Thr Thr Asp Ile Asp Asp Asp
                20                  25                  30

Met Asn Trp Phe Gln Gln Glu Pro Gly Lys Ala Pro Lys Leu Leu Ile
                35                  40                  45

Ser Glu Gly Asn Ile Leu Arg Pro Gly Val Pro Ser Arg Phe Ser Ser
    50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

<210> SEQ ID NO 33
<211> LENGTH: 1356
<212> TYPE: DNA
<213> ORGANISM: Artificial Sequence
<220> FEATURE:
<223> OTHER INFORMATION: humanized antibody sequence

<400> SEQUENCE: 33

```
gaggtgcagc tggtgcagtc tggagcagag gtgaaaaagc ccggggagtc tctgaagatc      60
tcctgtcaga gttttggata catctttatc gaccatacta ttcactgat gcgccagatg     120
cccgggcaag gcctggagtg gatgggggct atttctccca gacatgatat tactaaatac     180
aatgagatgt tcaggggcca ggtcaccatc tcagccgaca gtccagcag caccgcctac     240
ttgcagtgga gcagcctgaa ggcctcggac accgccatgt atttctgtgc gagagggggg     300
ttctacggta gtactatctg gtttgacttt tggggccaag gacaatggt caccgtctct     360
tcagcctcca ccaagggccc atcggtcttc cccctggcac cctcctccaa gagcacctct     420
gggggcacag cggccctggg ctgcctggtc aaggactact ccccgaacc ggtgacggtg     480
tcgtggaact caggcgccct gaccagcggc gtgcacacct cccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga actcctgggg     720
ggaccgtcag tcttcctctt ccccccaaaa cccaaggaca ccctcatgat ctcccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca gtgcaaggt ctccaacaaa gccctcccag cccccatcga gaaaaccatc    1020
tccaaagcca agggcagcc cgagaacca caggtgtaca ccctgccccc atcccgggag    1080
gagatgacca gaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tatagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatag                              1356
```

<210> SEQ ID NO 34
<211> LENGTH: 645
<212> TYPE: DNA
<213> ORGANISM: Artificial Sequence
<220> FEATURE:
<223> OTHER INFORMATION: humanized antibody sequence

<400> SEQUENCE: 34

```
gaaacgacag tgacgcagtc tccatccttc ctgtctgcat ctgtaggaga cagagtcacc      60
atcacttgca taaccaccac tgatattgat gatgatatga ctggttcca gcaggaacca     120
gggaaagccc ctaagctcct gatctccgaa ggcaatattc ttcgtcctgg ggtcccatca     180
agattcagca gcagtggata tggcacagat ttcactctca ccatcagcaa attgcagcct     240
gaagattttg caacttatta ctgttttcag agtgataact accattcac tttcggccaa     300
gggaccaagc tggagatcaa acgtacggtg gctgcaccat ctgtcttcat cttcccgcca     360
tctgatgagc agttgaaatc tggaactgcc tctgttgtgt gcctgctgaa taacttctat     420
```

```
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac agggagagt gttag                    645
```

<210> SEQ ID NO 35
<211> LENGTH: 450
<212> TYPE: PRT
<213> ORGANISM: Artificial Sequence
<220> FEATURE:
<223> OTHER INFORMATION: humanized antibody sequence

<400> SEQUENCE: 35

```
Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
            20                  25                  30

Thr Ile His Trp Met Arg Gln Met Pro Gly Gln Gly Leu Glu Trp Met
        35                  40                  45

Gly Ala Ile Ser Pro Arg His Asp Ile Thr Lys Tyr Asn Glu Met Phe
    50                  55                  60

Arg Gly Gln Val Thr Ile Ser Ala Asp Lys Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gly Gly Phe Tyr Gly Ser Thr Ile Trp Phe Asp Phe Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                    325                 330                 335
Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 36
<211> LENGTH: 1959
<212> TYPE: DNA
<213> ORGANISM: Artificial Sequence
<220> FEATURE:
<223> OTHER INFORMATION: humanized antibody sequence

<400> SEQUENCE: 36
gaggtgcagc tggtgcagtc tggagcagag gtgaaaaagc ccggggagtc tctgaagatc      60
tcctgtcaga gttttggata catctttatc gaccatacta ttcactggat gcgccagatg     120
cccgggcaag gcctggagtg gatgggggct atttctccca acatgatat tactaaatac     180 aatgagatgt tcaggggcca ggtcaccatc tcagccgaca gtccagcag caccgcctac     240 ttgcagtgga gcagcctgaa ggcctcggac accgccatgt atttctgtgc gagagggggg     300
ttctacggta gtactatctg gtttgacttt gggggccaag ggacaatggt caccgtctct     360
tcagcctcca ccaagggccc atcggtcttc ccctggcac cctcctccaa gagcacctct     420
gggggcacag cggccctggg ctgcctggtc aaggactact ccccgaacc ggtgacggtg     480 tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttggt     660
gagaggccag cacagggagg gagggtgtct gctggaagcc aggctcagcg ctcctgcctg     720
gacgcatccc ggctatgcag tcccagtcca gggcagcaag gcaggccccg tctgcctctt     780 caccccggagg cctctgcccg cccactcat gctcagggag agggtcttct ggcttttttcc     840 ccaggctctg gcaggcaca ggctaggtgc cctaaccca ggccctgcac acaaaggggc     900
aggtgctggg ctcagacctg ccaagagcca tatccgggag accctgccc ctgacctaag     960 cccaccccaa aggccaaact ctccactccc tcagctcgga ccttctctct cctcccagat    1020
tccagtaact cccaatcttc tctctgcaga gcccaaatct tgtgacaaaa ctcacacatg    1080
cccaccgtgc ccaggtaagc cagcccaggc ctcgccctcc agctcaaggc gggacaggtg    1140
ccctagagta gcctgcatcc agggacaggc cccagccggg tgctgacacg tccacctcca    1200
tctcttcctc agcacctgaa ctcctggggg gaccgtcagt cttcctcttc ccccaaaac    1260 ccaaggacac cctcatgatc tcccggaccc ctgaggtcac atgcgtggtg gtggacgtga    1320
```

-continued

```
gccacgaaga ccctgaggtc aagttcaact ggtacgtgga cggcgtggag gtgcataatg    1380
ccaagacaaa gccgcgggag gagcagtaca acagcacgta ccgtgtggtc agcgtcctca    1440
ccgtcctgca ccaggactgg ctgaatggca aggagtacaa gtgcaaggtc tccaacaaag    1500
ccctcccagc ccccatcgag aaaccatct ccaaagccaa aggtgggacc cgtggggtgc     1560
gagggccaca tggacagagg ccggctcggc ccaccctctg ccctgagagt gaccgctgta    1620
ccaacctctg tccctacagg gcagccccga gaaccacagg tgtacaccct gcccccatcc    1680
cgggaggaga tgaccaagaa ccaggtcagc ctgacctgcc tggtcaaagg cttctatccc    1740
agcgacatcg ccgtggagtg ggagagcaat gggcagccgg agaacaacta caagaccacg    1800
cctcccgtgc tggactccga cggctccttc ttcctctata gcaagctcac cgtggacaag    1860
agcaggtggc agcaggggaa cgtcttctca tgctccgtga tgcatgaggc tctgcacaac    1920
cactacacgc agaagagcct ctccctgtct ccgggttag                            1959
```